US007639856B2

(12) United States Patent (10) Patent No.: US 7,639,856 B2
Inoue et al. (45) Date of Patent: Dec. 29, 2009

(54) RADIATION IMAGE PROCESSING APPARATUS, IMAGE PROCESSING SYSTEM, RADIATION IMAGE PROCESSING METHOD, STORAGE MEDIUM, AND PROGRAM

(75) Inventors: Hitoshi Inoue, Kanagawa (JP); Makoto Nokita, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 344 days.

(21) Appl. No.: 11/469,986

(22) Filed: Sep. 5, 2006

(65) Prior Publication Data

US 2007/0019847 A1 Jan. 25, 2007

Related U.S. Application Data

(62) Division of application No. 10/131,401, filed on Apr. 25, 2002, now Pat. No. 7,142,705.

(30) Foreign Application Priority Data

| May 1, 2001 | (JP) | ............................. 2001-134204 |
| May 1, 2001 | (JP) | ............................. 2001-134205 |
| May 1, 2001 | (JP) | ............................. 2001-134208 |
| May 1, 2001 | (JP) | ............................. 2001-134210 |
| Jul. 23, 2001 | (JP) | ............................. 2001-221583 |

(51) Int. Cl.
*G06K 9/00* (2006.01)
*G21K 1/00* (2006.01)
(52) U.S. Cl. ..................................... 382/132; 378/155
(58) Field of Classification Search ....................... None
See application file for complete search history.

(56) References Cited

U.S. PATENT DOCUMENTS

| 5,050,198 | A | * | 9/1991 | Honda ....................... 378/98.2 |
| 5,173,788 | A | * | 12/1992 | Ohta .......................... 382/264 |
| 5,801,385 | A | | 9/1998 | Endo et al. .................. 250/370 |
| 6,157,700 | A | | 12/2000 | Sako ....................... 378/98.12 |
| 6,173,086 | B1 | | 1/2001 | Hara .......................... 382/276 |
| 6,269,176 | B1 | * | 7/2001 | Barski et al. ................ 382/128 |
| 6,333,990 | B1 | | 12/2001 | Yazici et al. ................ 382/132 |
| 6,587,594 | B1 | | 7/2003 | Yamada ..................... 382/260 |
| 2001/0012407 | A1 | * | 8/2001 | Takeo ......................... 382/260 |

FOREIGN PATENT DOCUMENTS

| JP | 3-12785 | 1/1991 |
| JP | 8-088765 | 4/1996 |
| JP | 2507659 | 5/1996 |
| JP | 9-75332 | 3/1997 |
| JP | 9-78970 | 3/1997 |
| JP | 2754068 | 3/1998 |
| JP | 11-285493 | 10/1999 |
| JP | 2006-272013 | 10/2006 |

* cited by examiner

*Primary Examiner*—Charles Kim
(74) *Attorney, Agent, or Firm*—Fitzpatrick, Cella, Harper & Scinto

(57) ABSTRACT

The disclosure is made for an apparatus for processing a radiation image of an object obtained by radiography using a grid which is used to remove scattered radiation from the object.

The apparatus includes generation means for generating image components due to the grid on the basis of data of the radiation image, to remove the image components due to the grid from the radiation image.

21 Claims, 44 Drawing Sheets

DEFECTIVE PIXEL

DIRECTION OF GRID STRIPES

RADIATION IMAGE PROCESSING APPARATUS, IMAGE PROCESSING SYSTEM, RADIATION IMAGE PROCESSING METHOD, STORAGE MEDIUM, AND PROGRAM

CROSS REFERENCE TO RELATED APPLICATIONS

This application is divisional of U.S. patent application Ser. No. 10/131,401, filed Apr. 25, 2002 and claims benefit of the filling date of that application, and priority benefit of the filing dates of Japanese patent application nos. 2001-134204, 2001-134205, 2001-134208, 2001-134210 and 2001-221583, filed May 1, 2001, May 1, 2001, May 1, 2001 and Jul. 23, 2001, respectively. The entire disclosure of each of those prior applications is incorporated herein by reference.

FIELD OF THE INVENTION

The present invention relates to an apparatus, a system, a method, a program, and a computer-readable storage medium storing the program, for a radiation image of an object obtained by radiography using a grid which is used to remove scattered radiation from the object.

BACKGROUND OF THE INVENTION

Conventionally, a technique for visualizing the interior of an object by irradiating an object (article) with radiation represented by X-rays and imaging the spatial distribution (radiation distribution) of radiation components which have been transmitted through the object is used. However, since the radiation generates scattered radiation (scattered rays) inside the object, the scattered radiation (scattered rays) is imaged together with directly transmitted radiation (direct rays) that has been transmitted through the object.

The generation process of scattered rays depends on the type of radiation, and the physical properties, structure, or the like of the object, and scattered rays are normally unpredictable. Hence, in order to obtain a radiation image free from any scattered rays, various measures must be taken.

In a typical method of easily obtaining a radiation image free from any scattered rays, a wall made of a radiation-shielding material such as lead or the like is provided to a radiation image-receiving surface to restrict the angles of radiation components that can reach the image receiving surface, thereby intercepting scattered ray components.

More specifically, in radiography in the medical field, a device called "grid" is inserted between an object such as a human body or the like and the X-ray image-receiving surface to remove X-rays scattered from the object.

The grid is a device formed by alternately arranging, in a predetermined width, an X-ray shielding material such as lead or the like, and an X-ray transparent material such as wood, paper, aluminum, carbon, or the like to have angles in a direction to converge to an X-ray generation source (focal point).

Since the aforementioned grid removes some direct rays, the shade of the grid (the shadow of the grid, to be also referred to as "grid stripes" hereinafter) is observed on the X-ray image receiving surface. However, by adopting an arrangement which satisfies the requirements that "the X-ray shielding and transparent materials are alternately arranged at accurate spatial periods", "the period is set at a relatively high spatial frequency", and the like, a disrupted feeling experienced by the X-ray image observer due to the presence of grid stripes on the X-ray image is minimized.

FIG. 39 illustrates the arrangement of a grid 940.

Referring to FIG. 39, reference numeral "910" denotes an X-ray generation source; and "920", the radiation directions of X-rays. Reference numeral "930" denotes an object such as a human body or the like; and "950", an X-ray image-receiving surface.

As shown in FIG. 39, the grid 940 normally has a stripe structure in one direction (vertical direction indicated by the arrow in FIG. 39) on a two-dimensional plane due to easy manufacture, and the like.

As a method of reducing (removing) any contrast of the grid stripes, a method of moving only the grid in a direction perpendicular to stripes during X-ray exposure to exploit the integration effect in X-ray exposure on the X-ray image-receiving surface is available.

Note that the radiation image-receiving surface (image-receiving portion) mainly means a radiation film that directly records a radiation distribution on a photosensitive material.

In recent years, as for radiation images for medical use or the like, a method of processing radiation images as digital data is becoming more prevalent than a method of directly forming an image using a radiation film.

For example, a radiation distribution is temporarily converted into an electrical signal (analog signal), which is A/D-converted into numerical value data (digital data). In this manner, the digital radiation image can undergo processes such as filing, an image process, monitor display, and the like with low cost.

However, in case of a digital radiation image, since an image signal must be sampled in a two-dimensional space, a problem of aliasing based on the sampling theorem is notable.

More specifically, in case of a normal image, by setting an appropriate sampling period (shorter period) in a space, aliasing is negligible upon observing an image.

By contrast, in case of a digital radiation image obtained using a grid, a periodic stripe pattern formed by the grid has a very low frequency due to aliasing, or no aliasing is generated due to the sampling period but a low-frequency amplitude variation occurs, thus posing a problem with which the image observer must be concerned.

As a method of removing inappropriate grid stripe patterns due to aliasing or the like, the following methods have been proposed.

A method of converting a radiation image into digital data is roughly classified into two methods, and (method 1) and (method 2) for removing a grid stripe pattern in correspondence with these two methods will be described below.

(Method 1)

In this digital conversion method, a radiation distribution (radiation intensity distribution) is temporarily converted into another energy distribution (that of, e.g., fluorescence), which is scanned to generate an analog video signal (time signal) that spatially samples an image in only one direction. The time signal is A/D-converted based on a separately prepared temporal period.

As an example of this digital conversion method, a method of sequentially converting energy stored in a photostimulable phosphor into light by laser scan, focusing the light, capturing the light as a video signal, and then A/D-converting the video signal is known.

Upon capturing a digital radiation image by the aforementioned digital conversion method, as a method of removing an inappropriate grid stripe pattern due to aliasing or the like, methods described in, e.g., U.S. Pat. Nos. 2,507,659 and 2,754,068, Japanese Patent Laid-Open No. 8-088765, and the like are known.

More specifically, another energy distribution corresponding to the radiation distribution is scanned in a direction perpendicular to the grid stripes to convert the grid stripes into a periodic signal on a video signal, and the analog periodic signal undergoes low-pass filtering and sampling on the time axis. With such normal arrangement of an antialiasing filter, inappropriate grid stripes can be removed.

As a method similar to the aforementioned method, U.S. Pat. No. 2,507,659 has proposed a method for detecting the presence and frequency of a grid stripe pattern image by computing the Fourier transform of a preliminarily sampled image, selecting a low-pass filter based on the detection result, and making low-pass filtering using the selected filter to remove inappropriate grid stripes.

U.S. Pat. No. 2,754,068, Japanese Patent Laid-Open No. 8-088765, and the like have proposed a method of obtaining an image at a desired sampling interval by making sampling on the time axis at an interval shorter than a desired interval in place of analog low-pass filtering proposed by U.S. Pat. No. 2,507,659 to capture image information containing a grid image by removing aliasing of grid stripe pattern information, making digital low-pass filtering that removes grid image components, and then digitally decimating (sub-sampling) image information.

(Method 2)

In this digital conversion method, the radiation intensity distribution is temporarily converted into another energy distribution (that of, e.g., fluorescence, electric field strengths, or the like), which directly undergoes two-dimensional sampling using a plurality of electrical signal conversion elements (photodiodes, capacitors, or the like) in a two-dimensional matrix, and signals sequentially output from the respective conversion elements are A/D-converted.

As a typical one of such digital conversion method, a method using a so-called radiation flat panel sensor, i.e., a method of converting a fluorescence distribution or electric field strength distribution of radiation over a large area into electrical signals using a plurality of conversion elements for respective pixels in a large-screen flat sensor, whose technology has been developed in recent years, is known.

Upon capturing a digital radiation image by the digital conversion method of method 2, it is very difficult to remove an inappropriate grid stripe pattern due to, e.g., aliasing. This is because an antialiasing filter for an analog electrical signal cannot be applied unlike in method 1, since an energy distribution is directly sampled in a two-dimensional space using a plurality of electrical signal conversion elements of a radiation flat panel sensor or the like (to be simply referred to as a "sensor" or "flat panel sensor" hereinafter).

To solve this problem, a method of directly sampling an energy distribution using a sensor at a density which is high enough not to cause any aliasing in a two-dimensional space, and making the aforementioned sub-sampling after a digital antialiasing filter is applied may be used. However, in such method, it is difficult to make high-density sampling in the two-dimensional space due to the arrangement of the electrical signal conversion elements of the sensor, resulting in a considerable increase in cost.

Hence, a method of moving the grid during X-ray exposure is adopted as in the conventional system.

As another method, Japanese Patent Laid-Open No. 9-75332 or the like has proposed a method of preventing inappropriate grid stripes from being generated on an image by completely matching the spacing of grid stripes with the sampling pitch (pixel pitch of the sensor) to match areas where direct rays are intercepted by the grid stripes with pixel gaps for the purpose of removing the grid stripes upon capturing a digital X-ray image by directly sampling the energy distribution using a sensor in a two-dimensional space.

On the other hand, Japanese Patent Laid-Open No. 9-78970, U.S. Pat. No. 5,801,385, and the like have proposed a method of reducing the contrast of grid stripes by setting the spacing of the grid stripes to be smaller than the sampling pitch to be equal to or nearly equal to the width of the aperture of a light-receiving portion of one pixel (one electrical signal conversion element).

U.S. Pat. No. 5,050,198 or the like has proposed a method of removing a grid image by pre-storing images of grid stripe patterns (grid images) under a plurality of photographing conditions, and dividing an image obtained by photographing by one of the plurality of pre-stored grid images, which was obtained under the same or similar photographing condition.

However, the aforementioned conventional radiation image processes and, especially, an image process that captures a radiation image by (method 2), i.e., using a sensor that makes direct sampling in a two-dimensional space and a grid, suffer the following problems.

In the arrangement proposed by Japanese Patent Laid-Open No. 9-75332 or the like, it is very difficult to completely match the spacing of grid stripes with the sampling pitch. That is, a flat panel sensor which is normally manufactured in a semiconductor manufacturing process, and a grid formed as a combination of relatively thick lead plates are independently prepared, or the grid itself must be prepared to be detachable depending on a situation. Hence, it is very difficult to completely match the spacing of grid stripes with the pixel pitch (sampling pitch) of the sensor due to these factors.

On the other hand, in the arrangement proposed by Japanese Patent Laid-Open No. 9-78970, U.S. Pat. No. 5,801,385, or the like, it is effective to set the spacing of grid stripes to be smaller than the sampling pitch so as to be equal to or nearly equal to the width of the aperture of the light-receiving portion of one pixel. However, when the sensor (flat panel sensor) has high density and the sampling pitch becomes, e.g., 0.1 mm or less, a very small spacing of grid stripes (e.g., 10 stripes per mm) is required. In order to form a grid with such fine stripes, since the thickness of the lead plate used to intercept scattered rays is nearly fixed, areas where direct rays are transmitted through must be narrowed down. As a result, the use efficiency of the radiation dose drops very much, thus disturbing satisfactory radiography.

In the aforementioned conventional arrangement, the grid itself is moved during radiation exposure. Upon moving the grid, a drive system or the like used to move the grid results in an increase in cost and a bulky system, and an arrangement for adjustment control or the like of the relationship between the drive timing and radiation exposure timing, the relationship of the drive speed, and the like must be provided. Therefore, the arrangement that moves the grid cannot always be adopted although it is effective for removing grid stripes as it has the aforementioned limitations.

To solve the above problems, a method of removing grid stripes by digital filtering since the obtained radiation image is digital data may be used. With this method, if the spatial frequency of the grid stripes is completely separated from the spatial frequency components of effective image information based on an object, the grid stripes can be removed by a simple filtering arrangement.

As an example of this method, Japanese Patent Laid-Open No. 3-12785 or the like has proposed a method of removing or reducing data corresponding to the spatial frequency of grid stripes using Fourier transformation.

Also, a method of removing or reducing data corresponding to the spatial frequency of grid stripes using a normal FIR (Finite Impulse Response) filter has been proposed.

Since the grid stripe image is a shadow formed as a result of reducing the radiation transmittance by an X-ray shielding material such as lead or the like, it is multiplicatively superposed on a signal, but it is additively superposed if log conversion is done. Hence, the aforementioned filtering can be made.

In general, the manufacturing process of the grid used to remove scattered rays is managed with very high precision, and grid stripes having uniform spatial frequency characteristics for all kinds of images are prevalently used. For this reason, the aforementioned filtering may be done for only the single spatial frequency.

In practice, since the shape of the grid stripe image (shadow) is not an accurate sine wave shape, double, triple, . . . spatial frequency components as integer frequency multiples may be present. In this case, fundamental wave components alone may be received due to blur resulting from two-dimensional dependency of the conversion process (energy conversion process) of the sensor.

However, a problem with the aforementioned filtering is that it is nearly impossible to limit the spatial frequency band of the image components themselves.

More specifically, for example, as represented by arrangements proposed by U.S. Pat. No. 2,754,068, Japanese Patent Laid-Open No. 8-088765, and the like, grid stripes can be obviously removed by normal filtering without posing any problem as long as a very small spatial sampling pitch is set, an effective Nyquist frequency is increased after sampling to broaden the effective bandwidth (the bandwidth equal to or lower than the Nyquist frequency), and image components and grid stripe components can be perfectly separated in that band. However, it is not effective to decrease the spatial sampling pitch for only the purpose of removing grid stripes since it leads to very high cost of the sensor due to factors such as a semiconductor process and the like, and results in radiation capture efficiency drop.

Hence, it is effective to arrange the sensor itself with a spatial sampling pitch at which effective image components can nearly fall within a frequency band equal to or lower than the Nyquist frequency in terms of cost and performance. However, with this arrangement, the spatial frequency components of the grid stripes and effective image components inevitably overlap each other to some extent.

More specifically, such problem will be explained below using, e.g., FIGS. 40A to 40D. FIG. 40A shows an image signal when an image to be processed (source image) is observed one-dimensionally, and that image signal is made up of 256 numerical values.

FIG. 40B shows the response characteristics of a filter in the spatial frequency domain upon filtering the image signal shown in FIG. 40A. In FIG. 40B, the frequency domain is expressed by numerical values ranging from "0" to "128" in consideration of discrete Fourier transformation, and FIG. 40B expresses trap filtering at the position of the spatial frequency value="100".

FIG. 40C shows the result of filtering shown in FIG. 40B of the image signal shown in FIG. 40A. As can be seen from FIG. 40C, the characteristics of the image signal shown in FIG. 40C are nearly equal to those of the image signal shown in FIG. 40A.

FIG. 40D shows the difference between the image signals shown in FIGS. 40A and 40C for the purpose of confirmation. As can be seen from FIG. 40D, almost no signal components are removed by filtering.

FIG. 41A shows an image signal formed by adding a steeply rising middle portion (so-called edge portion) to the image signal (source image signal) shown in FIG. 40A.

FIG. 41B shows, as in FIG. 40B, the response characteristics of a filter in the spatial frequency domain upon filtering the image signal shown in FIG. 41A.

FIG. 41C shows the result of filtering shown in FIG. 41B of the image signal shown in FIG. 41A. As can be seen from portions bounded by circles in FIG. 41C, the filtering result unstably oscillates (artifacts) while being deviated from the source image signal.

FIG. 41D shows the difference between the image signals shown in FIGS. 41A and 41C for the purpose of confirmation. As can be seen from FIG. 41D, many oscillation components appear in portions that vary steeply (including the two end portions of the signal).

As shown in FIGS. 40A to 40D and FIGS. 41A to 41D, in case of a normal image signal, since considerably high-frequency components equal to or lower than the Nyquist frequency (spatial frequency="128" in these figures) are not major components of the image signal and have nearly no information, if steep filtering is done at that position, no serious problem is posed. By contrast, when an image signal has steep portions (edge portion), since an image signal is expressed using considerably high-frequency components equal to or lower than the Nyquist frequency, problems (artifacts) are posed in portions that vary steeply.

FIGS. 42A to 42D show a signal state when a sine wave $(\sin(2\pi 100_x/256))$ is added to the source image signal shown in FIG. 40A upon simulating the grid. As can be seen from FIGS. 42A to 42D, grid stripes are nearly completely removed by filtering having the filter response characteristics shown in FIG. 42B (see FIG. 42C).

FIGS. 43A to 43C show a signal state when a sine wave $(\sin(2\pi 100_x/256))$ is added to the source image signal shown in FIG. 41A upon simulating the grid. As can be seen from FIGS. 43A to 43C, artifacts similar to those in FIG. 41C are generated by filtering having the filter response characteristics shown in FIG. 43B (see FIG. 43C).

That is, if grid stripe components are removed by a simple filtering process described in Japanese Patent Laid-Open No. 3-12785 or the like, the aforementioned artifacts may be generated intensely. If the impulse response width of the filter is narrowed to reduce artifacts, the response characteristics of filtering are reduced over a broad range, thus forming a strongly blunted image.

The present invention has been made to remove the above drawbacks, and has as its object to provide an apparatus, a system, a method, a program and a computer-readable storage medium storing the program, which can obtain a satisfactory radiation image of an object, substantially free from image components due to a grid, from a radiation image obtained by radiography using the grid.

SUMMARY OF THE INVENTION

In order to achieve the above object, one aspect of the present invention is an apparatus for processing a radiation image of an object obtained by radiography using a grid which is used to remove scattered radiation from the object, to remove image components due to the grid, comprising, generation means for generating the image components due to the grid on the basis of data of the radiation image. One aspect of the present invention is a method of processing a radiation image of an object obtained by radiography using a grid which is used to remove scattered radiation from the object, to remove image components due to the grid, comprising, a generation step of generating the image components due to the grid on the basis of data of the radiation image.

In order to achieve another object, one aspect of the present invention is an apparatus for processing a radiation image of an object obtained by radiography using a grid which is used to remove scattered radiation from the object, to remove image components due to the grid, comprising, generation means for generating the image components due to the grid on the basis of a predetermined radiation image; and removal means for executing a removal process of the image components for a plurality of radiation images on the basis of the image components of said predetermined radiation image obtained by said generation means.

One aspect of the present invention is a method of processing a radiation image of an object obtained by radiography using a grid which is used to remove scattered radiation from the object, to remove image components due to the grid, comprising, a generation step of generating the image components due to the grid on the basis of a predetermined radiation image; and a removal step of executing a removal process of the image components for a plurality of radiation images on the basis of the image components of said predetermined radiation image obtained in said generation step. In order to achieve another object, one aspect of the present invention is an apparatus for processing a radiation image of an object obtained by radiography using a grid which is moved and used to remove scattered radiation from the object, to remove image components due to the grid, comprising, detection means for detecting the image components due to the grid on the radiation image, generation means for generating the image components on the basis of a detection result of said detection means and data of the radiation image, and arithmetic means for removing the image components generated by said generation means from the radiation image.

One aspect of the present invention is an apparatus for processing a radiation image of an object obtained by radiography using a grid which is moved and used to remove scattered radiation from the object, to remove image components due to the grid, comprising, exposure time measurement means for measuring a radiation exposure time, moving distance measurement means for measuring a moving distance of the grid, signal output means for outputting a signal indicating presence of the image components due to the grid on the radiation image in accordance with measurement results of said exposure time measurement means and said moving distance measurement means, generation means for generating the image components on the basis of a signal output from said signal output means and data of the radiation image, and arithmetic means for removing the image components generated by said generation means from the radiation image.

One aspect of the present invention is an apparatus for processing a radiation image of an object obtained by radiography using a grid which is moved at a predetermined speed and used to remove scattered radiation from the object, to remove image components due to the grid, comprising, exposure time measurement means for measuring a radiation exposure time, signal output means for outputting a signal indicating presence of the image components due to the grid on the radiation image in accordance with a measurement result of said exposure time measurement means, generation means for generating the image components on the basis of a signal output from said signal output means and data of the radiation image, and arithmetic means for removing the image components generated by said generation means from the radiation image.

One aspect of the present invention is a method of processing a radiation image of an object obtained by radiography using a grid which is moved and used to remove scattered radiation from the object, to remove image components due to the grid, comprising, a detection step of detecting the image components due to the grid on the radiation image, a generation step of generating the image components on the basis of a detection result in the detection step and data of the radiation image, and an arithmetic step of removing the image components generated in the generation step from the radiation image.

One aspect of the present invention is a method of processing a radiation image of an object obtained by radiography using a grid which is moved and used to remove scattered radiation from the object, to remove image components due to the grid, comprising, an exposure time measurement step of measuring a radiation exposure time, a moving distance measurement step of measuring a moving distance of the grid, a signal output step of outputting a signal indicating presence of the image components due to the grid on the radiation image in accordance with measurement results in the exposure time measurement step and the moving distance measurement step, a generation step of generating the image components on the basis of a signal output in the signal output step and data of the radiation image, and an arithmetic step of removing the image components generated in the generation step from the radiation image.

One aspect of the present invention is a method of processing a radiation image of an object obtained by radiography using a grid which is moved at a predetermined speed and used to remove scattered radiation from the object, to remove image components due to the grid, comprising, an exposure time measurement step of measuring a radiation exposure time, a signal output step of outputting a signal indicating presence of the image components due to the grid on the radiation image in accordance with a measurement result in the exposure time measurement step, a generation step of generating the image components on the basis of a signal output in the signal output step and data of the radiation image, and an arithmetic step of removing the image components generated in the generation step from the radiation image.

In order to achieve another object, one aspect of the present invention is an apparatus for processing a radiation image of an object obtained by radiography using a grid which is used to remove scattered radiation from the object, comprising, first generation means for generating image components due to the grid on the basis of first image data obtained by radiography using the grid without an object, second generation means for generating correction image data by removing the image components due to the grid from the first image data, and correction means for correcting second image data obtained by radiography of an object using the correction image data. One aspect of the present invention is an apparatus for processing a radiation image of an object obtained by radiography using a grid which is used to remove scattered radiation from the object, comprising, first generation means for generating first image components due to the grid on the basis of first image data obtained by radiography using the grid without an object, second generation means for generating correction image data by removing the first image components from the first image data, third generation means for correcting second image data obtained by radiography of an object using the correction image data, and generating third image data, fourth generation means for generating second image components due to the grid on the basis of the third image data; and fifth generation means for generating processed image data by removing the second image components from the third image data.

One aspect of the present invention is a method of processing a radiation image of an object obtained by radiography using a grid which is used to remove scattered radiation from the object, comprising, a first generation step of generating image components due to the grid on the basis of first image data obtained by radiography using the grid without an object, a second generation step of generating correction image data by removing the image components due to the grid from the first image data; and a correction step of correcting second image data obtained by radiography of an object using the correction image data.

One aspect of the present invention is a method of processing a radiation image of an object obtained by radiography using a grid which is used to remove scattered radiation from the object, comprising, a first generation step of generating first image components due to the grid on the basis of first image data obtained by radiography using the grid without an object, a second generation step of generating correction image data by removing the first image components from the first image data, a third generation step of correcting second image data obtained by radiography of an object using the correction image data, and generating third image data, a fourth generation step of generating second image components due to the grid on the basis of the third image data; and a fifth generation step of generating processed image data by removing the second image components from the third image data.

In order to achieve another object, one aspect of the present invention is an apparatus for processing a radiation image of an object obtained by radiography using a grid which is used to remove scattered radiation from the object, to remove image components due to the grid, wherein upon executing a removal process for removing the image components due to the grid which are superposed on the radiation image, the removal process is not executed for a region of the radiation image where the image components are originally not superposed.

One aspect of the present invention is an apparatus for processing a radiation image of an object obtained by radiography using a grid which is used to remove scattered radiation from the object, to remove image components due to the grid, comprising:mask means for masking the image components due to the grid in accordance with a pixel value of the radiation image; and removing means for removing the image components masked by said mask means from the radiation image.

One aspect of the present invention is a method of processing a radiation image of an object obtained by radiography using a grid which is used to remove scattered radiation from the object, to remove image components due to the grid, wherein upon executing a removal process for removing the image components due to the grid which are superposed on the radiation image, the removal process is not executed for a region of the radiation image where the image components are originally not superposed. One aspect of the present invention is a method of processing a radiation image of an object obtained by radiography using a grid which is used to remove scattered radiation from the object, to remove image components due to the grid, comprising, a mask step of masking the image components due to the grid in accordance with a pixel value of the radiation image, and a removing step of removing the image components masked in said mask step from the radiation image.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Figure 1:
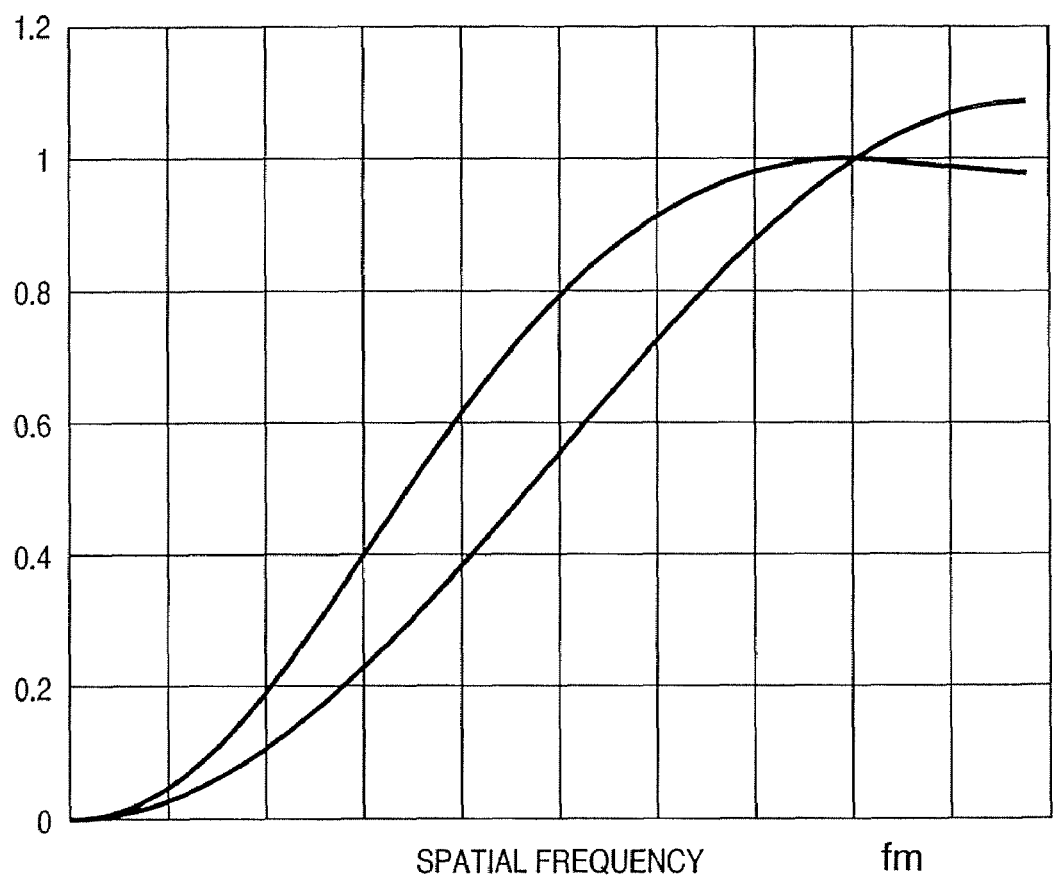
FIG. 1 is a graph for explaining the spatial frequency characteristics of a filter used to extract grid stripe components from an objective image in respective embodiments.

Preferred embodiments of the present invention will be described hereinafter with reference to the accompanying drawings.

The first to 19th embodiments will be exemplified hereinafter as preferred embodiments of the present invention. An outline of the first to fifth embodiments will be explained first.

Outline of First to Fifth Embodiments

Assume that X-rays are used as an example of radiation, and an X-ray image obtained by X-ray radiography will be processed.

The arrangement to be described below is an example to which the present invention is applied, and the present invention is not limited to such specific arrangement.

The present invention solves problems posed when grid stripes are removed by a conventional filtering process (simple filtering process) described especially in Japanese Patent Laid-Open No. 3-12785 or the like by the following arrangement.

That is, component information of grid stripes (to be also simply referred to as "grid stripe components" hereinafter), which is superposed on a signal of an X-ray image to be processed (to be also simply referred to as "objective image signal" or "objective image" hereinafter) and should be present as a stable stripe pattern over the entire image is obtained by estimation. The grid stripe components are removed from the objective image. For example, when the objective image signal is a logarithmic image signal, the obtained grid stripe information is subtracted from the objective image signal. In this manner, the grid stripe information can be stably removed without influencing the objective image signal.

More specifically, components that contain most of the grid stripe components are separated based on the frequency indicated by the grid stripe components, the separated components are processed based on feature information that grid stripes may represent, and the processed information is considered as grid stripe components, which are removed from the objective image signal.

The grid stripe components have considerably intense components according to spatial spectrum expression, and can be present around the Nyquist frequency (spatial frequency ½ the sampling frequency) upon sampling if the spatial frequency of grid stripes are appropriately selected. As a result, a state wherein grid stripe components do not overlap major components of a normal image signal can be easily obtained.

Only when the objective image signal contains steep variation components, it becomes difficult to separate grid stripe components and the objective image signal, as described above using FIGS. 43A to 43D.

In some cases, the objective image includes a region where no grid stripes are present. That is, when an object including a portion that nearly perfectly intercepts X-ray undergoes X-ray radiography or when intense X-rays beyond the dynamic range of a sensor reach a partial region of the sensor, grid stripe components of that region are removed by saturation.

Normally, upon capturing an X-ray image, the X-ray dose outside an object region (through portion) becomes several hundred times that inside the object region since importance is attached to the X-ray dose that is transmitted through the object. In general, it is nonsense to broaden the dynamic range of a sensor or an amplifier for the sensor in consideration of the region outside the object, which has no information. In most cases, the region outside the object corresponds to a region where the input/output characteristics of the sensor exhibit nonlinearity due to saturation, and no grid stripe components are present or the contrast lowers.

Hence, the present invention can adaptively cope with both a case wherein the objective image includes a steep variation (e.g., an edge portion) that makes separation of the grid stripe components and the objective image signal difficult, and a case wherein the objective image includes a region where no grid stripes are present, and can remove grid stripe components without generating any artifacts.

An outline of the first to fifth embodiments as such examples will be explained below.

In the first embodiment, one frame of an objective image (an image obtained by X-ray radiography) is analyzed. As for a pixel defect in a direction perpendicular to the grid stripes, a linear predictive pixel defect correction process is executed.

The grid stripe components are temporarily extracted by low-order FIR filtering on the basis of the analysis result, and envelope information of the filtering result is acquired by a vector amplitude calculation between that filtering result and another FIR filtering result. An unsteady portion is extracted from the grid stripe components based on the envelope information, and is patched using a steady portion around it, thus converting the grid stripe components into a signal sequence which is steady as a whole. Furthermore, in order to extract grid stripe components alone more appropriately, a filtering process for selectively extracting a spatial frequency corresponding to the grid stripe components is executed, and that filtering result is determined to be grid stripe components.

In the second embodiment, the objective image is analyzed, and an image after grid stripe components are removed undergoes pixel defect correction based on the analysis result. As the pixel defect correction, that using, e.g., the average of surrounding pixel values can be applied.

In the third embodiment, a detection means for detecting attachment of a grid is provided. When the detection means confirms attachment of the grid, the objective image is analyzed, and predictive pixel defect correction and removal of grid stripe components are executed based on the analysis result.

In the fourth embodiment, when the irradiation field of X-ray exposure is stopped down in correspondence with a portion to be photographed of an object, only a partial image corresponding to the irradiation field is selected as an objective image, and the process in the first embodiment is executed.

The fifth embodiment adopts a method of inhibiting a grid stripe removal process for an image in a portion where no grid stripes are present if no grid stripes are present in a partial region of an objective image.

More specifically, by replacing information of a portion where no grid stripe components are present in the extracted grid stripe components by zero ("0") data, that portion does not undergo the grid stripe removal process.

In the first to fifth embodiments, for example, since the extracted grid stripe components are image information, that image may be held. When this is done, even when grid stripe components are removed from the objective image, the source objective image, i.e., an image before grid stripes are removed, may be recovered using the held image information of the grid stripe components.

The removal process of grid stripe components in the first to fifth embodiments will be described in detail below.

Note that the first to fifth embodiments will sometimes be referred to as "this embodiment" together in the following description.

The removal process of grid stripe components mainly includes the first to third processing steps as follows.

First Processing Step:

Line data in a direction perpendicular to grid stripes are extracted as samples from an obtained objective image including grid stripe components, thus detecting the spatial frequency of the grid stripes.

Second Processing Step:

Grid stripe components are sequentially extracted from the objective image, and the extraction result (grid stripe components) is subtracted from the objective image. At this time, in consideration of generation of artifacts, components mainly containing grid stripes are extracted by FIR filtering in a relatively short span that can reduce the influence range of artifacts even if they are generated.

Third Processing Step:

The envelope of the components mainly containing the grid stripes, which are obtained in the second processing step, is obtained by a vector amplitude calculation with components obtained by shifting the phase of those components 90° by another FIR filtering different from that for the former components, on the basis of the spatial frequency of the grid stripes obtained in the first processing step.

The removal process of grid stripe components including the first to third processing steps will be described in more detail below. The envelope information obtained in the third processing step always assumes a positive value, and has following features (1) and (2).

(1) A steep variation portion (e.g., an edge portion) assumes a very large value. (2) A portion where no grid stripes are present assumes a small value nearly equal to "0" stabler generation of grid stripe components.

As a patch method of the grid stripe components, a method of replacing the portion of feature (1) by components predicted from a surrounding stable grid stripe portion to obtain grid stripe components which are stable as a whole, may be used.

The components which mainly contain grid stripes in which only stable grid stripe components are present, and are acquired, as described above, undergo a normal filtering process for the entire line. In this case, filtering for extracting only the spatial frequency within a narrower range having the spatial frequency of grid stripes as the center is done.

The filtering result (extracted components) is determined to be grid stripe components in the objective image. In this case, if the envelope information has feature (2), i.e., when components mainly containing grid stripes include a portion where no grid stripe components are present, since no grid components are present, the components mainly containing the grid stripes of that portion are replaced by "0".

Upon executing the filtering process of the objective image, the fast Fourier transform algorithm may be used to attain a stable, high-speed, steeper filtering process. In this case, the data length is limited to the n-th power of "2" (n is a positive integer). For this reason, the length is adjusted by stuffing "0"s around normal data. Data within the range stuffed with "0"s can be considered as those corresponding to the portion in which the envelope information indicates feature (2).

Note that it is effective to select the effective spatial frequency as that of the grid itself from the spatial frequency range (the range from 60% to 80% of the Nyquist frequency) within the range from 30% to 40% of the sampling frequency (the reciprocal of the spatial sampling pitch), as proposed in Japanese Patent Application No. 2000-028161 or the like. This is because major components of an image are concentrated in the range equal to lower than 30% of the sampling frequency and intense grid stripe components having a spatial frequency within the range from 40% to 60% of the sampling frequency appear as if they caused another periodic amplitude variation when an interpolation process such as linear interpolation is done after sampling, resulting in poor stability of the grid stripes themselves.

Let "fg [cyc/mm]" be the spatial frequency of the grid itself, and "T" be the sampling pitch of the sensor. Then, a spatial frequency fm of grid stripes is given by:

$$fm = \left|fg - \frac{n}{T}\right| [cyc/\text{mm}]; n: 0, \pm 1, \pm 2LL \quad (1)$$

where fg is the characteristics of the grid which is attached in practice, and can be determined from the model name of the grid itself. In CXDI, a prescribed grid is used.

In this embodiment, in consideration of the presence of a stripe pattern corresponding to the spatial frequency fm given by equation (1) in the objective image as grid stripe components, grid stripes are accurately extracted in the aforementioned first processing step. That is, since the spatial frequency fg of the grid stripes is known, spatial frequencies around the spatial frequency fm of the objective image are searched, and a spatial frequency that shows a peak value in the search result is considered as the spatial frequency fm of the grid stripes in the objective image.

In the second processing step, grid stripe components are roughly extracted in a state wherein FIR filtering with a shortest possible span having the spatial frequency fm as the center is done for the spatial frequency fm to remove most of effective image components, and in a state wherein the influence of artifacts due to a steep variation (e.g., an edge portion) falls within a narrow range.

At this time, a coefficient sequence of an FIR filter is set to be an even function, and a 3- or 5-tap FIR filter is preferably used to satisfy the narrow range.

More specifically, if a symmetric 3-tap FIR filter is used, and its coefficients are (a1, b1, a1), two conditions, i.e., a condition that the response at the spatial frequency fm is "1" and a condition that the DC component as the central value of image information set to be "0", can be used to obtain these coefficients (a1, b1, a1).

That is, the coefficient arithmetic operations include simultaneous equations:

2*a1+b1=0

2*a1*cos(2πfmT)+b1=1 and have solutions given by:

$$\begin{cases} a1 = \frac{1}{2 \cdot (\cos(2\pi fmT) - 1)} \\ b1 = -2 \cdot a1 \end{cases} \quad (2)$$

The aforementioned FIR filtering has a response="1" at the spatial frequency fm. However, when the spatial frequency exceeds fm, the response rises gradually. In general, since no image components are present in this portion, grid stripes can be sufficiently extracted by this FIR filtering.

If symmetric 5-tap FIR filtering is adopted and its coefficients are (a2, b2, c2, b2, a2), a condition that the differential value of the response at the spatial frequency fm indicates "0" (peak) can also be used in addition to the two conditions, i.e., the condition that the response at the spatial frequency fm is "1" and the condition that the DC component as the central value of image information set to be "0", so as to obtain these coefficients (a2, b2, c2, b2, a2).

That is, by making simple arithmetic operations from the solutions given by equations (2), the coefficient arithmetic operations can yield solutions:

(−a1², 2a1(1−b1), 1−2a1²−(1−b1)²,

2a1(1−b1), −a1²)

As a method of calculating a filter for symmetric 5-tap FIR filtering, for example, if a filter having coefficients (a1, b1, a1) given by equations (2) above is subtracted from "1", a filter having zero point at the spatial frequency fm is obtained. If a process for executing filtering using this filter twice is considered, no phase (sign) inversion occurs although that filter also has zero point at the spatial frequency fm. Such filter is that for symmetric 5-tap FIR filtering, and by subtracting that filter from "1", a filter having a peak at the target spatial frequency fm can be formed.

FIG. 1 shows examples of shapes (spatial frequency characteristics) of symmetric 3-tap FIR filtering (to be also referred to as "3-tap FIR filtering" hereinafter) and symmetric 5-tap FIR filtering (to be also referred to as "5-tap FIR filtering" hereinafter) mentioned above.

The filtering result of the FIR filter shown in FIG. 1 corresponds to an extraction result of only grid stripe components in most cases. As can be seen from FIG. 1, most of low-frequency components of effective image components that mainly consist of such low-frequency components are removed.

However, in practice, components extracted by FIR filtering include many effective image components. Essentially, filtering using a filter having steep selection characteristics having the spatial frequency fm as the center is to be made. Even if such filtering is done, extracted components inevitably include frequency components which form an abrupt variation portion contained in the objective image.

In order to solve this problem, in this embodiment, a local envelope of the grid stripe components is calculated in the third processing step, and a portion that contains components which are more likely to generate artifacts other than the grid stripe components is detected from the variation of the envelope, thereby stably extracting (generating) only grid stripe components.

The envelope of a general signal requires Hilbelt transformation. However, the envelope of a single sine wave can be obtained by applying a spatial filter which has a response amplitude="1" at that frequency and causes a phase drift of 90° (π/2), and then calculating the vector amplitude (square root of square sum) of that filtering result and a source signal.

When filtering using an FIR filter, the phase of which drifts 90°, is applied to discrete data, the coefficients of that FIR filter are set to satisfy point symmetry (odd function). For example, assume that the coefficients are (−a3, 0, a3). In order to set a response="1" at the spatial frequency fm, these coefficients (−a3, 0, a3) must satisfy:

2*a3*sin(2πfmT)=1 and a solution given by:

$$\left\{ a3 = \frac{1}{2 \cdot \sin(2\pi fmT)} \right. \quad (3)$$

is obtained.

The amplitude between a signal sequence obtained by the FIR filter having the coefficients (−a3, 0, a3) of the solution given by equation (3), and a source signal sequence is calculated.

Figure 2:
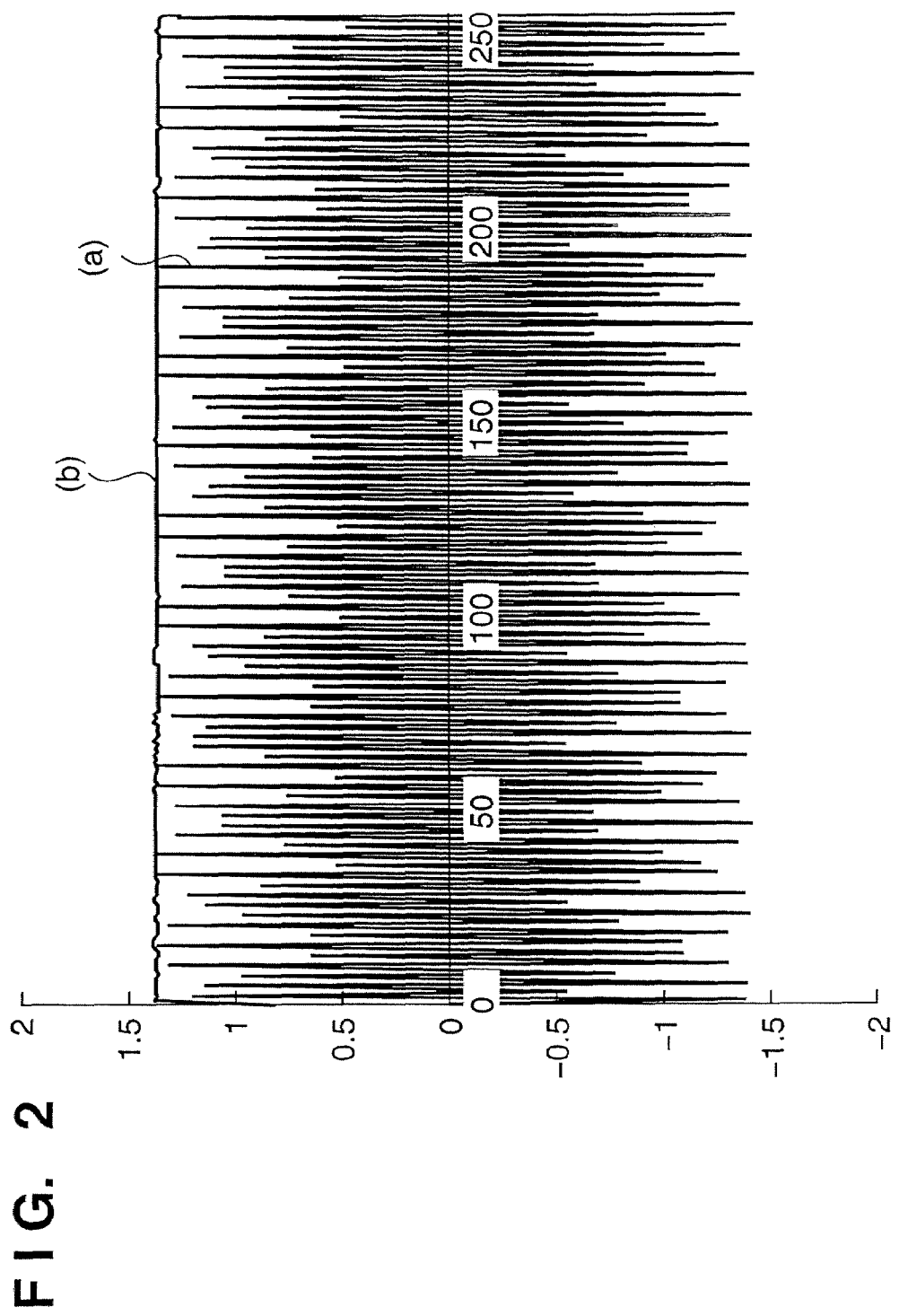
FIG. 2 is a graph for explaining an example of grid stripe components extracted from the objective image by the filter.
Figure 42A:
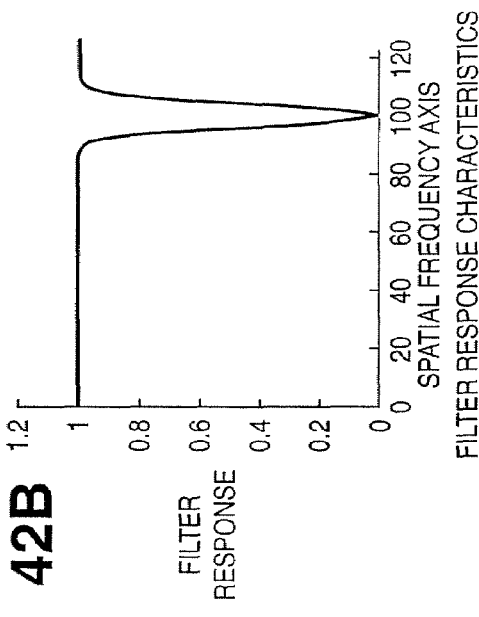
FIGS. 42A to 42D are graphs for explaining another example of the effect of filtering for an image which is obtained by radiography and is superposed with grid stripe components.
Figure 42B:
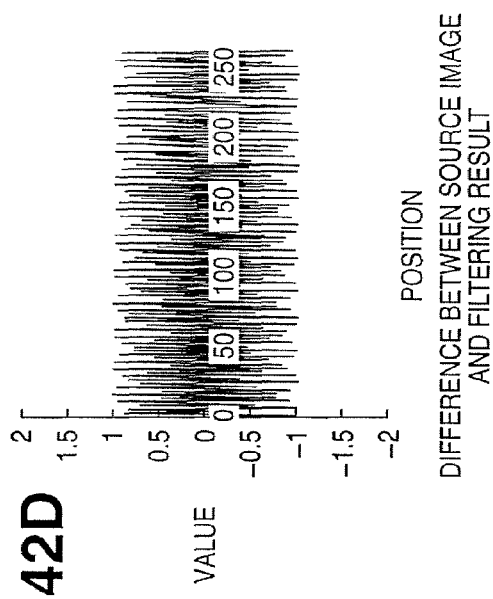
Figure 42C:
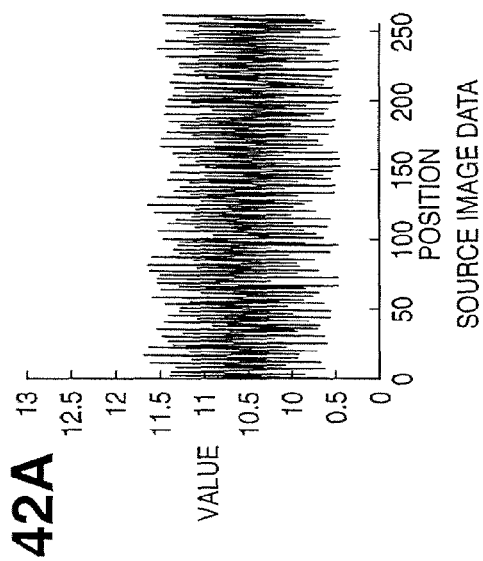
Figure 42D:
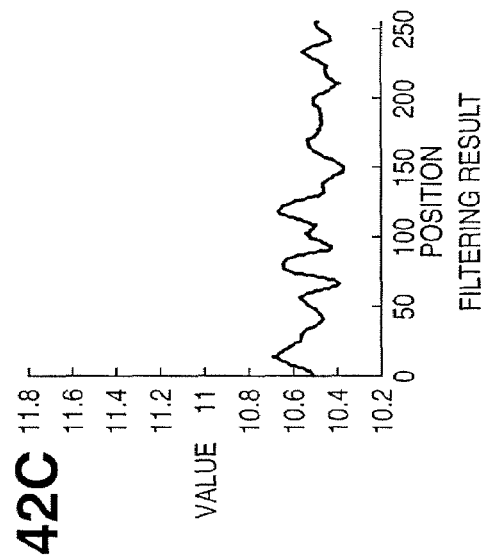

For example, (a) in FIG. 2 indicates the result of filtering having the coefficients (−a3, 0, a3) of the solution given by equation (3) for the image signal shown in FIG. 42A. As can be seen from (a) in FIG. 2, most of grid stripe components are extracted.

Figure 3:
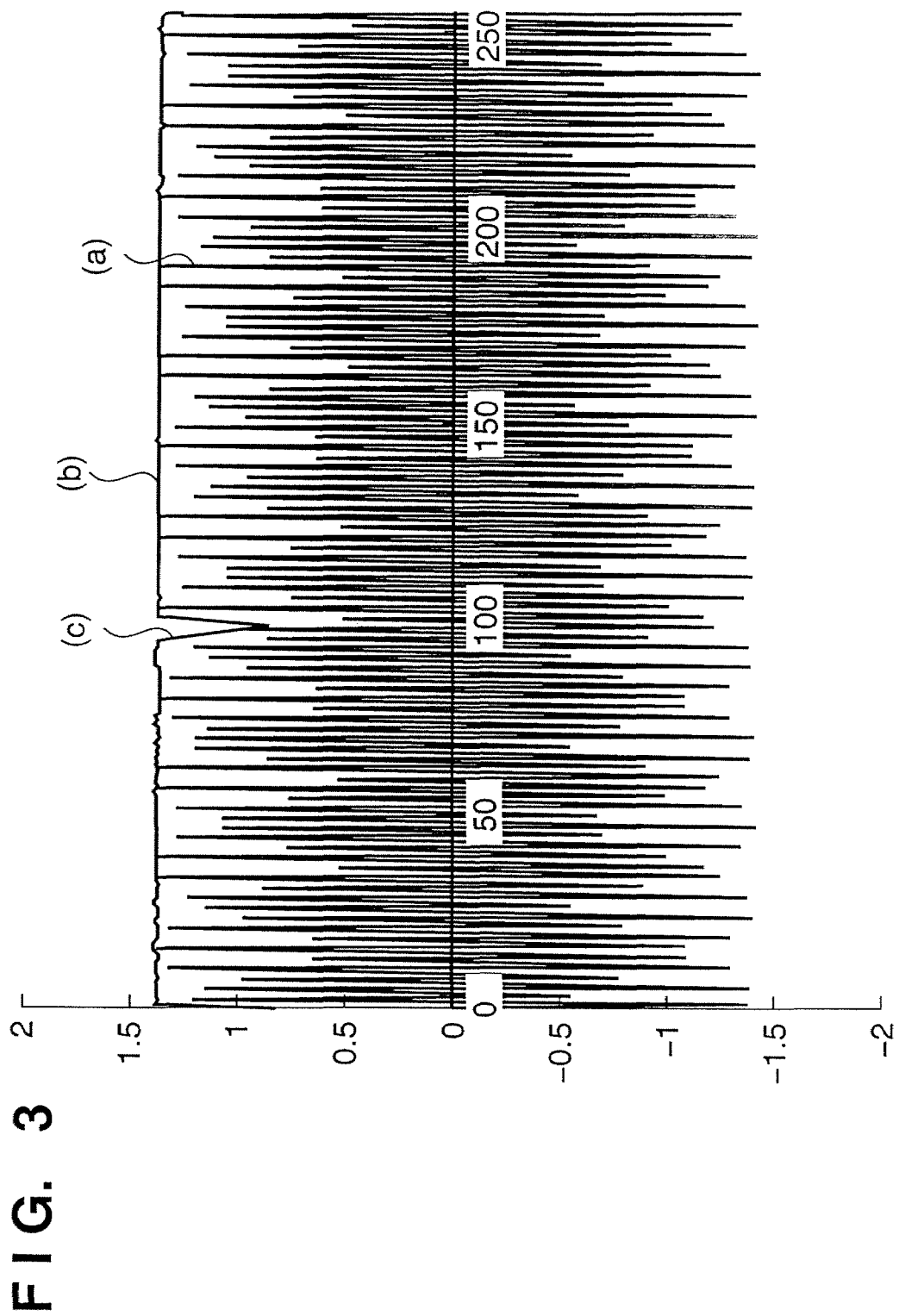
FIG. 3 is a graph for explaining another example of grid stripe components extracted from the objective image by the filter.
Figure 43B:
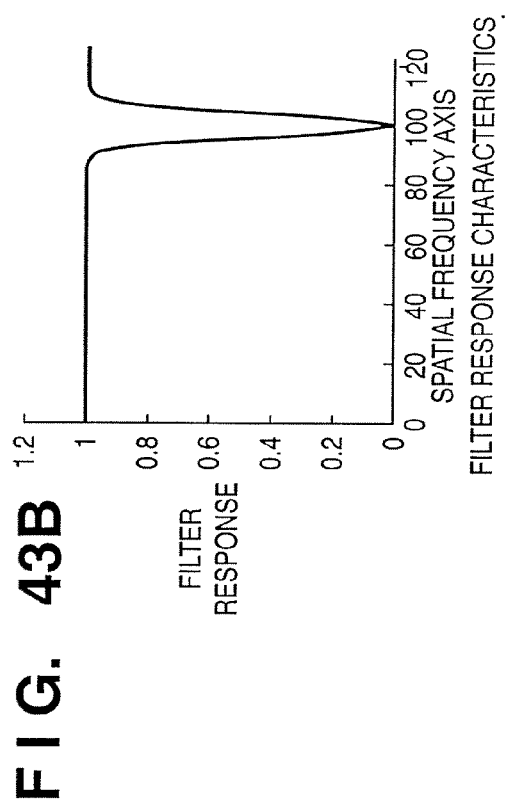
FIGS. 43A to 43D are graphs for explaining another example of the effect of filtering for an image which is obtained by radiography and is superposed with grid stripe components.
Figure 43D:
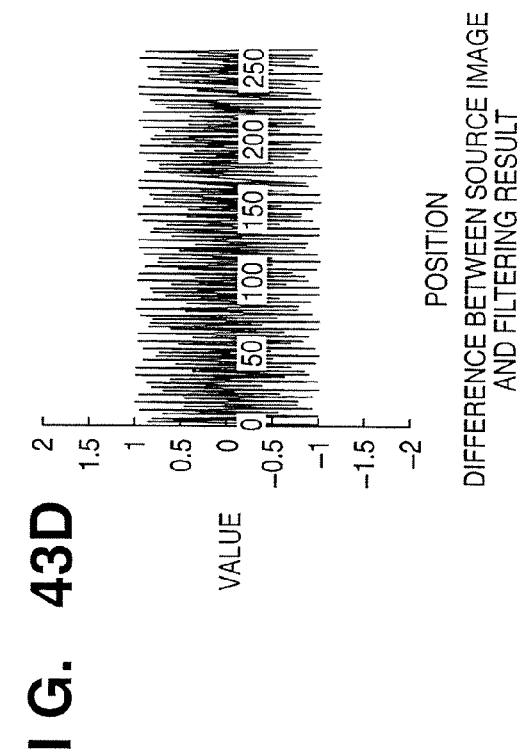
Figure 43A:
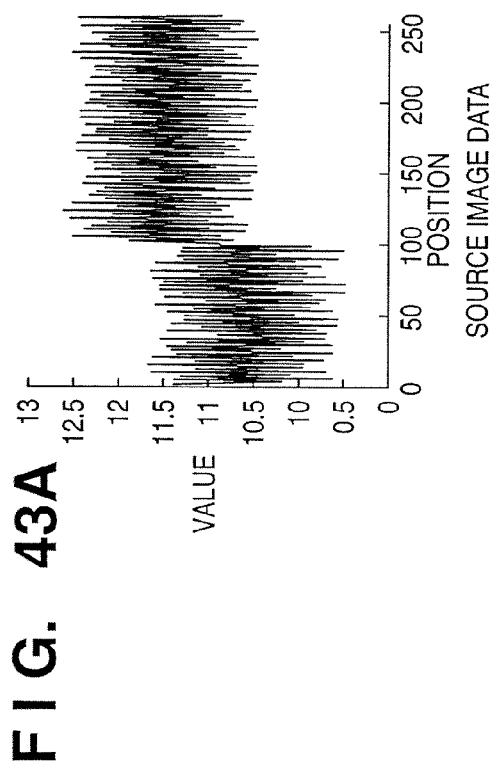
Figure 43C:
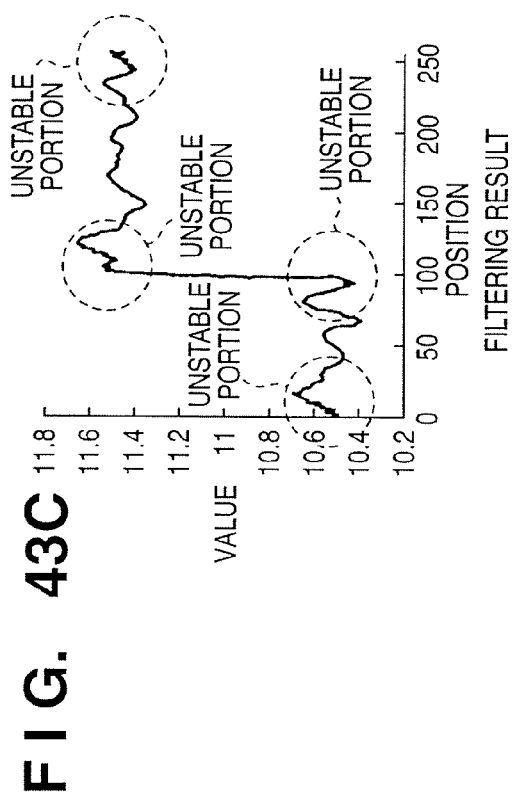

On the other hand, (a) in FIG. 3 indicates the result of filtering having the coefficients (−a3, 0, a3) of the solution given by equation (3) for the image signal shown in FIG. 43A.

Waveforms (bold waveforms) indicated by (b) in FIGS. 2 and 3 indicate envelopes obtained by calculating the square roots of the square sums of results of filtering having the coefficients (−a3, 0, a3) of the solution given by equation (3) for source image signals indicated by (a) in FIGS. 2 and 3 and the source image signals.

Especially, paying attention to a concave portion indicated by (c) in FIG. 3 in the envelope indicated by (b) in FIG. 3, unsteady components are apparently present in that concave portion. This means that the extracted grid stripe components are abnormally extracted by simple filtering (to contain edge components and the like of the objective image), and if such components are subtracted from the objective image signal, artifacts are generated in the processed objective image signal.

Hence, in this embodiment, a range that indicates abnormal numerical values is specified from the envelope obtained by the aforementioned calculation, and grid stripe components within that range are corrected (substituted) by an estimated value from a surrounding numerical value string. In other words, by exploiting a nature that grid stripe components always have steady components over the entire range as a feature of the grid stripe components, the grid stripe components are formed (generated).

The estimated value (predicted value) used in correction is obtained from a statistical nature of data around the range that indicates abnormal numerical values. For example, since the spatial frequency fm of the grid stripe components is known, this spatial frequency fm can be used as the statistical nature.

For example, grid stripe components of an unsteady portion are formed using a sine wave given by:

$$f(x) = A\cos(2\pi fmx - \phi) \quad (4)$$

on the basis of the spatial frequency fm and phase $\phi$ of grid stripes.

For example, as the simplest method, a method of obtaining two coefficients A and $\phi$ at a specific frequency from surrounding pixels using Fourier transformation (Fourier series expansion) is known.

However, due to a program of, e.g., the presence of defects (unsteady portions) in data, normal Fourier transformation cannot be used. Therefore, Fourier transformation is generalized in this case, and the amplitude and phase information are obtained in the sense of least square. For this purpose, equation (4) is modified to:

$$f(x) = R\cos(2\pi fmx) + I\sin(2\pi fmx) \; A = \sqrt{R^2 + I^2} \; \phi = \tan^{-1}(I/R) \quad (5)$$

In this case, a square error $\epsilon$ obtained when data at a sampling point xi is "yi" (data length n) ({xi, yi; i=0 to n−1}) is given by:

$$\varepsilon = \sum_{i=0}^{n-1} ((R\cos(2\pi fmxi) + I\sin(2\pi fmxi) - yi)^2) \quad (6)$$

Note that only data which are determined to be steady portions from verification of components of the envelope must be selected as components "xi, yi" used in this equation. Parameters R and I that minimize the square error $\epsilon$ are obtained as follows.

First, equations (7):

$$\frac{\partial \varepsilon}{\partial R} = 2\sum_{i=1}^{n-1} ((R\cos(2\pi fmxi) + I\sin(2\pi fmxi) - yi)\cos(2\pi fmxi)) = 0 \quad (7)$$

$$\frac{\partial \varepsilon}{\partial I} = 2\sum_{i=0}^{n-1} ((R\cos(2\pi fmxi) + I\sin(2\pi fmxi) - yi)\sin(2\pi fmxi)) = 0$$

are rewritten as:

$$\begin{bmatrix} \sum_{i=0}^{n-1}\cos^2(2\pi fmxi) & \sum_{i=0}^{n-1}\cos(2\pi fmxi)\sin(2\pi fmxi) \\ \sum_{i=0}^{n-1}\cos(2\pi fmxi)\sin(2\pi fmxi) & \sum_{i=0}^{n-1}\cos^2(2\pi fmxi) \end{bmatrix} \begin{bmatrix} R \\ I \end{bmatrix} = \begin{bmatrix} \sum_{i=0}^{n-1} yi\cos(2\pi fmxi) \\ \sum_{i=0}^{n-1} yi\sin(2\pi fmxi) \end{bmatrix} \quad (7')$$

$$\frac{1}{2}\begin{bmatrix} \sum_{i=0}^{n-1}(1+\cos(4\pi fmxi)) & \sum_{i=0}^{n-1}(\sin(4\pi fmxi)) \\ \sum_{i=0}^{n-1}(\sin(4\pi fmxi)) & \sum_{i=0}^{n-1}(1-\cos(4\pi fmxi)) \end{bmatrix}\begin{bmatrix} R \\ I \end{bmatrix} = \begin{bmatrix} \sum_{i=0}^{n-1} yi\cos(2\pi fmxi) \\ \sum_{i=0}^{n-1} yi\sin(2\pi fmxi) \end{bmatrix}$$

$$\frac{1}{2}\left(\begin{bmatrix} n & 0 \\ 0 & n \end{bmatrix} + \begin{bmatrix} \sum_{i=0}^{n-1}\cos(4\pi fmxi) & \sum_{i=0}^{n-1}\sin(4\pi fmxi) \\ \sum_{i=0}^{n-1}\sin(4\pi fmxi) & \sum_{i=0}^{n-1}\cos(4\pi fmxi) \end{bmatrix}\right)\begin{bmatrix} R \\ I \end{bmatrix} = \begin{bmatrix} \sum_{i=0}^{n-1} yi\cos(2\pi fmxi) \\ \sum_{i=0}^{n-1} yi\sin(2\pi fmxi) \end{bmatrix}$$

Solving simultaneous equations of equations (7') above can yield parameters R and I, and phase φ and amplitude A can be simultaneously estimated.

If a data sequence divides a section k/(2·fm) into m equal sections, equations (7') become discrete Fourier transformation (Fourier series expansion) that obtains coefficients at a specific frequency, as given by:

$$\frac{1}{2}\begin{bmatrix} n & 0 \\ 0 & n \end{bmatrix}\begin{bmatrix} R \\ I \end{bmatrix} = \begin{bmatrix} \sum_{i=0}^{n-1} yi\cos(2\pi fmxi) \\ \sum_{i=0}^{n-1} yi\sin(2\pi fmxi) \end{bmatrix} \quad (8)$$

By calculating the values of parameters R and I using appropriate steady data around the unsteady portion by equations (7') or equation (8), the unsteady portion which is removed as an inappropriate portion is patched (substituted).

As another patch method, a method of sequentially predicting and patching based on a linear prediction algorithm without specifying the spatial frequency of grid stripes in consideration of a linear prediction model may be used.

The signal waveform obtained by the aforementioned patch process is normally a steady sine wave, and consists of components which express grid stripe components very well.

However, the signal waveform (that of grid stripe components) is obtained as a result of FIR filtering in a short span using the coefficients (a1, b1, a1) given by equation (2), has the filter response characteristics shown in FIG. 1, and contains many image components other than the grid stripe components.

Hence, in this embodiment, the signal waveform undergoes filtering for extracting components in the neighborhood of the spatial frequency fm of the grid stripes. This filtering is applied to the components, the unsteady components of which have already been patched by the aforementioned operation, and never generates any artifacts such as ringing or the like.

Upon generating the envelope of the signal of the grid stripe components after filtering, if a portion where a very small value (a value nearly equal to "0") is observed is present, this portion is a portion where grid stripe components are not observed for some reasons (e.g., X-rays are perfectly intercepted, the sensor has been saturated, and so forth), and no grid stripe components are present originally. Hence, the information of this portion is recorded, and is replaced by "0" after subsequent filtering. The result of this process is subtracted as grid stripe components from the objective image signal.

In this embodiment, the grid stripe component extraction process is executed while reading out line data to be processed from the objective image signal line by line. In this case, upon reading out one line data, the average of several line data before and after the line data of interest may be calculated to weaken image components or to emphasize grid stripe components, and the grid stripe components may be extracted.

This is because the direction of grid stripes is nearly parallel to the line-up direction of pixels on the sensor, and grid stripe components of a given line are very similar to those of nearby lines.

Therefore, as another embodiment of this embodiment, using the feature of very high similarity, lines to be processed are decimated to reduce the number of times of calculation processes required to extract the grid stripe components, and grid stripe components extracted from a given line are used as those of nearby lines. That is, a grid stripe component extraction process is skipped for lines near the line from which the grid stripe components have been extracted, and a subtraction process from nearby line data can be executed using the grid stripe components extracted from the line.

In order to check if the aforementioned decimation process is allowed, upon measuring the spatial frequency of grid stripes in the first processing step, the phase difference of grid stripes between lines before and after the sampled line or between sampled lines is checked to confirm that the direction of grid stripes is not inclined with respect to the line-up direction of pixels of the sensor.

Also, as still another embodiment of this embodiment, when the grid stripe components are removed from the objective image signal, the irradiation field of the objective image signal may be recognized by detecting the signal strength or the like, and only image data within the irradiation field may undergo the grid stripe component removal process.

For example, when an X-ray image is captured by a solid-state image sensing element, a problem of defective pixels is posed as that unique to the solid-state image sensing element formed by arranging a plurality of pixels. Owing to the redundancy of image information (containing spatially low-frequency components as major components), if the number of defective pixels is negligibly small, defective pixels can normally be patched (corrected) by interpolation using the average of surrounding pixel values.

However, in general, prediction is required due to a statistical nature around defective pixels. For example, when the spatial frequency of the grid stripes is equal to or higher than 50% of the Nyquist frequency as in this embodiment, the prediction result may be reversed by average interpolation.

Figure 4:
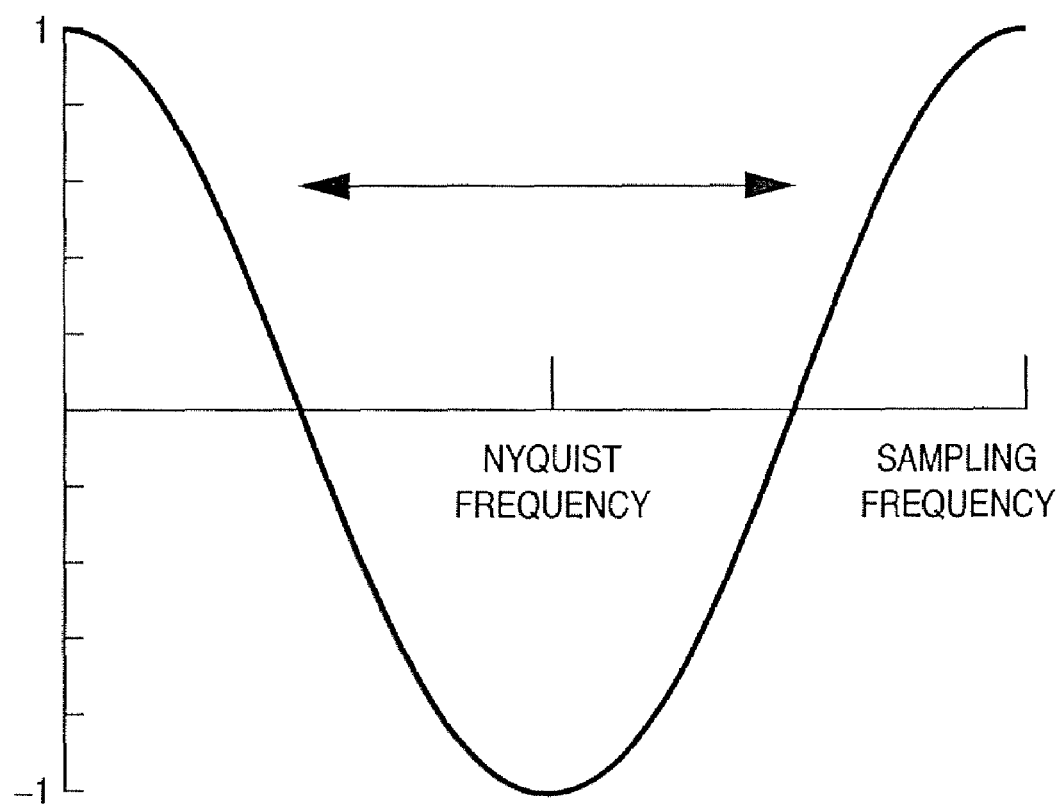
FIG. 4 is a graph for explaining the spatial frequency characteristics in defective pixel correction of an objective image.

FIG. 4 shows a response function as filtering when a defective pixel is present at an arbitrary point in one dimension, and is interpolated using the average of its two neighboring pixels.

In FIG. 4, the abscissa plots the spatial frequency. As shown in FIG. 4, if the spatial frequency is low and is equal to or lower than 50% of the Nyquist frequency, a response is "positive", i.e., no phase inversion occurs. By contrast, if the spatial frequency is equal to or higher than 50% of the Nyquist frequency, the phase is inverted, and an expected interpolation result cannot be obtained.

Figure 5:
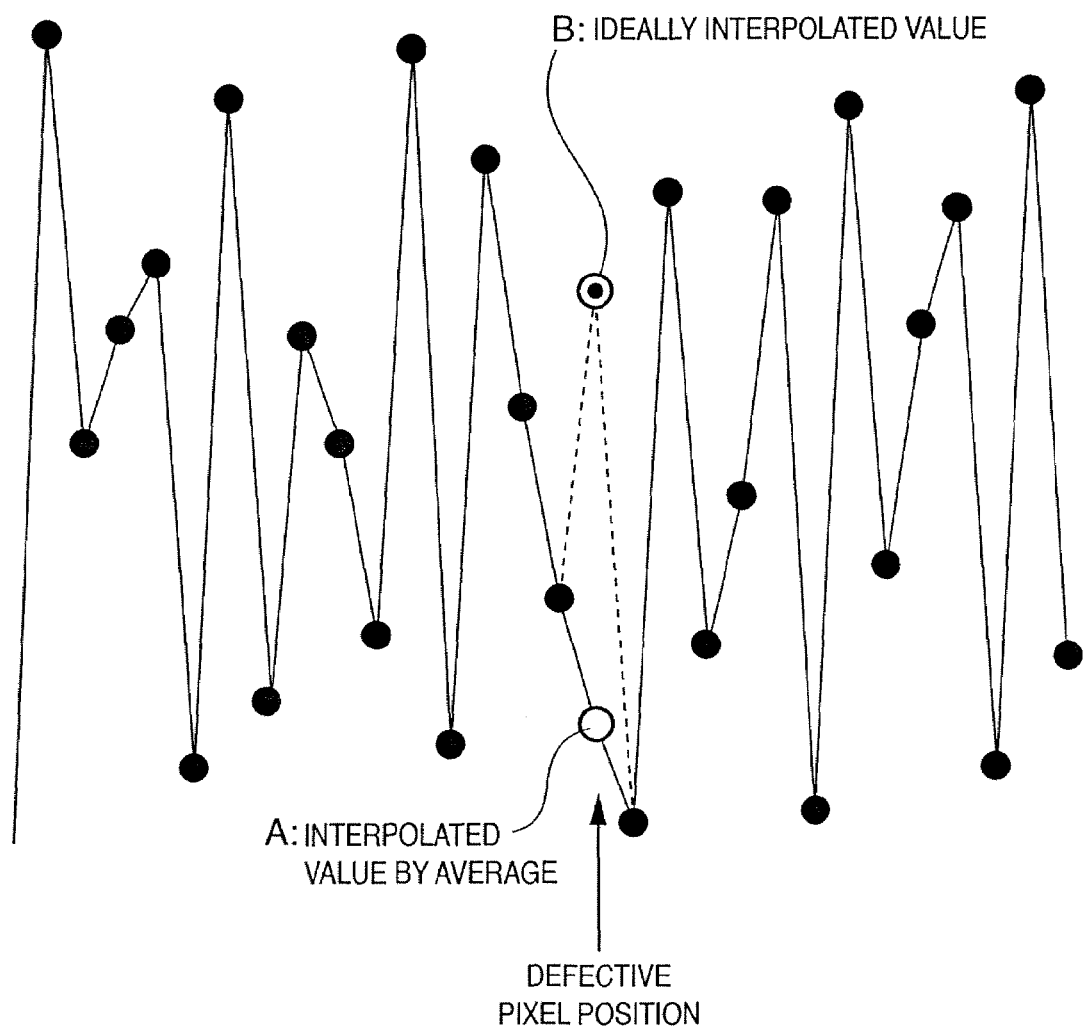
FIG. 5 is a view for explaining the spatial frequency characteristics in defective pixel correction for an object image including the grid stripe components.

FIG. 5 shows an example of defective pixel interpolation.

In FIG. 5, each black dot indicates a pixel value obtained from a normal pixel, and a dot indicated by an arrow ("defective pixel position") indicates a defective pixel where no data is obtained. FIG. 5 illustrates a state wherein respective pixel data (data indicated by black dots) oscillate finely since grid stripes are superposed.

A white dot indicated by "A: interpolated value by average" in FIG. 5 is a pixel value obtained by conventional average interpolation, and a white dot indicated by "B: ideally interpolated value" in FIG. 5 is a pixel value that takes grid stripes into consideration.

In this embodiment, in order to obtain an ideal interpolated value indicated by "B: ideally interpolated value" in FIG. 5, the following two methods are executed.

(Method 1: Linear Prediction Method)

In FIG. 5, data at the defective pixel position is obtained by linear prediction from surrounding pixel values.

(Method 2)

After major components equal to or lower than 50% of the Nyquist frequency are removed by removing grid stripe components from the source image signal by the aforementioned grid stripe removal process, an interpolation process based on the average as the conventional method is executed.

An outline of the linear prediction method as (method 1) will be described below.

As image data (pixel data) to be processed, data sequence $\{X_n, X_{n-1}, X_{n-2}, \ldots, X_{n-p}\}$ is given, and data $X_n$ at "n" is given by a differential equation:

$$X_n = \epsilon_n - a_1 X_{n-1} - a_2 X_{n-2} - a_3 X_{n-3} - \ldots - a_p X_{n-p} \quad (9)$$

where "$\epsilon_n$" is a white noise sequence, and "$a_i$ $\{i=1, \ldots, p\}$" is a linear prediction coefficient. Such sequence is called an "autoregressive process (AR process) $X_n$".

Equation (9) is rewritten using a delay operator $Z^{-1}$ as:

$$A(Z^{-1})X_n = \epsilon_n \quad (10)$$

However, since equation (10) is expressed by:

$$A(Z^{-1}) = 1 + a_1 Z^{-1} + a_2 Z^{-2} + a_3 Z^{-3} \ldots + a_p Z^{-p} \quad (10')$$

the AR process $X_n$ can be defined (spectrally estimated) as the output in response to the input $\epsilon_n$ of a linear filter having a pulse transfer function $1/A(Z^{-1})$.

Equation (9) reveals that n-th pixel data can be predicted from (n−1)-th pixel data if the linear prediction coefficient $a_i$ $\{i=1, \ldots, p\}$ is obtained from a reliable data sequence.

The linear prediction coefficient $a_i$ $\{i=1, \ldots, p\}$ can be predicted using most likelihood estimation (least square estimation) under the condition that the apparatus or system is steady. That is, a coefficient which minimizes the power (variance) of $\epsilon_n$ can be obtained. Since $\epsilon_n$ is an error obtained by least square estimation, it has no correlation components less than its prediction order.

Therefore, the prediction error $\epsilon_n$ obtained by estimation with necessary and sufficient order p becomes white noise, as defined by equation (9).

Since the variance of prediction error $\epsilon_n$ is a square mean (mean value="0"), a function E[*] that express the mean is given by:

$$\begin{aligned} E[\varepsilon_n^2] &= E\left[\left(X_n + \sum_{k=1}^{p} a_k X_{n-k}\right)^2\right] \\ &= E\left[X_n^2 + 2\sum_{k=1}^{p} a_k X_n X_{n-k} + \left(\sum_{k=1}^{p} a_k X_{n-k}\right)\left(\sum_{j=1}^{p} a_j X_{n-j}\right)\right] \\ &= R(0) + 2\sum_{k=1}^{p} R(k) + \sum_{k=1}^{p}\sum_{j=1}^{p} a_k a_j R(k-j) \end{aligned} \quad (11)$$

In equation (11), $$R(\tau) = E[X_m X_{m+\tau}] \text{ (covariance)}$$

and in order to obtain a minimum value, equating both the sides to zero by differentiation using a coefficient $a_k$ yields simultaneous equations:

$$R(k) + \sum_{j=1}^{p} a_k R(k-j) = 0, \quad k = 1, L, p \quad (12)$$

These equations are called normal equations or Yule-Walker equations.

In practice, autocorrelation R(*) is not calculated at all pixel points, but an estimated value calculated using limited (given) pixels is used instead.

For example, the Levinson algorithm as a high-speed calculation method is used, but the Burg algorithm may be used. This Burg algorithm is based on a maximum entropy method with which covariance (autocorrelation) can be obtained using fewer pixel data without directly calculating it. In such algorithms, if the prediction errors form a normal distribution, and the number of pixels is large, their results mathematically match. However, if the number of pixels is small, the Burg algorithm (based on the maximum entropy method) is advantageous.

Using the coefficient $a_k$ obtained by the aforementioned calculation, predicted pixel data is obtained from pixels before and after a defective pixel.

First Embodiment

Figure 6:
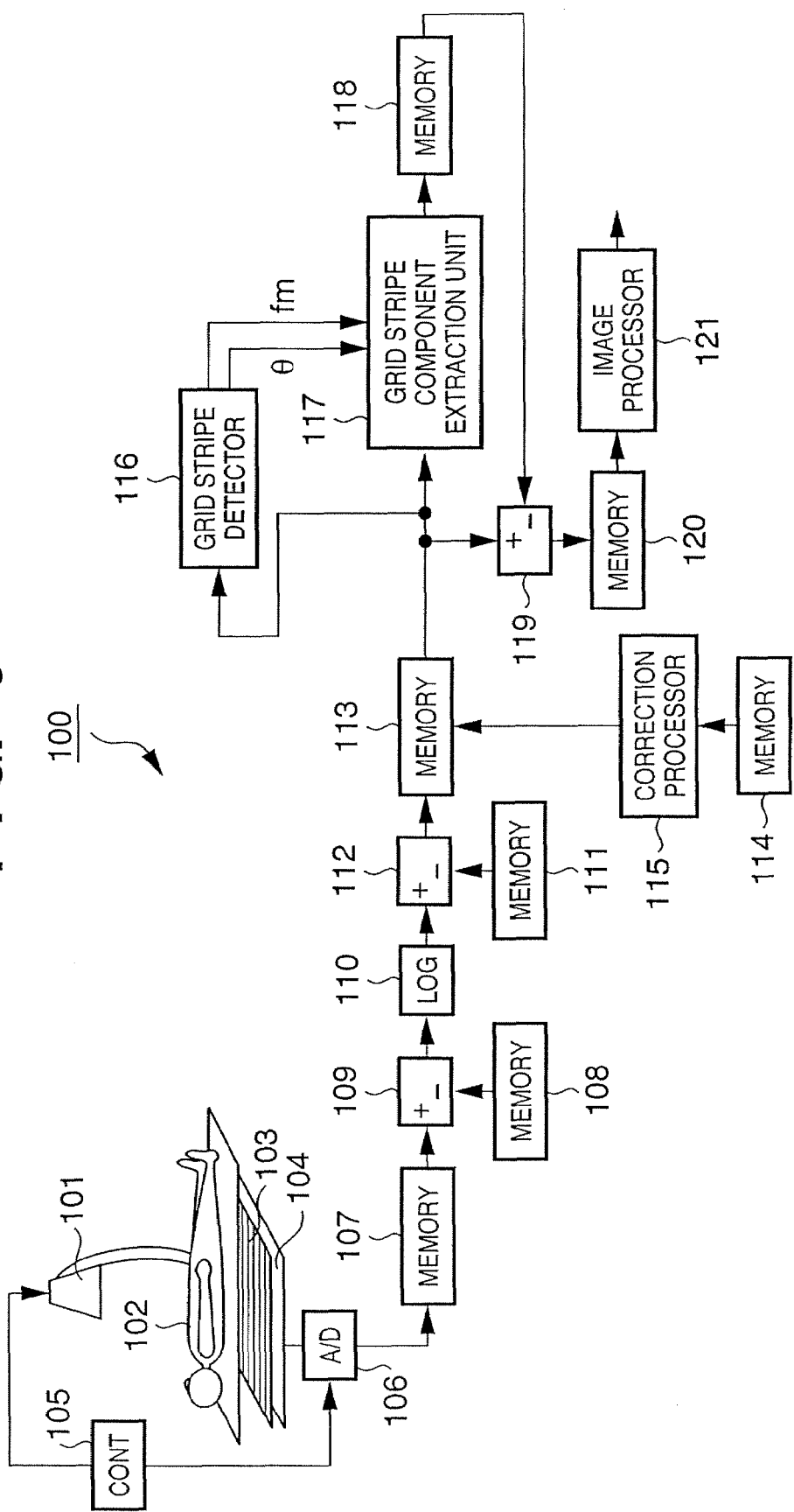
FIG. 6 is a block diagram showing the arrangement of an X-ray image capture apparatus to which the present invention is applied in the first embodiment.

The present invention is applied to, e.g., an X-ray image capture apparatus 100 shown in FIG. 6.

<Overall Arrangement and Operation of X-ray Image Capture Apparatus 100>

The X-ray image capture apparatus 100 of this embodiment is used to capture an X-ray image for medical use (for image diagnosis or the like), and comprises an X-ray generator 101 for generating X-rays toward an object 102 (human body in this case), a grid 103 for removing scattered X-rays from the object 102, a flat X-ray sensor 104 for detecting the distribution of the X-ray dose that has been transmitted through the object 102, a controller 105 (CONT) of the X-ray generator 101, and an analog/digital (A/D) converter 106 for converting an electrical signal output from the X-ray sensor 104 into digital data, as shown in FIG. 6.

The apparatus 100 also comprises a memory 107 for temporarily storing digital data output from the A/D converter 106 as objective image data, a memory 108 for storing data captured while no X-rays are generated, an arithmetic device 109 for executing an arithmetic process of the objective image data in the memory 107 using the data in the memory 108, and a conversion table (to be also referred to as an "LUT" (lookup table) hereinafter) 110 of the objective image data that has undergone the arithmetic process in the arithmetic device 109.

The apparatus 100 further comprises a memory 111 for storing gain pattern data used to correct variations of gains for respective pixels that form the X-ray sensor 104, an arithmetic device 112 for executing an arithmetic process of the converted objective image data output from the LUT 110 using the gain pattern data in the memory 111, and a memory 113 for temporarily storing the objective image data that has undergone the arithmetic process in the arithmetic device 112.

The apparatus 100 further comprises a memory 114 for storing information (defective pixel position information and the like) associated with defective pixels unique to the X-ray sensor 104, a correction processor 115 for executing a correction process of the objective image data stored in the memory 113 using the information in the memory 114, and a grid stripe detector 116 for detecting information associated with grid stripes from the objective image data in the memory 113 after the correction process.

The apparatus 100 further comprises a grid stripe component extraction unit 117 for extracting grid stripe components from the objective image data in the memory 113 after the correction process on the basis of the information obtained by the grid stripe detector 116, and a memory 118 for temporarily storing the grid stripe components extracted by the grid stripe component extraction unit 117.

The apparatus 100 further comprises an arithmetic device 119 for subtracting the grid stripe components in the memory 118 from the objective image data in the memory 113 after the correction process, a memory 120 for temporarily storing the arithmetic result of the arithmetic device 119 (the objective image data after the grid stripe components are removed), and an image processor 121 for executing an image process of the objective image data in the memory 120 and outputting the processed image data.

In the aforementioned X-ray image capture apparatus 100, the controller 105 of the X-ray generator 101 controls the X-ray generator 101 to start X-ray radiation in response to a generation trigger which is input by an operator at a console (not shown).

The X-ray generator 101 irradiates the object 102 as a human body with X-rays.

X-rays emitted by the X-ray generator 101 are transmitted through the object 102, and reach the X-ray sensor 104 via the grid 103 which remove scattered X-rays from the object 102.

The X-ray sensor 104 has a matrix of a plurality of detectors (pixels) for detecting X-ray intensities on a surface (image-receiving surface) that detects the distribution of the X-ray dose which has been transmitted through the object 102, and outputs electrical signals corresponding to X-ray intensities obtained by the plurality of detectors (pixels) in the matrix.

As the X-ray sensor 104, for example, sensors (1) and (2) to be described below may be applied.

Sensor (1):
a sensor which temporarily converts the X-ray intensity into fluorescence, and detects the fluorescence by photoelectrically converting it using a plurality of detectors arranged in a matrix.

Sensor (2):
a sensor which forms a charge distribution by attracting free electrons liberated upon photoelectric conversion of X-rays in a specific object, with which the object is irradiated, and converts the charge distribution into electrical signals by a plurality of charge detectors (capacitors) arranged in a matrix.

The A/D converter 106 converts electrical signals output from the X-ray sensor 104 into digital data, and outputs the digital data.

More specifically, the A/D converter 106 sequentially converts electrical signals output from the X-ray sensor 104 into digital data and outputs them in synchronism with X-ray radiation by the X-ray generator 101 or driving of the X-ray sensor 104.

In FIG. 6, one A/D converter 106 is arranged. For example, a plurality of A/D converters may be arranged and may operate parallelly. With this arrangement, a high digital conversion speed is assured, and an efficient process can be done.

Digital data output from the A/D converter 106 is temporarily stored in the memory 107 as objective image data.

Therefore, the memory 107 stores digital image data (objective image data) as a set of a plurality of pixel data corresponding to a plurality of pixels which form the X-ray sensor 104.

The memory 108 pre-stores digital data which is acquired by photographing while quitting X-ray radiation. This digital data is used to remove offset-like fixed pattern noise unique to the X-ray sensor 104 from the objective image data stored in the memory 107. Therefore, the X-ray image capture apparatus 100 captures an image while controlling the X-ray generator 101 not to generate X-rays, and stores the captured digital data in the memory 108 as image data.

The arithmetic device 109 executes a process for subtracting pixel data at a given position among a plurality of pixel data which form the image data (image data of fixed pattern noise obtained by photographing without X-ray radiation) stored in the memory 108 from a corresponding one of a plurality of pixel data which form the objective image data (which is obtained by X-rays transmitted through the object 102) stored in the memory 107.

The LUT 110 converts the objective image data that has been processed by the arithmetic device 109 into values proportional to its logarithmic values, and outputs the converted data.

The memory 111 stores gain pattern data used to correct gain variations of pixels which form the X-ray sensor 104 for the objective image data that has been converted by the LUT 110. For this purpose, the X-ray image capture apparatus 100 makes X-ray radiography without any object 102, removes fixed pattern noise from the image data obtained by that photographing using the digital data stored in the memory 108, and stores data obtained by converting that data into values proportional to logarithmic values by the LUT 110 in the memory 111 as gain pattern data.

The arithmetic device 112 subtracts the gain pattern data in the memory 111 from the objective image data output from the LUT 110 (this process corresponds to division if data to be processed is not logarithmically converted), and outputs the difference data.

The objective image data that has undergone the subtraction process by the arithmetic device 112 is temporarily stored in the memory 113.

Upon acquiring image data used as gain pattern data to be stored in the memory 111, if photographing is made while the grid 103 is attached, grid stripes are superimposed on the gain pattern data itself obtained by that photographing. It is expected that grid stripe components may be removed upon subtracting the gain pattern data from the objective image data by the arithmetic device 112 since the grid stripes themselves superimposed on the object 102 are approximate to gain variations.

However, it is unlikely that gain pattern data is acquired every image capture (every actual photographing) by photographing without any object 102. In most cases, gain pattern data is acquired at a frequency of once per day or lower. As the positional relationship between the X-ray generator 101 and X-ray sensor 104 may change every photographing, grid stripe components are not removed by the aforementioned subtraction process.

Even when the positional relationship remains the same, since photographing processes with and without the object 102 have different scattered X-ray quantities and qualities, grid stripes have different contrasts and grid stripe components are not removed by the subtraction process. Note that, in either case, the spatial frequency of grid stripes never varies as long as the directions of the grid 103 agree with each other. It is preferable to detach the grid 103 itself upon acquiring the gain pattern data, so that the gain pattern data does not contain any grid stripes.

The memory 114 stores information (defective pixel position information and the like) that pertains to defective pixels unique to the X-ray sensor 104.

More specifically, a flat X-ray sensor is normally manufactured by the semiconductor manufacturing technique, but its yield is not 100%. Hence, some of a plurality of detectors (pixels) are defective pixels which do not have a detector function, i.e., whose outputs are insignificant. In this case, the X-ray sensor 104 is inspected in advance in the manufacturing process or by an arbitrary means (not shown), and the position information of each of defective pixels obtained by inspection is stored in the memory 114.

The correction processor 115 corrects defective pixel data in a plurality of pixel data which form the objective image data stored in the memory 113 using the defective pixel position information stored in the memory 114, and stores the corrected pixel data at corresponding locations of the memory 113 again.

The grid stripe detector 116 analyzes grid stripes for the objective image data in the memory 113 (image data that has undergone the correction process by the correction processor 115), and detects and outputs the spatial frequency fm and the angle θ of grid stripes.

The grid stripe component extraction unit 117 reads out the objective image data in the memory 113 (image data that has undergone the correction process by the correction processor 115), and extracts grid stripe components from the readout image data on the basis of the spatial frequency fm and angle θ of grid stripes obtained by the grid stripe detector 116.

The grid stripe components extracted by the grid stripe component extraction unit 117 are temporarily stored in the memory 118.

The arithmetic device 119 subtracts the grid stripe components stored in the memory 118 from the objective image data in the memory 113 (image data that has undergone the correction process by the correction processor 115).

The objective image data after the grid stripe components are subtracted by the arithmetic device 119 is temporarily stored in the memory 120.

The image processor 121 executes an image process of the objective image data in the memory 120 to allow easy observation of the observer.

Note that the image process includes, for example, the following processes:
- a removal process of random noise from an objective image;
- a process for converting tone or emphasizing details to obtain density values that are easy to see for the observer upon displaying an objective image; and
- a process for reducing the information size of an objective image by cutting out a portion unnecessary for the observer from an objective image, or compressing objective image information.

The objective image data that has been processed by the image processor 121 then undergoes a display process on a display unit, a storage process in a storage unit or storage medium, an analysis process, or the like by arbitrary means (not shown) in an external apparatus or the X-ray image capture apparatus 100.

<Detailed Arrangement and Operation of X-ray Image Capture Apparatus 100>

The following building components which require detailed descriptions in the aforementioned X-ray image capture apparatus 100 will be described in detail below.

(1) Image data of grid stripe components stored in memory 118

(2) Correction process of defective pixels by correction processor 115

(3) Detection & extraction processes of grid stripe components by grid stripe detector 116 and grid stripe component extraction unit 117

(1) Image Data of Grid Stripe Components Stored in Memory 118

The image data of grid stripe components stored in the memory 118 is to be subtracted from the objective image data on which grid stripe components are superposed. If the data stored in the memory 118 is separately stored in correspondence with the objective image data after subtraction like in this embodiment, the source objective image data on which grid stripe components are superposed can be recovered from the objective image data from which grid stripes have been removed. In this way, even when the objective image data is damaged by some troubles in a grid removal process, the source objective image data can be recovered by the recovery process.

(2) Correction Process of Defective Pixels by Correction Processor 115

The correction processor 115 executes a process to be described below by, e.g., software using a microprocessor.

FIGS. 7 to 10 show examples of pixel defect distributions in the X-ray sensor 104.

Assume that each pixel defect is basically present to have only a width of one pixel. This is because an X-ray sensor having a plurality of neighboring pixel defects as a large mass is not used normally since it is difficult to patch defective pixels.

In each of FIGS. 7 to 10, each square indicates a pixel, and a black square indicates a defective pixel. Also, the direction of grid stripes (vertical direction) is indicated below each figure.

Figure 7:
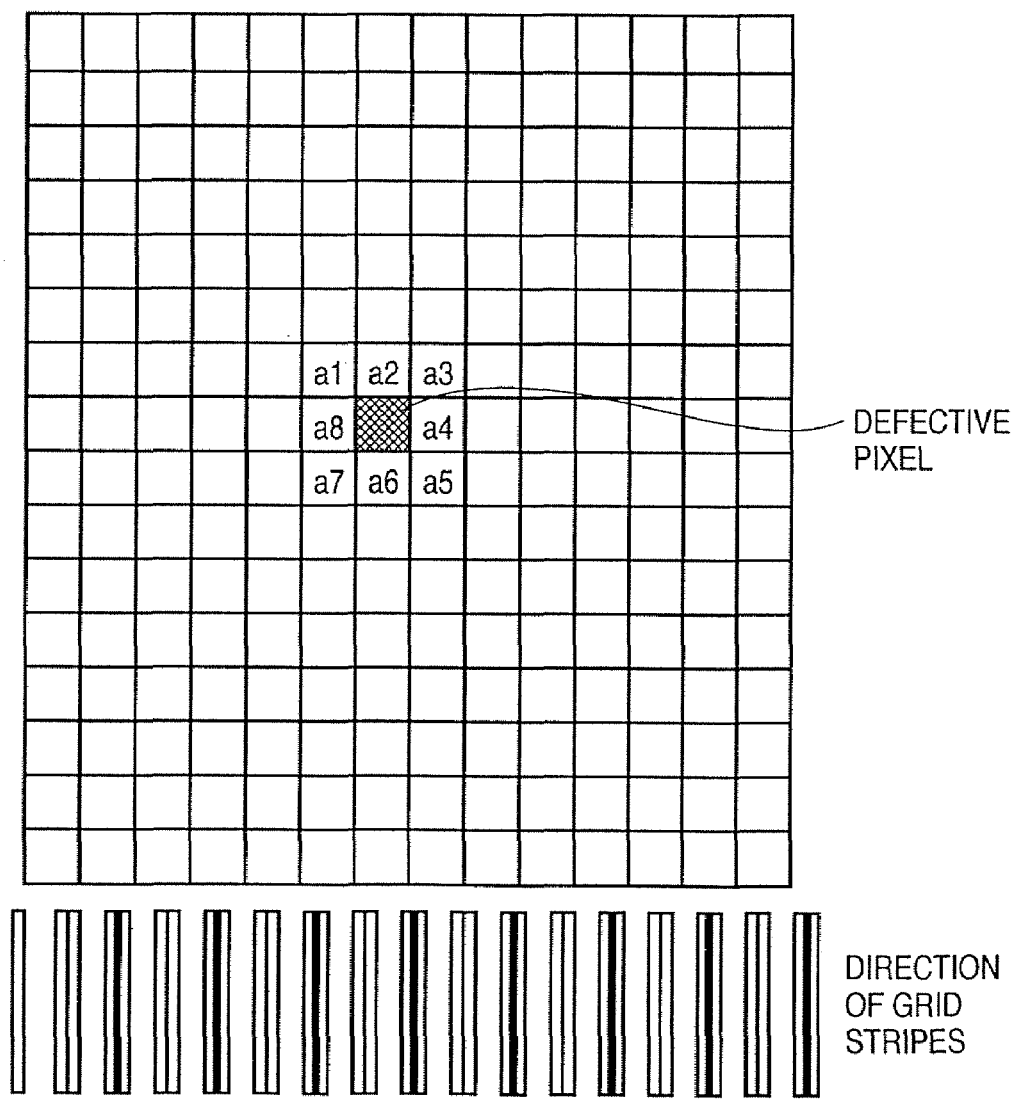
FIG. 7 is a view for explaining an example (example 1) of a defective pixel state in an objective image of the X-ray image capture apparatus.

A defective pixel shown in FIG. 7 is a basic one, and eight neighboring pixel components a1 to a8 are present around the defective pixel (black square), as shown in FIG. 7.

Figure 11:
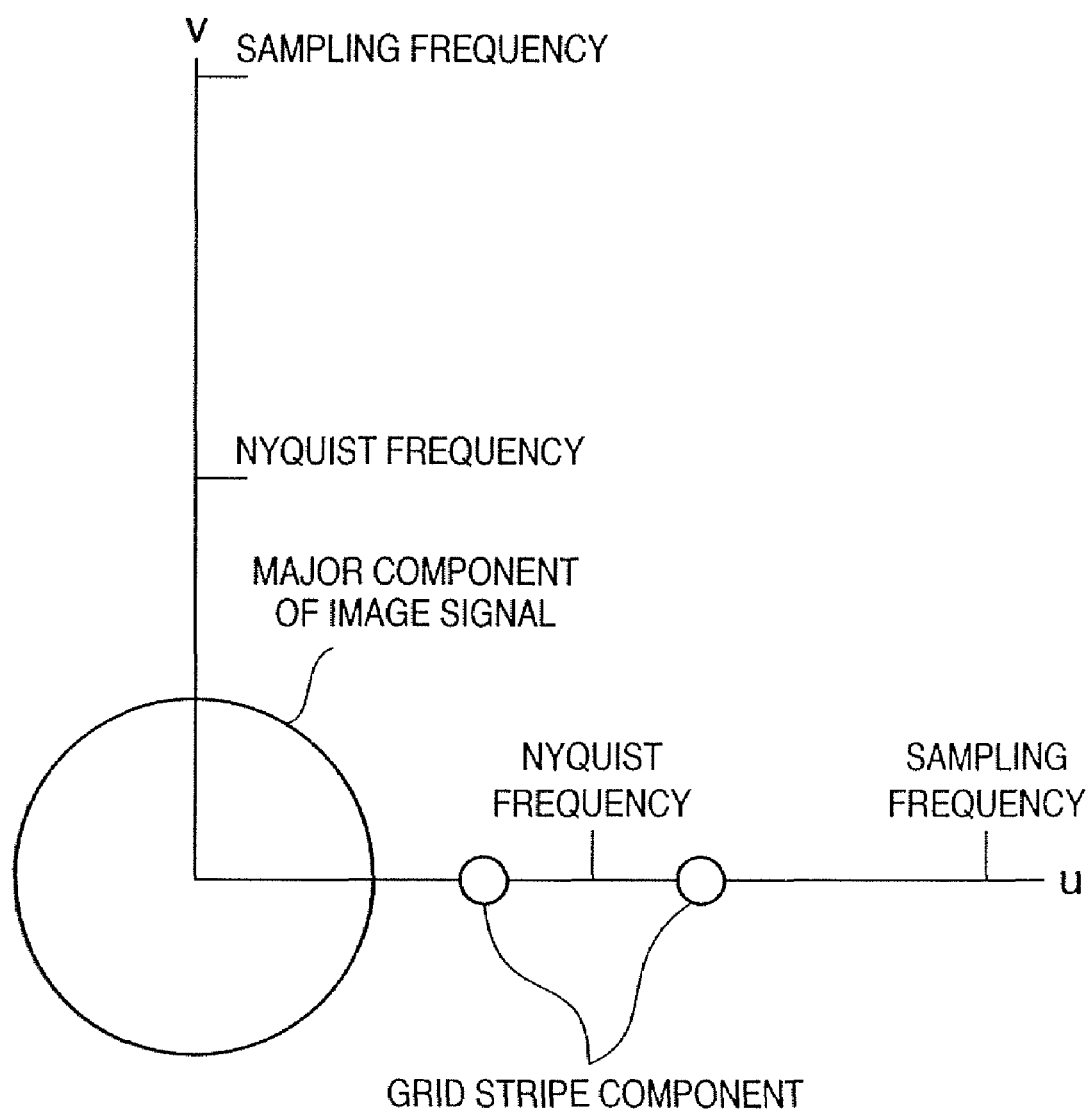
FIG. 11 is a view for explaining the spatial frequency distribution of grid stripe components in an objective image of the X-ray image capture apparatus.

FIG. 11 illustrates the signal distribution of grid stripe components on the spatial frequency axis in an objective image which includes the defective pixel shown in FIG. 7 and the grid stripe components.

Referring to FIG. 11, the abscissa represents a horizontal spatial frequency axis u of the objective image, the ordinate represents a vertical spatial frequency axis v of the objective image, and both the spatial frequency axes u and v plot "sampling frequency" as the reciprocal of the pixel pitch and "Nyquist frequency" as a half value of that frequency.

Since the grid stripes oscillate in the horizontal direction of the objective image, and are constant in the vertical direction, grid stripe components are present on the spatial frequency axis u (see white dots in FIG. 11), as shown in FIG. 11.

In a normal image, its major components are distributed in the spatial frequency domain equal to or smaller than the half value of the Nyquist frequency, and if no grid stripe components are present, a defective pixel value can be interpolated by the average of arbitrary pixel values on the two sides of the defective pixel. This is because the influence of the interpolation on the spatial spectrum indicates a response function (characteristics) of filtering shown in FIG. 4.

Therefore, in case of correction of the defective pixel shown in FIG. 7, since no grid stripe components are present in the vertical direction, nearly perfect correction can be made by the average of pixels in the vertical direction, i.e., the average of pixel components a2 and a6 or either pixel component.

Figure 8:
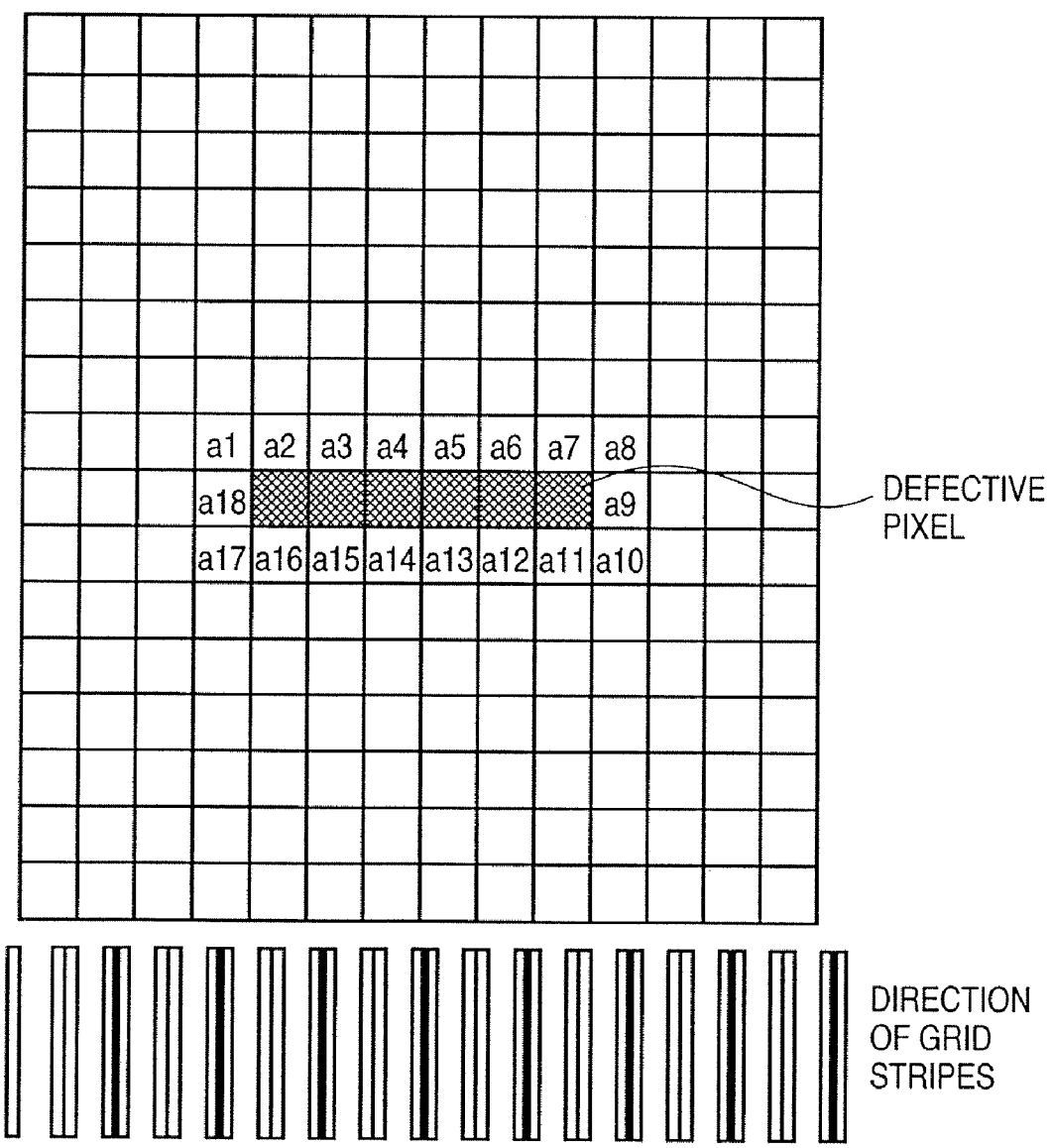
FIG. 8 is a view for explaining another example (example 2) of the defective pixel state.

Defective pixels shown in FIG. 8 are coupled in a horizontally elongated pattern (see black squares in FIG. 8). In case of defective pixels with such pattern as well, since the up-down direction of pixels is parallel to grid stripes, nearly perfect correction can be made by upper and lower neighboring pixel components of the defective pixels to be corrected.

Figure 9:
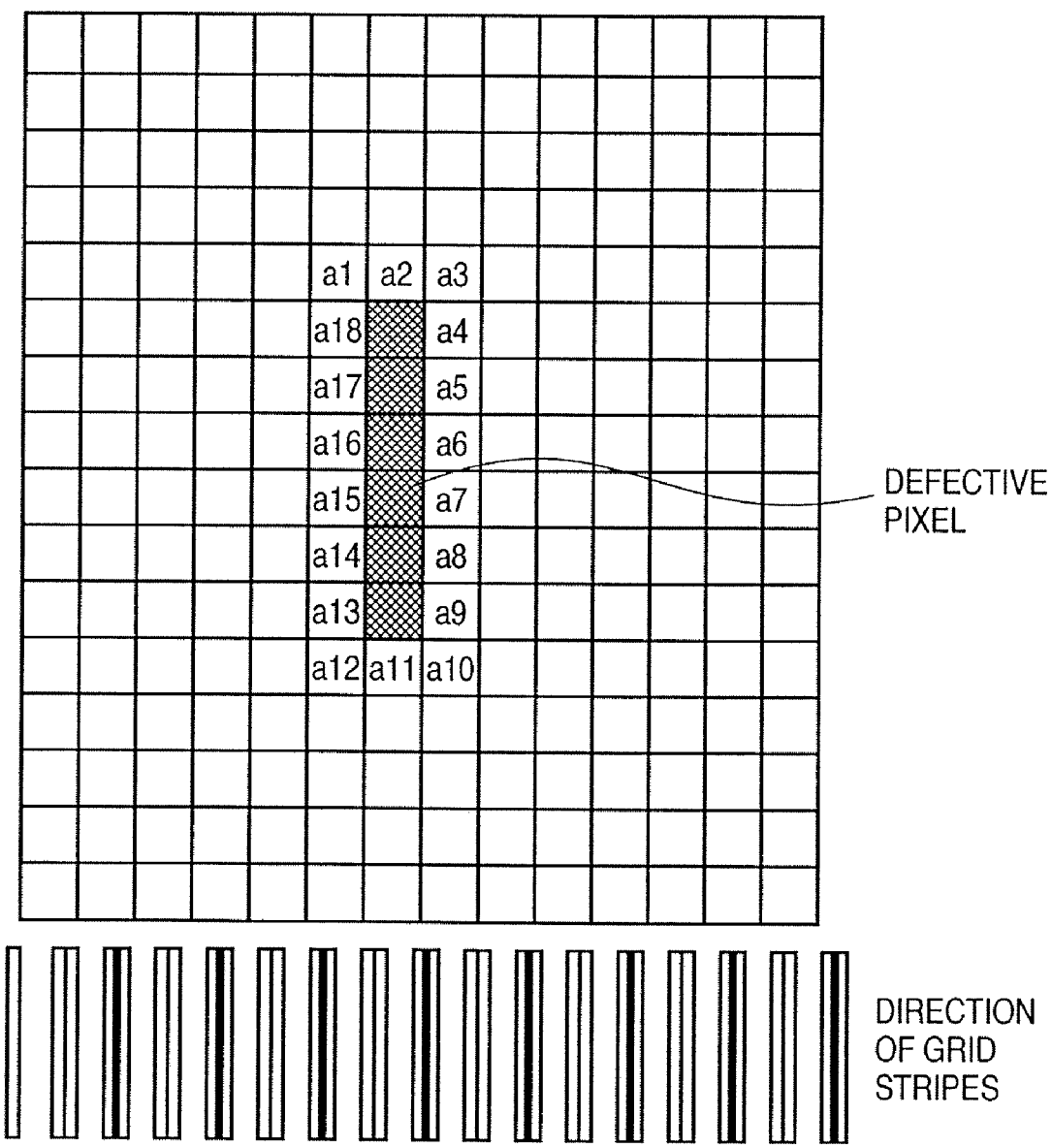
FIG. 9 is a view for explaining still another example (example 3) of the defective pixel state.

Defective pixels shown in FIG. 9 are coupled in a vertically elongated pattern (see black squares in FIG. 9). In case of defective pixels with such pattern, no upper and lower pixels with reliable values neighbor the pixels to be corrected except for the uppermost and lowermost ones of the coupled defective pixels. If defect correction is made for the defective pixels in such state using the simple average in the horizontal direction or the like, a correction result with an unexpected value is obtained, as has been explained previously using FIG. 5.

Hence, in this embodiment, coefficients $a_k$ (k=1 to P) are obtained from right and left neighboring pixels of the defective pixels to be corrected using simultaneous equations (12) using a series of right or left neighboring normal pixel components of each defective pixel to be corrected.

At this time, the number of pixels used is about 20, and order k is around 5.

A defective pixel value $X_n$ of interest is predicted by equation (9) using coefficients $a_k$, and the average of all obtained defective pixel values $X_n$ is calculated. As a result, "B: ideally interpolated value" shown in FIG. 5 is obtained.

In this embodiment, coefficients $a_k$ (k=1 to P) are obtained using equations (12). However, the present invention is not limited to this. For example, an algorithm called a maximum entropy method or the like may be used.

Figure 10:
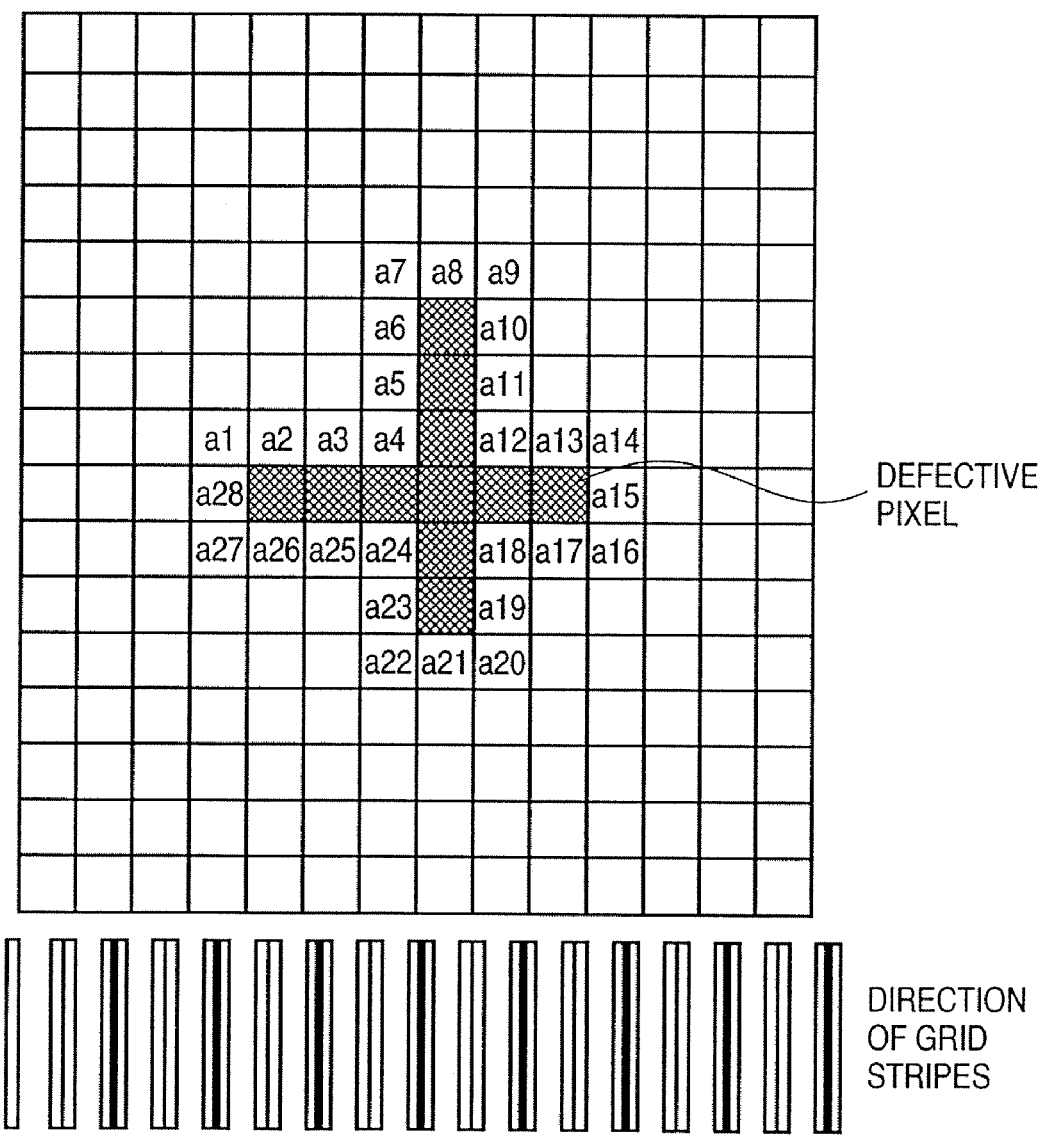
FIG. 10 is a view for explaining still another example (example 4) of the defective pixel state.

Defective pixels shown in FIG. 10 are coupled in a combined pattern of those of the defective pixels shown in FIGS. 8 and 9. A relevant pixel among the defective pixels in this pattern is a pixel at the intersection of the vertically and horizontally coupled defective pixels (a pixel at a position where these defective pixels cross), i.e., a defective pixel surrounded by pixel components a4, a12, a18, and a24.

In the pattern shown in FIG. 10, a series of horizontally coupled defective pixels are corrected using the average of upper and lower neighboring pixel components, and a series of vertically coupled defective pixels are corrected using the simultaneous equations, as described above.

More specifically, the following three methods (a) to (c) are available. However, with any of these methods, nearly the same result is obtained.

(a) The defective pixel surrounded by pixel components a4, a12, a18, and a24 is corrected using the average value of upper and lower neighboring defect correction values (the values of corrected defective pixels).

(b) The defective pixel surrounded by pixel components a4, a12, a18, and a24 is corrected by solving simultaneous equations (12) using the right and left neighboring pixel values as defect correction values.

(c) The defective pixel surrounded by pixel components a4, a12, a18, and a24 is corrected using the average value of the results of the methods (a) and (b).

By executing the aforementioned process, defective pixel data in a plurality of pixel data which form the objective image data stored in the memory 113 can be corrected.

(3) Detection & Extraction Processes of Grid Stripe Components by Grid Stripe Detector 116 and Grid Stripe Component Extraction Unit 117

The grid stripe detector 116 reads out some of the objective image data stored in the memory 113, checks the spectrum of grid stripes contained in the objective image data based on the readout data, and detects the spatial frequency fm and angle θ of the grid stripes. The subsequent grid stripe component extraction unit 117 uses the information of the spatial frequency fm and angle θ (to be also referred to as "angle η" hereinafter) of the grid stripes in a grid stripe component extraction process.

FIGS. 12A to 12D are views for explaining the detection process of the spatial frequency fm and angle θ of grid stripes.

Figure 12A:
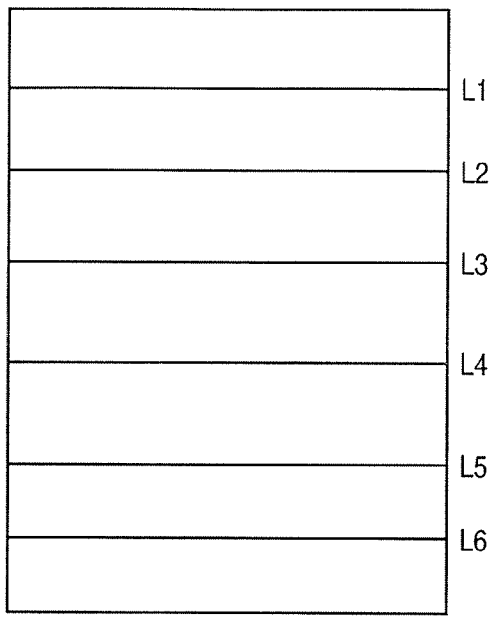
FIGS. 12A to 12D are views for explaining detection (analysis) of grid stripe components for an objective image of the X-ray image capture apparatus.

FIG. 12A shows an image of the overall objective image, and "L1" to "6" indicate line positions from the top of the objective image. The grid stripe detector 116 measures the spatial frequency fm of grid stripes based on the Fourier transformation results of lines L1 to L6. Upon detecting the spectrum of grid stripes, the grid stripe detector 116 may use the average of several lines before and after each of lines L1 to L6 to improve the detection performance.

Figure 12B:
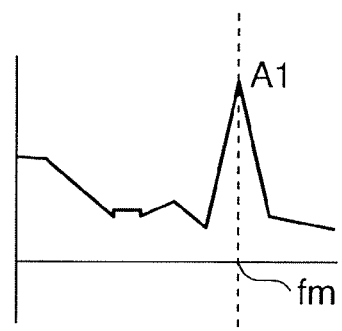
Figure 12C:
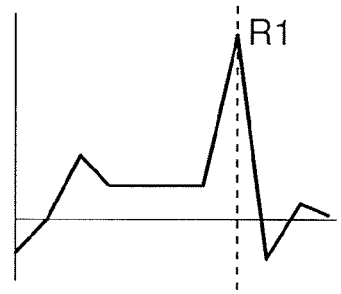
Figure 12D:
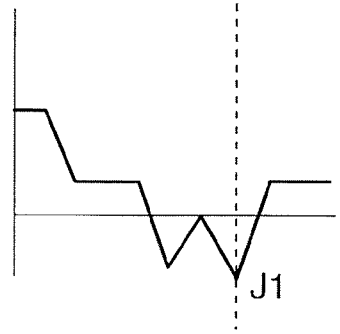

FIGS. 12B to 12D respectively show the Fourier transformation results of line L1.

That is, FIG. 12B shows the amplitude spectrum (or power spectrum), FIG. 12C shows the values of the real part as coefficients of the cosine wave of the Fourier transformation result, and FIG. 12D shows the values of the imaginary part as coefficients of the sine wave.

Figure 13:
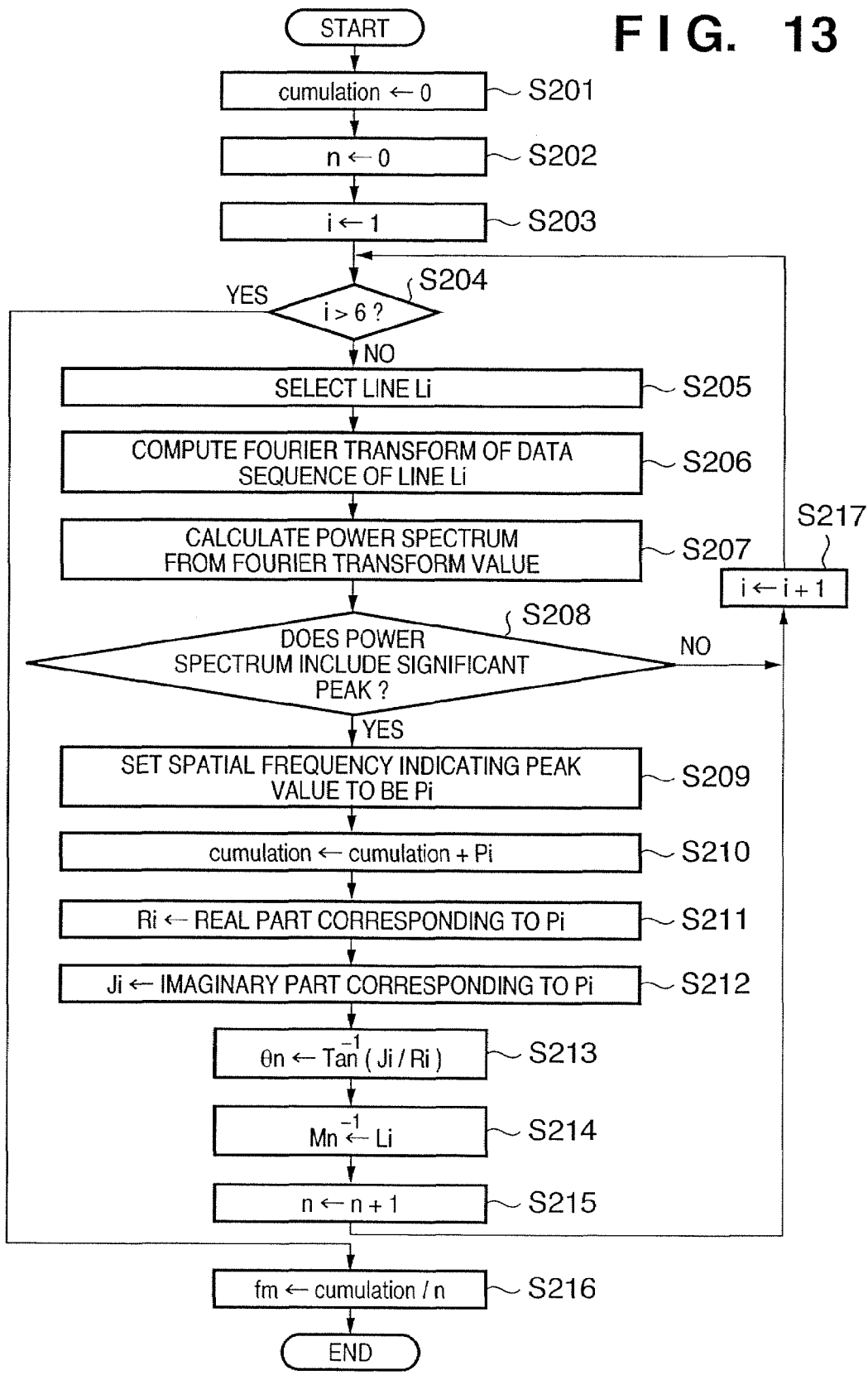
FIG. 13 is a flow chart for explaining the detection (analysis) process of the grid stripe components.

FIG. 13 is a flow chart showing the process of the grid stripe detector 116.

The grid stripe detector 116 clears variable cumulation used to obtain the average of the spectrum (step S201).

Also, the grid stripe detector 116 clears counter (variable) n of the number of lines used upon calculating the average of the spectrum (step S202).

Furthermore, the grid stripe detector 116 resets variable i used to select the line of interest (selected line) from lines L1 to L6 shown in FIG. 12A to "1" (step S203). As a result, the first process starts while selecting line L1 as the line of interest.

The grid stripe detector 116 checks if the processes in subsequent steps S205 to S215 are complete for all lines L1 to L6 of the objective image (step S204).

If it is determined as a result of checking that the processes are complete, the flow jumps to step S216 (to be described later); otherwise, the processes from the next step S205 is executed.

If it is determined in step S204 that processes are not complete, the grid stripe detector 116 selects line Li indicated by variable i from lines L1 to L6 of the objective image, and acquires its data (line data Li) (step S205).

The grid stripe detector 116 executes a Fourier transformation process (e.g., fast Fourier transformation) of line data Li acquired in step S205 (step S206).

The grid stripe detector 116 acquires the power spectrum (or amplitude spectrum) from the Fourier transformation result (data in the spatial frequency domain) in step S206 (step S207).

The grid stripe detector 116 checks if a significant spectrum (peak value) indicating a grid stripe is present in the power spectrum acquired in step S207 (step S208).

More specifically, since the absolute spatial frequency of grid lead as a source of generation of grid stripes is known upon attaching the grid 113, the checking process in step S208 can be accurately made using that frequency as "fg".

More specifically, let "Ts" be the sampling pitch of the X-ray sensor 104. Then, a rough spatial frequency fm' at which grid stripes are generated can be specified by:

$$\begin{aligned}&\text{①}\ J = 1 \\ &\text{②}\ fm' = \left| J\frac{1}{Ts} - fg \right| \\ &\text{③}\ \text{Is condition}\ fm' < \frac{1}{Ts}\ \text{satisfied?}\end{aligned} \quad (13)$$

At this time, if condition ③ is satisfied in formulas (13), the spatial frequency fm' obtained by ② is used; if condition ③ is not satisfied, ① is executed while "J←J+1".

The accurate spatial frequency fm of grid stripes should be present in the neighborhood of "fm'" obtained by formulas (13). Hence, upon checking if a peak value (significant spectrum indicating a grid stripe) is present, the neighboring values need only be searched to detect the peak value as the significant spectrum indicating the grid stripe without being influenced by different peak values under the influence of image components, noise components, or the like caused by an object.

The grid 103 is manufactured accurately so that the frequency fg of grid lead assumes a predetermined value over the entire grid 103. However, if the grid 103 and X-ray sensor 104 are separated by an arbitrary distance or more upon photographing, since an X-ray beam from the X-ray generator 101 has a cone beam shape, the X-ray beam reaches the X-ray sensor 104 in an enlarged scale. For this reason, the accurate spatial frequency fm changes, and cannot be predicted easily.

Therefore, of frequencies near "fm" obtained by formulas (13), the frequency indicated by the peak value is obtained as the spatial frequency fm.

In the above-mentioned case, it must be checked if the obtained peak value is a significant peak value which is present stably in practice. This checking process is normally done based on noise level. The noise level may be measured in advance or the average value of components other than the peak value in the high-frequency range of the spectrum may be used instead. For example, if the ratio of the sum total (or average value) of the power spectra of spectral values near that of the peak value and noise level is equal to or larger than 10, it is determined that the obtained peak value is a significant, stable peak value.

If it is determined in step S208 that no significant peak value is found, the grid stripe detector 116 increments variable i to process the next line (step S217), and the flow returns to step S204 to repeat the subsequent processing steps.

On the other hand, if it is determined in step S208 that a significant peak value is found, the grid stripe detector 116 adds the spatial frequency indicating the peak value to variable cumulation (step S210) as Pi (step S209).

The grid stripe detector 116 obtains the phase of the grid stripe, sets that phase and line position indicated by variable i in variables θn and Mn (steps S211 to S214), and increments variable n (step S215).

After that, the grid stripe detector 116 increments variable i to process the next line (step S217), and the flow returns to step S204 to repeat the subsequent processing steps.

Upon completion of the processes in steps S205 to S215 for all lines L1 to L6, the grid stripe detector 116 obtains the average spatial frequency fm of grid stripes by dividing the current value of variable cumulation by the current value of variable n (the number of significant peak values) (step S216).

After the process in FIG. 13, the grid stripe detector 116 uses variable θi (i=0 to n−1) obtained in step S213 in a process for obtaining an average angle η (angle θ) of grid stripes depending on the line position Mi (i=0 to n−1) in step S214.

More specifically, the grid stripe detector 116 calculates the difference between positions on the grid 103 as a phase difference $(\theta_i - \theta_{i+1})$ between phases $\theta_i$ and $\theta_{i+1}$ of i-th and (i+1)-th lines Li and L(i+1) using the spatial frequency fm of grid stripes by:

$$\{(\theta_i - \theta_{i+1})/2\pi\}/fm$$

also calculates the line difference between lines Li and L(i+1) by:

$$(Mi+1) - Mi$$

and calculates based on these results the angle η of grid stripes by:

$$\eta = \text{Tan}^{-1}\left(\frac{(\theta_{i+1} - \theta_i)/2\pi}{(M_{i+1} - M_{i+1})fm}\right) \quad (14)$$

When the angle η calculated by equation (14) is equal to or smaller than a predetermined angle (not inclined abnormally), the grid stripe extraction process is done for every several lines; when the angle η exceeds the predetermined angle (inclined abnormally), the grid stripe extraction process is done for every line.

Note that the process is executed by the grid stripe detector 116 under the condition that the direction of grid stripes (vertical or horizontal direction) is known. For example, if the direction of grid stripes is unknown, the same process is executed in advance in both the vertical and horizontal directions, and the direction in which a significant peak value is detected is determined to be a direction nearly perpendicular to grid stripes.

When the grid stripe detector 116 detects the aforementioned process, the spatial frequency fm and angle θ (angle η) of grid stripes are obtained.

The grid stripe component extraction unit 116 extracts grid stripe components from the objective image data which is stored in practice in the memory 113 and contains grid stripe components using the spatial frequency fm and angle θ (angle η) of grid stripes obtained by the grid stripe detector 116, and stores the extracted grid stripe components in the memory 118.

Figure 14A:
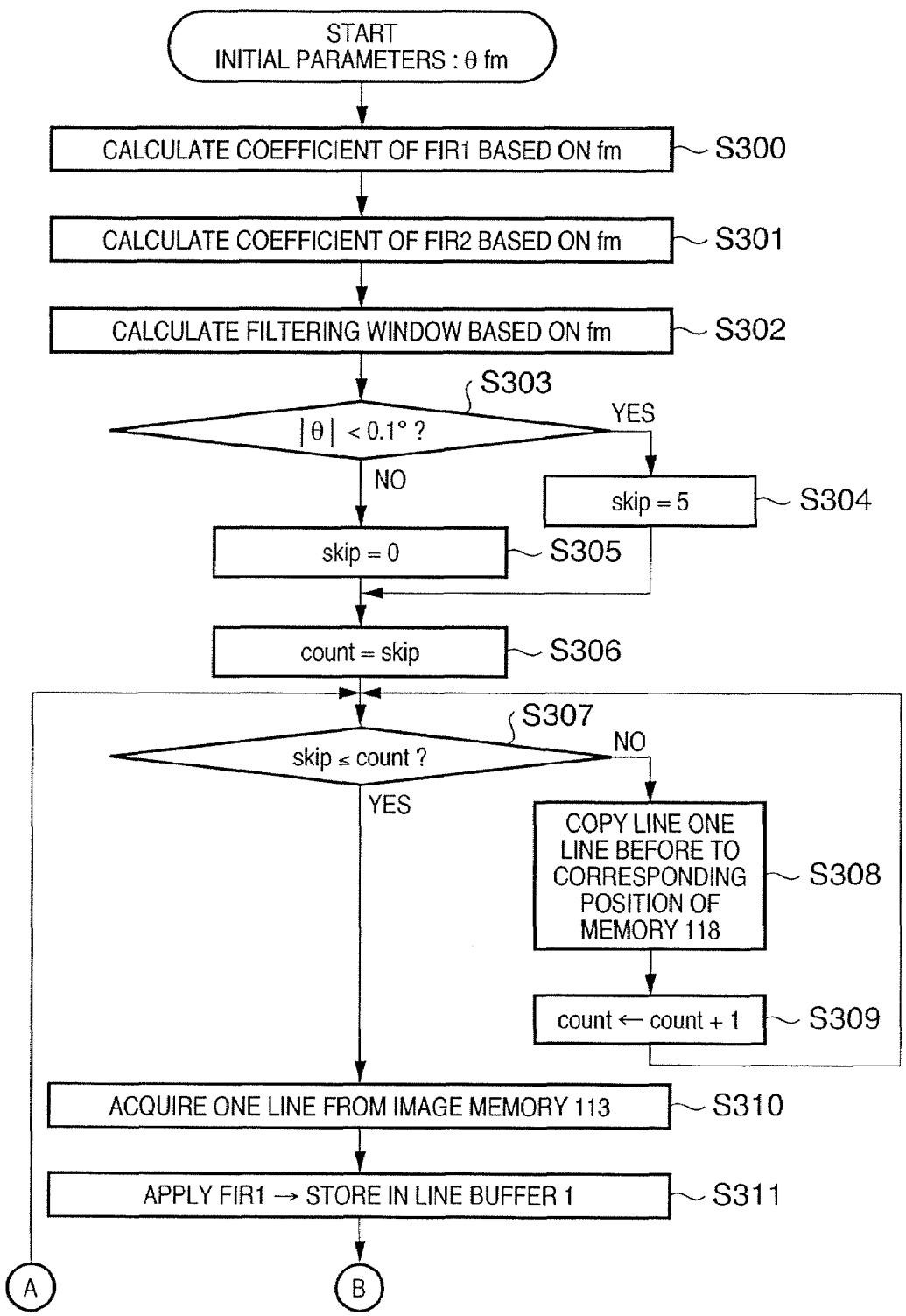
FIGS. 14A and 14B is a flow chart for explaining the process for extracting grid stripe components from an objective image on the basis of the result of the detection (analysis) process of the grid stripe components.
Figure 14B:
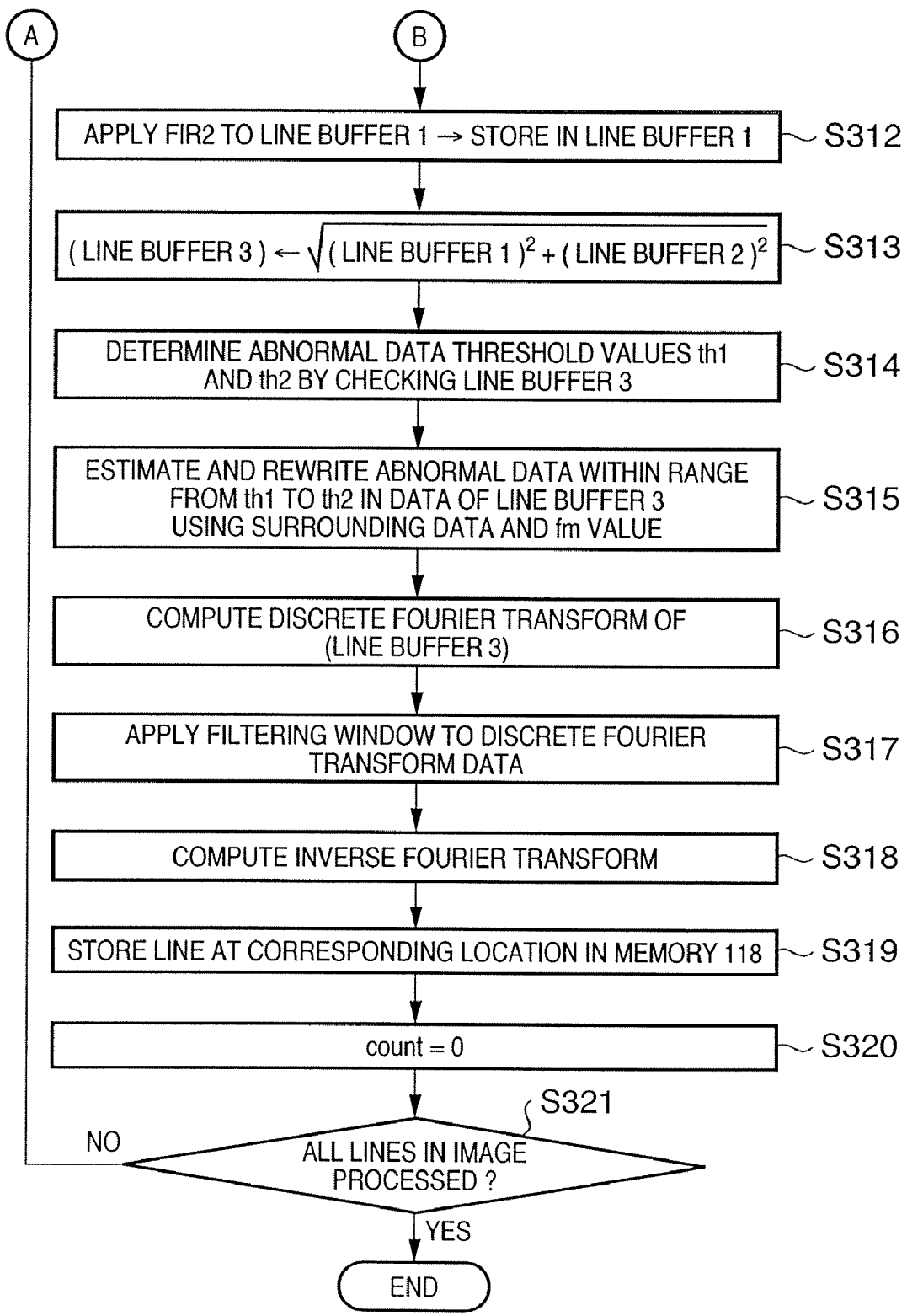

FIGS. 14A and 14B is a flow chart showing the grid stripe component extraction process by the grid stripe component extraction unit 117.

The grid stripe component extraction unit 117 receives the angle θ and spatial frequency fm of grid stripes obtained by the grid stripe detector 116 as processing parameters.

The grid stripe component extraction unit 117 executes processes in steps S300 to S321 to be described below based on the processing parameters (angle θ and spatial frequency fm of grid stripes).

If the spatial frequency fm of grid stripes input to the grid stripe component extraction unit 117 is "0", there are no grid stripes on the objective image, i.e., photographing is made without using the grid 103. In this case, the grid stripe component extraction unit 117 does not execute the process shown in FIGS. 14A and 14B. The memory 118 stores "0" data as grid stripe components in such case. Or the arithmetic device 119 does not operate, and the objective image data stored in the memory 113 is directly stored in the memory 120.

When the grid stripe detector 116 supplies the angle θ and spatial frequency fm of grid stripes to the grid stripe component extraction unit 117, the grid stripe component extraction unit 117 calculates coefficients a1 and a2 (or coefficients (a2, b2, c2, b2, a2) of the 5-tap filter) from the spatial frequency fm using equations (2) (step S300). Assume that an FIR filter corresponding to the coefficients obtained in this step is "FIR1".

The grid stripe component extraction unit 117 calculates coefficient a3 from the spatial frequency fm using equation (3) (step S301). Assume that an FIR filter corresponding to the coefficient obtained in this step is "FIR2".

The grid stripe component extraction unit 117 generates a window function having the spatial frequency fm as the center to implement FIR filtering in the domain of the spatial frequency fm (step S302).

As the window function, for example, a Gaussian distribution function having the spatial frequency fm as the center may be applied.

The grid stripe component extraction unit 117 determines the range of lines, for which the grid stripe extraction process is to be executed, of line data which form the objective image, on the basis of the angle θ of grid stripes (step S303 to S305).

More specifically, the grid stripe component extraction unit 117 sets a reference value of the angle θ to be "0.1°", and checks if the angle θ of grid stripes obtained by the grid stripe detector 116 is larger than the reference value "0.1°" (step S303). As a result of this checking, if the angle θ is smaller than the reference value "0.1°", the grid stripe component extraction unit 117 sets "5" in variable skip, i.e., determines that the process is skipped every five lines (step S304). On the other hand, if the angle θ is equal to or larger than the reference value "0.1°", the grid stripe component extraction unit 117 sets "0" in variable skip, i.e., determines that the process is executed for all lines (step S305).

In steps S303 to S305, not only the setup of variable skip, but also more detailed setups may be made based on the angle θ.

After the process in step S304 or S305, the grid stripe component extraction unit 117 sets the value of variable skip set in step S304 or S305 in variable count, thus initializing variable count (step S306).

The grid stripe component extraction unit 117 checks if the current value of variable count is equal to or larger than the value of variable skip, i.e., the grid stripe extraction process is to be executed for the line data of interest (step S307).

As a result of checking, if the process is to be executed, the flow advances to step S310; otherwise, the flow advances to step S308. If step S307 is executed for the first time, since it is determined that the process is to be executed, the flow advances to step S310.

If it is determined in step S307 that the process is to be executed (skip≦count), the grid stripe component extraction unit 117 acquires one line data to be processed (line data of interest) from the objective image data stored in the memory 113 (step S310).

Instep S310, the line data of interest may be directly acquired from the objective image data. Alternatively, for example, the average value (moving average value) of several lines before and after the line data of interest may be acquired as actual line data to be processed.

The grid stripe component extraction unit 117 filters the line data of interest acquired in step S310 using FIR1, the coefficients of which are determined in step S300, and stores the result in line buffer 1 (not shown) (step S311).

With this process, line buffer 1 stores image component data that contain grid stripe components.

The grid stripe component extraction unit 117 filters the line data stored in line buffer 1 using FIR2, the coefficient of which is determined in step S301, and stores the result in line buffer 2 (not shown) (step S312).

With this process, line buffer 2 stores data used to obtain the envelope of grid stripe components.

The grid stripe component extraction unit 117 then calculates the envelope of grid stripe components (step S313).

More specifically, the grid stripe component extraction unit 117 calculates the amplitude of a vector (i.e., the square root of square sums) having data in line buffers 1 and 2 as components, and stores the result in line buffer 3 (not shown). As the arithmetic operation to be made in this case, an arithmetic operation that does not calculate any square root may be applied due to monotonous increase of the square root, and the same effect may be obtained.

The grid stripe component extraction unit 117 inspects the data in line buffer 3, i.e., envelope data, and determines upper and lower limit values th1 and th2 used to detect abnormal data (step S314).

As the method of determining the upper and lower limit values th1 and th2, various methods may be applied. For example, a method of calculating the average and standard deviation, and determining values larger and smaller than the average value by n times (e.g., "3") of the standard deviation to be the upper and lower limit values th1 and th2, a method of calculating the histogram of the envelope data in line buffer 3 and determining the upper and lower limit values th1 and th2 to have the mode of the histogram as the center, and the like are available.

The grid stripe component extraction unit 117 determines data falling outside the range from the value th1 to the value th2 (both inclusive) as abnormal data (data corresponding to a steep variation of image data) in the envelope data in line buffer 3, estimates grid stripe component data in line buffer 1 corresponding to that abnormal data from data around the abnormal data, and rewrites the abnormal data by the estimated data (step S315). At this time, the data is rewritten to attain a stable state in which all grid stripe components form a periodic variation pattern.

Note that the process in step S315 have been explained in the paragraphs of equations (7'), and a detailed description thereof will be omitted.

The grid stripe component extraction unit 117 executes a Fourier transformation process of grid stripe component data in line buffer 1, which have a stable state as a whole, by the process in step S315, thus obtaining grid stripe component data of the spatial frequency domain (step S316).

Note that the transformation process in step S316 is not limited to Fourier transformation and, for example, orthogonal transformation such as cosine transformation or the like may be applied.

The grid stripe component extraction unit 117 filters the data of the spatial frequency domain acquired in step S316 using the window function having the spatial frequency fm as the center, which is generated in step S302 (step S317). As a result, the grid stripe component data represent grid stripes more selectively.

The grid stripe component extraction unit 117 executes an inverse transformation process of the transformation in step S316 for the grid stripe component data that have undergone filtering in step S317, and sets this processing result as actual grid stripe component data (step S318).

The grid stripe component extraction unit 117 stores the grid stripe component data acquired in step S318 at corresponding locations of the memory 118 (step S319).

The grid stripe component extraction unit 117 sets "0" in variable count (step S320), and checks if the processes starting from step S307 have been executed for all line data which form the objective image data in the memory 113 (step S321).

If it is determined in step S321 that the processes are complete, this process ends; otherwise, the flow returns to step S307 to repeat the subsequent processing steps.

On the other hand, if it is determined in step S307 that the process is not to be executed (skip>count), the grid stripe component extraction unit 117 copies the grid stripe component data acquired in the previous process to the corresponding locations of the memory 118 (step S308), and increments variable count indicating the line to be copied (step S309). After that, the flow returns to step S307 to repeat the subsequent processing steps.

Second Embodiment

Figure 15:
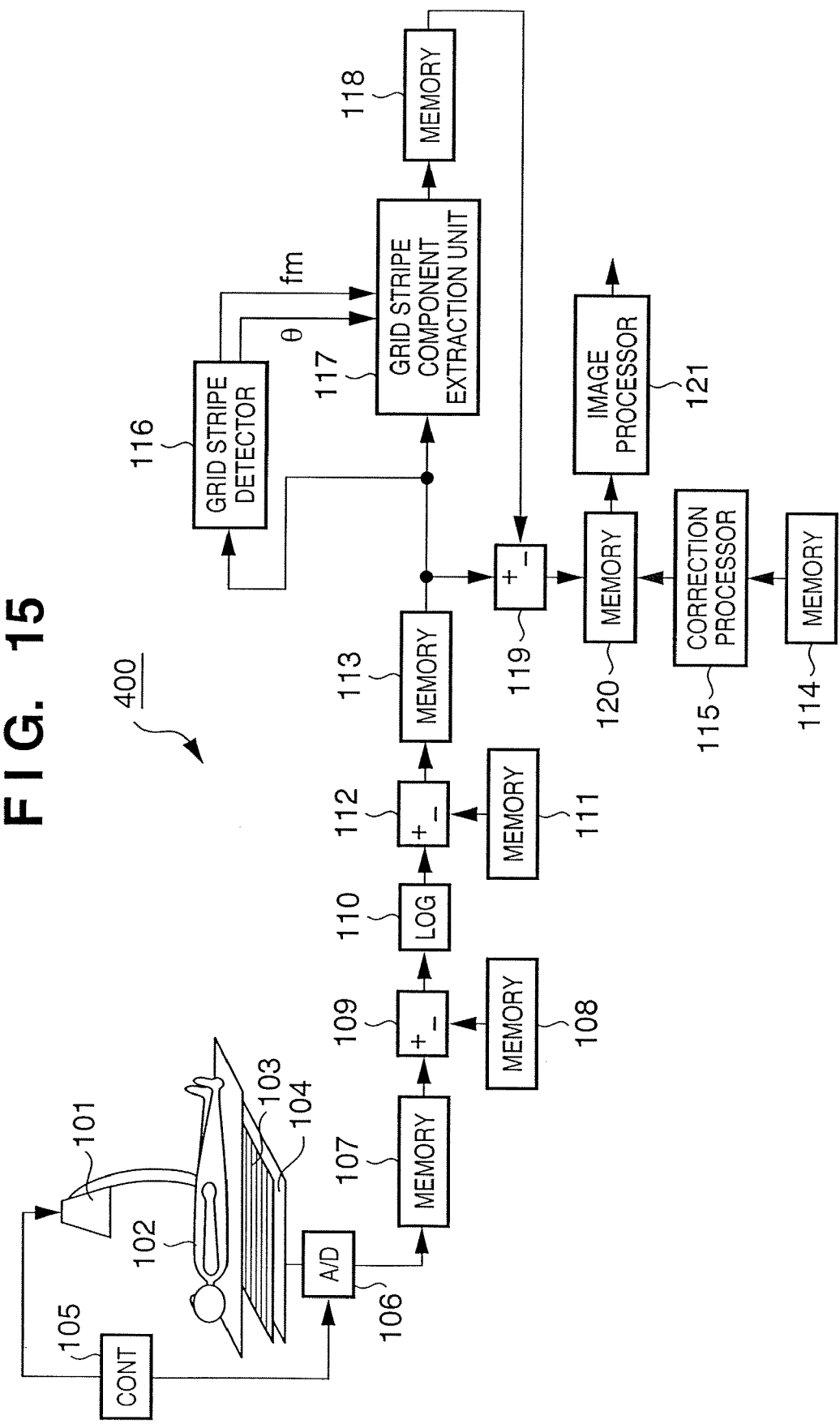
FIG. 15 is a block diagram showing the arrangement of an X-ray image capture apparatus to which the present invention is applied in the second embodiment.

The present invention is applied to, e.g., an X-ray image capture apparatus 400 shown in FIG. 15.

Note that the same reference numerals in the X-ray image capture apparatus 400 in FIG. 15 denote the same parts as in the X-ray image capture apparatus 100 in FIG. 6, and a detailed description thereof will be omitted.

In the X-ray image capture apparatus 100 in FIG. 6, the correction processor 115 executes the defective pixel correction process using data in the memory 114 for the objective image data in the memory 113. By contrast, in the X-ray image capture apparatus 400 of this embodiment, as shown in FIG. 15, the correction processor 115 executes the defective pixel correction process using data in the memory 114 for the objective image data in the memory 120, i.e., for the objective image data after the grid stripe components have been removed.

Therefore, according to the X-ray image capture apparatus 400 of this embodiment, since the need for pixel defect correction that takes grid stripes into account is obviated, conventional, simple defective pixel correction, which corrects defective pixels using the average value of surrounding non-defective pixel values, can be applied.

Third Embodiment

Figure 16:
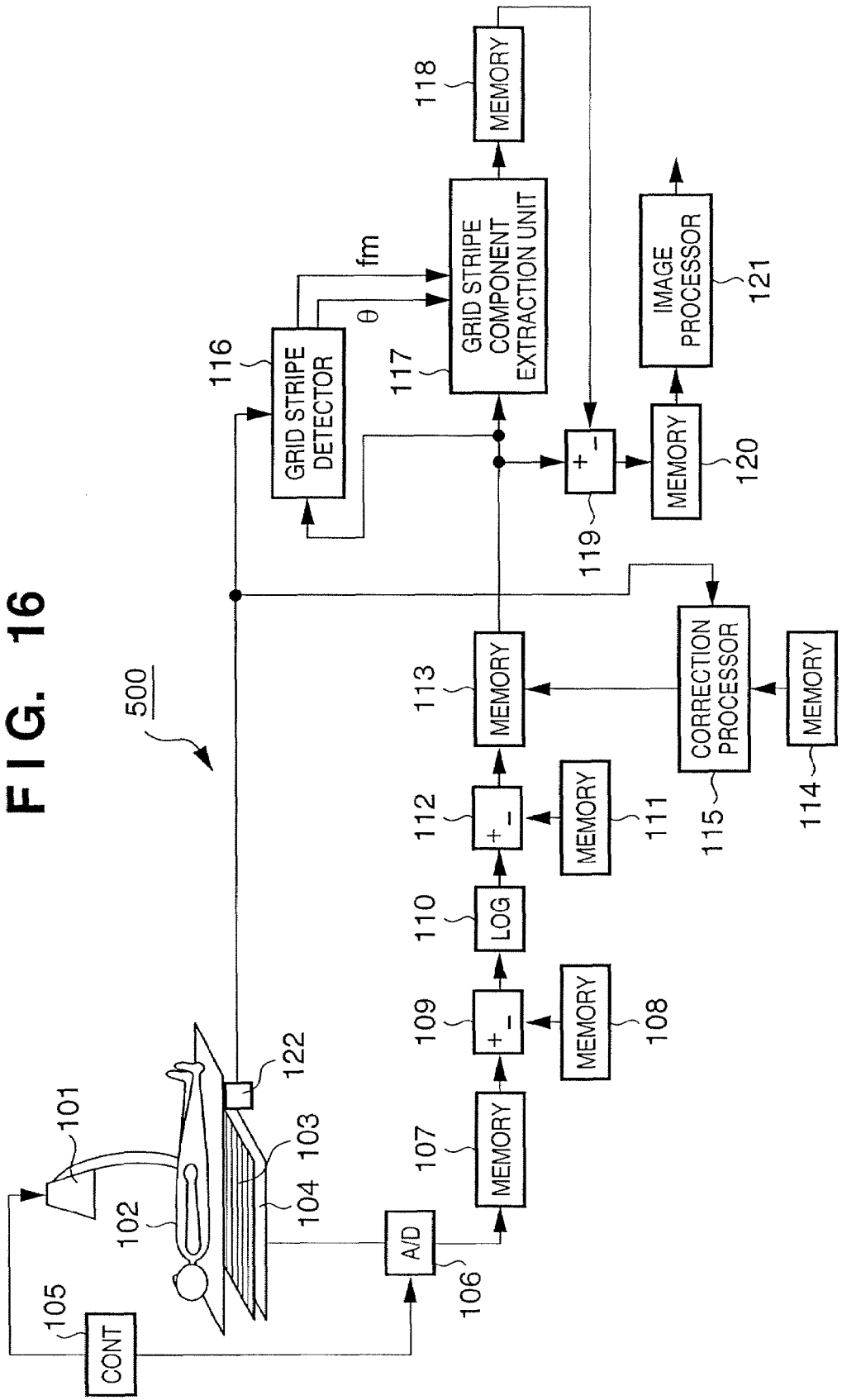
FIG. 16 is a block diagram showing the arrangement of an X-ray image capture apparatus to which the present invention is applied in the third embodiment.

The present invention is applied to, e.g., an X-ray image capture apparatus 500 shown in FIG. 16.

Note that the same reference numerals in the X-ray image capture apparatus 500 in FIG. 16 denote the same parts as in the X-ray image capture apparatus 100 in FIG. 6, and a detailed description thereof will be omitted.

The X-ray image capture apparatus 500 of this embodiment has a detector (switch) 122 for detecting attachment of the grid 103 in addition to the arrangement of the X-ray image capture apparatus 100 in FIG. 6, as shown in FIG. 16.

The detector 122 supplies the detection result (grid attachment signal) of attachment of the grid 103 to the correction processor 115 and grid stripe detector 116.

When it is detected based on the grid attachment signal from the detector 122 that the grid 103 is attached, the correction processor 115 executes a defective pixel correction process that considers grid stripes, as has been explained in the first embodiment. Otherwise, the correction processor 115 corrects defective pixels using, e.g., the average value of surrounding non-defective pixel values.

Likewise, when it is detected based on the grid attachment signal from the detector 122 that the grid 103 is attached, the grid stripe detector 116 executes a grid stripe detection process (analysis process), as has been explained in the first embodiment. However, when it is detected based on the grid attachment signal that the grid 103 is not attached, the grid stripe detector 116 skips the grid stripe detection process, immediately determines the absence of grid stripes, and executes a corresponding process.

As described above, since the X-ray image capture apparatus 500 of this embodiment has the detector 122 and detects grid stripes based on the detection result of the detector 122, the time required for the process for detecting grid stripes can be greatly shortened.

Fourth Embodiment

Figure 17:
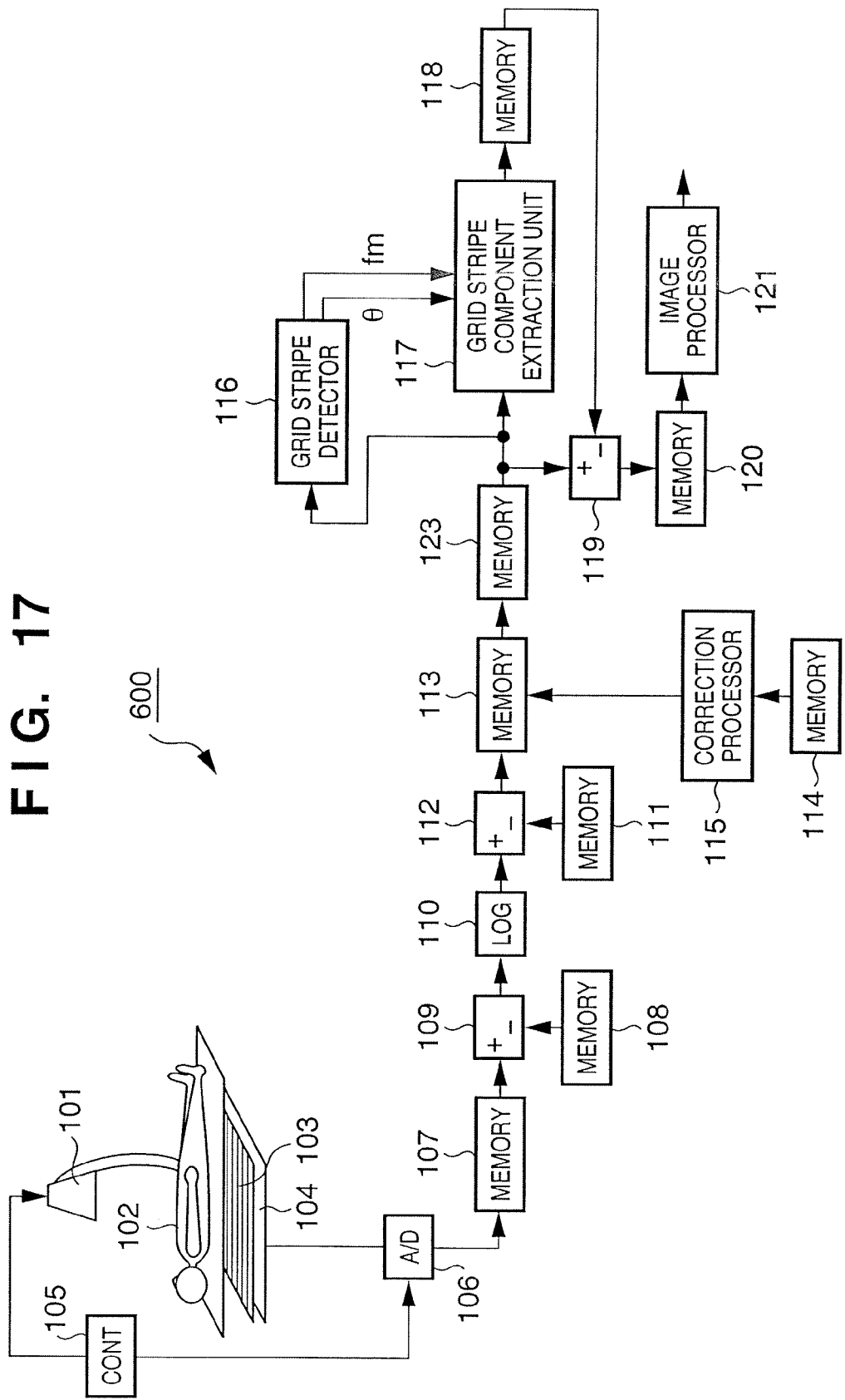
FIG. 17 is a block diagram showing the arrangement of an X-ray image capture apparatus to which the present invention is applied in the fourth embodiment.

The present invention is applied to, e.g., an X-ray image capture apparatus 600 shown in FIG. 17.

The arrangement of the X-ray image capture apparatus 600 of this embodiment is different from the X-ray image capture apparatus 100 shown in FIG. 6 in the following respects.

Note that the same reference numerals in the X-ray image capture apparatus 600 in FIG. 17 denote the same parts as in the X-ray image capture apparatus 100 in FIG. 6, and a detailed description thereof will be omitted.

The X-ray image capture apparatus 600 of this embodiment further comprises a memory 123 for storing X-ray irradiated region data in addition to the arrangement of the X-ray image capture apparatus 100 in FIG. 6, as shown in FIG. 17.

The memory 123 stores image data (irradiated region data) obtained by extracting only a region irradiated with X-rays from the objective image data stored in the memory 113, and the irradiated region data in the memory 123 undergo detection and extraction of grid stripe components.

More specifically, in X-ray radiography, it is a common practice to provide an irradiation field stop to the exit of an X-ray generation bulb of the X-ray generator 101 so as to avoid a portion other than a target portion of the object 102 (human body in this case) from being exposed. With this field stop, only the required portion of the object 102 can be irradiated with X-rays.

When the irradiation field stop function is used, not all image signals obtained from the X-ray sensor 104 are effective but only a partial image corresponding to an X-ray irradiation field defined by the irradiation field stop is effective in an image obtained by X-ray radiography.

Hence, in this embodiment, a computer means (CPU or the like; not shown) detects an effective partial image region (irradiated region) corresponding to the X-ray irradiation field from the objective image data in the memory 113 on the basis of the X-ray intensity distribution and stop shape, or other information, and stores only the data of that irradiated region (irradiated region data) in the memory 123.

As described above, since this embodiment processes only the irradiated region data in the memory 123, i.e., not all objective image data but only data of the required portion with the reduced information size, the processing time can be shortened.

In this embodiment, the irradiated region is extracted from the objective image after defective pixel correction. For example, after the irradiated region is extracted, defective pixel correction may be executed for that irradiated region.

Fifth Embodiment

In the X-ray image capture apparatus 100 in FIG. 6 of the first embodiment, the grid stripe component extraction process of the grid stripe component extraction unit 117 is executed according to the flow chart shown in FIGS. 14A and 14B.

Figure 18A:
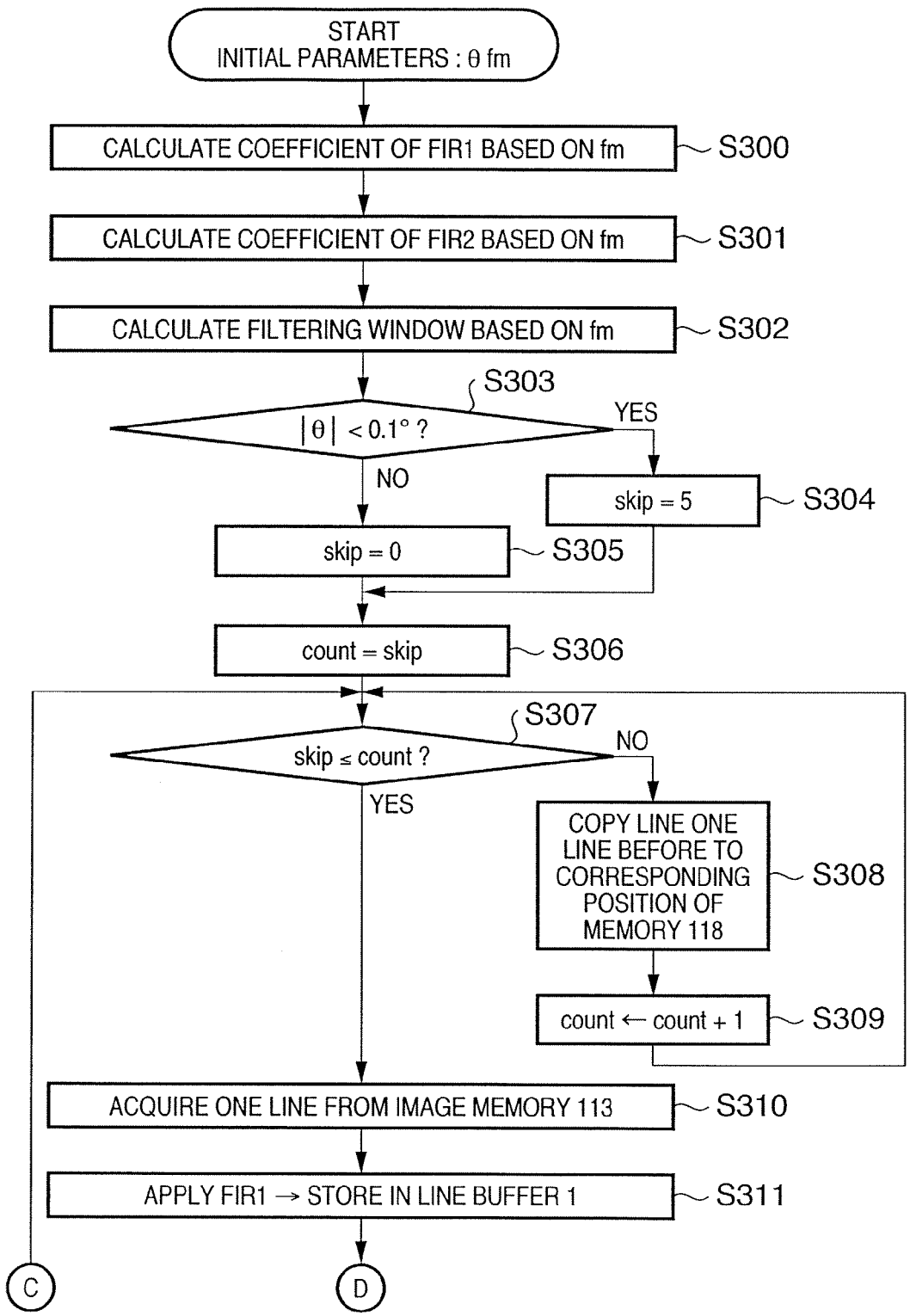
FIGS. 18A and 18B is a flow chart for explaining the process for extracting grid stripe components from an objective image on the basis of the result of the detection (analysis) process of the grid stripe components in the fifth embodiment.
Figure 18B:
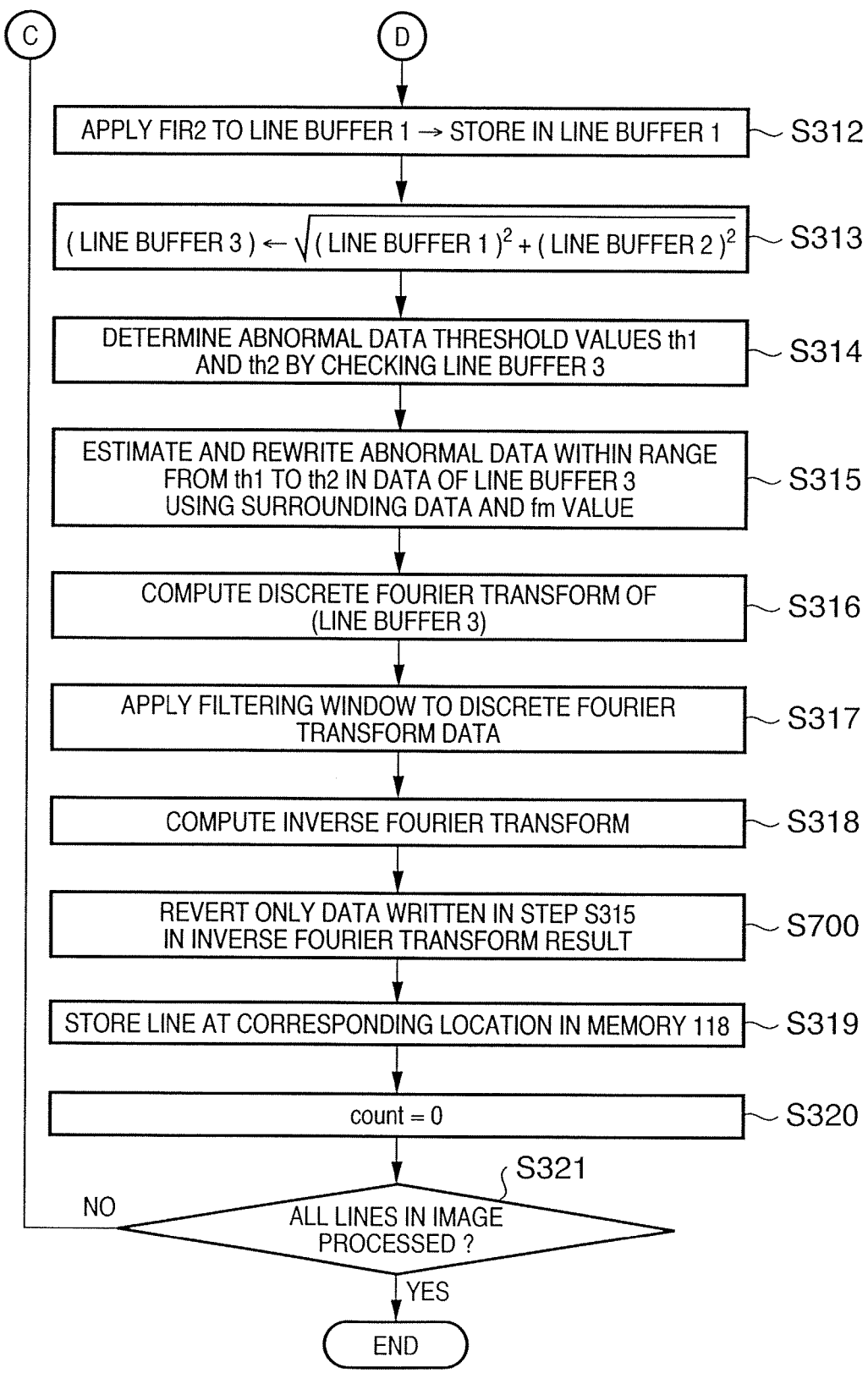

In this embodiment, the grid stripe component extraction process of the grid stripe component extraction unit 117 is executed according to the flow chart shown in, e.g., FIGS. 18A and 18B.

Note that the same step numbers in the grid stripe component extraction process in FIGS. 18A and 18B denote the same processes as in that shown in FIGS. 14A and 14B, and a detailed description thereof will be omitted.

Figures 19A, 19B, 19C, 19D:
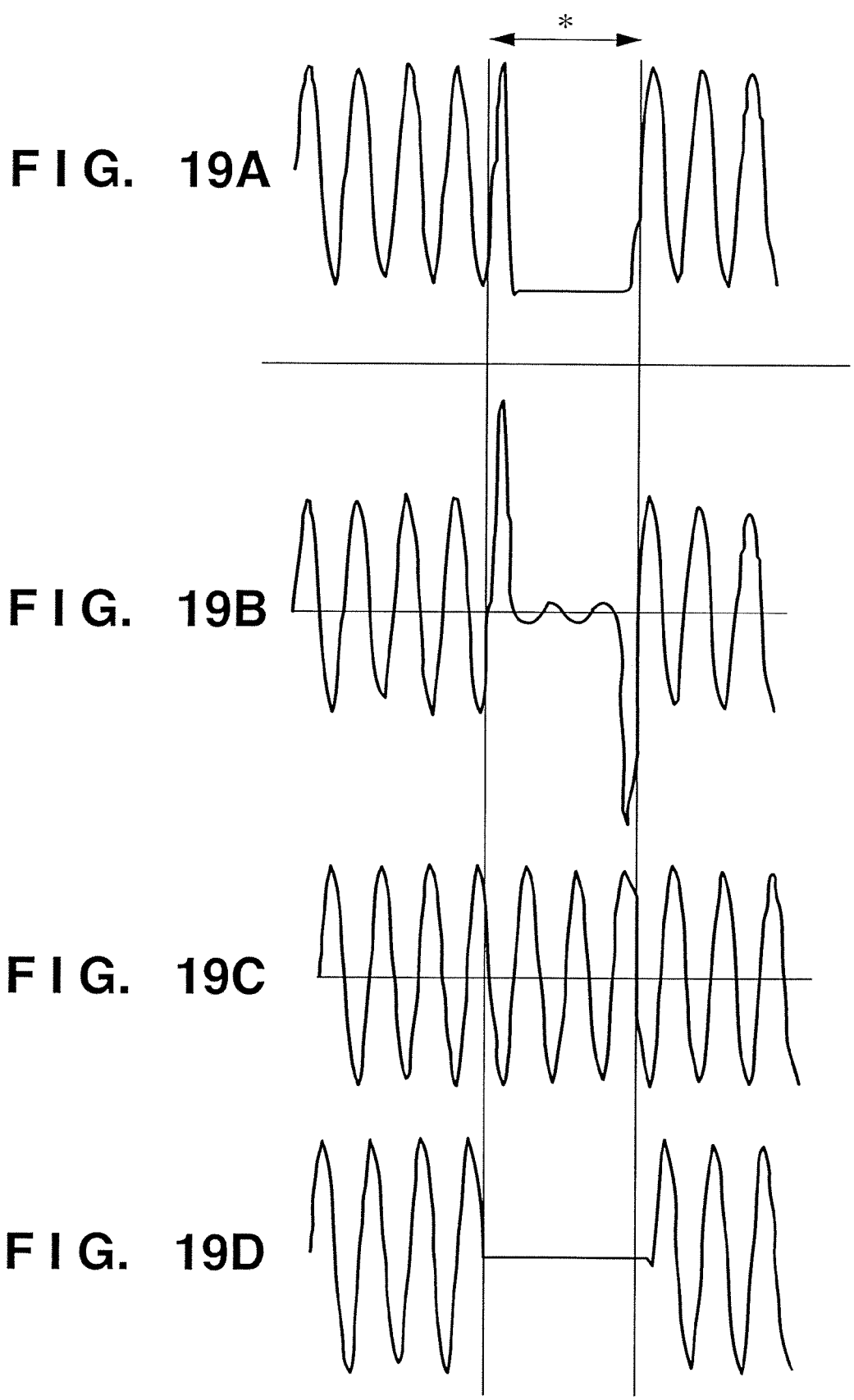
FIGS. 19A to 19D are graphs for explaining examples of the process for extracting the grid stripe components.

Prior to the description of the grid stripe component extraction process of this embodiment, FIG. 19A partially shows an objective image containing grid stripe components. In FIG. 19A, "*" indicates a portion where no grid stripe components are present due to, e.g., the presence of an X-ray shielding material.

FIG. 19B shows the grid stripe component extraction result by filtering the objective image shown in FIG. 19A as in the first embodiment. As shown in FIG. 19B, since artifacts appear in the portion "*" corresponding to the objective image, this portion is extracted from the envelope, and is estimated from data before and after that portion to obtain stable grid stripe components as a whole. FIG. 19C shows this result. If such stable grid stripe components are obtained, no new artifacts are generated by the transformation process such as Fourier transformation or the like.

In the first embodiment, the grid stripe components shown in FIG. 19C are subtracted from the source image (objective image) shown in FIG. 19A to remove the grid stripe components. However, in case of this arrangement, new grid stripe components may appear in a portion where no grid stripe components are present (the portion indicated by "*").

Hence, in this embodiment, as shown in FIG. 19D, the portion where no grid stripe components are present (the portion indicated by "*") is set to be "0" in the grid stripe components shown in FIG. 19C.

For this purpose, in this embodiment, the grid stripe component extraction unit 117 executes the grid stripe component extraction process according to the flow chart in FIGS. 18A and 18B.

More specifically, after the process in step S318, the grid stripe component extraction unit 117 executes a process for substituting the portion compensated for stable grid stripe component data acquired by the process in step S318 by estimation in step S315 by "0" (step S700), and the flow then advances to step S319. With this process, new grid stripe components can be reliably prevented from being generated by the grid stripe removal process even in a portion where no grid stripe components are present.

Outline of Sixth to 10th Embodiments

The same problems of the radiation images described in the prior art apply to moving images obtained by radiography.

More specifically, in case of an arrangement for capturing an X-ray image of an object by sensing X-rays by a solid-state image sensing element via the object, a series of successive images (X-ray images of a moving image, to be also referred to as an X-ray moving image hereinafter) can be acquired in correspondence with the movement of the object. In such X-ray moving image, each individual frame image which forms the X-ray moving image suffers the aforementioned problems of grid stripe components.

An X-ray moving image is captured at high speed, e.g., at 30 to 120 frames per sec. It is very difficult to perfectly remove grid stripe components from the X-ray moving image obtained at such high speed. Furthermore, since the X-ray moving image is captured at high speed, if grid stripe components are removed by simple filtering, the image itself is damaged (e.g., artifacts appear).

Hence, in the following sixth to 10th embodiments, a radiation image processing apparatus, image processing system, radiation image processing method, storage medium, and program, which can obtain a high-quality radiation moving image from which image components caused by a grid have been removed from a radiation image captured by radiography using the grid will be explained.

Assume that X-rays are used as an example of radiation, and an X-ray image obtained by X-ray radiography will be processed.

The arrangement to be described below is an example to which the present invention is applied, and the present invention is not limited to such specific arrangement.

In the sixth to 10th embodiments, the present invention solves, by the following arrangement, a problem of difficulty in removal of grid stripe components by a simple filtering process, and a problem of difficulty in high-speed removal of grid stripe components especially for an X-ray moving image upon capturing a series of successive images (X-ray moving image) corresponding to the movement of an object by X-ray radiography using a grid.

That is, component information of grid stripes (to be also simply referred to as "grid stripe components" hereinafter), which is superposed on each of a plurality of frame images that form an X-ray moving image to be processed (objective X-ray moving image) or should be present as a stable stripe pattern over the entire image and cannot be detected by a normal filtering process due to, e.g., the influence of the sensor characteristics (saturation characteristics, or characteristics of defective pixels or the like) is obtained by estimation, thereby extracting the grid stripe components.

In a plurality of frame images which form the objective X-ray moving image, since neighboring frame images have nearly the same grid stripe components, a grid stripe component extraction process is executed not for all of the plurality of frame images, but for frame images remaining after decimation.

For example, when each frame image is a logarithmic image signal, the extracted grid stripe components are subtracted from that frame image. In this manner, grid stripe information can be stably removed without influencing the X-ray moving image.

More specifically, in the sixth embodiment, one frame image (objective frame image) of an X-ray moving image obtained by X-ray radiography is analyzed. As for a pixel defect in a direction perpendicular to the grid stripes, a linear predictive pixel defect correction process is executed. Also, the grid stripe components are extracted from the objective frame image based on the analysis result, and are held as image information.

Since the time required for analysis is longer than that of successively captured frame images, frame images between the objective frame image from which grid stripe components have been extracted by analysis as a start frame and the next frame image to be analyzed undergo a grid stripe component removal process using previously extracted grid stripe components until analysis of the next frame image is completed. At this time, grid stripe components may be periodically extracted under the control of another timing control arrangement which corresponds to the time required for analysis.

In the sixth embodiment, upon extracting grid stripe components from the objective frame image, the grid stripe components are temporarily extracted by low-order FIR filtering, and envelope information is acquired by a vector amplitude characteristic calculation between that filtering result and another FIR filtering result. An unsteady portion is extracted from the grid stripe components based on the envelope information, and is patched using a steady portion around it, thus converting the grid stripe components into a signal sequence which is steady as a whole. Furthermore, in order to extract grid stripe components alone more appropriately, a filtering process for selectively extracting the spatial frequency corresponding to the grid stripe components is executed, and that filtering result is determined to be grid stripe components.

The grid stripe components acquired as described above are subtracted from each frame image. In this way, an X-ray moving image after the grid stripe components are removed can be obtained.

In the seventh embodiment, each frame image after grid stripe components are removed undergoes pixel defect correction. As the pixel defect correction, that based on, e.g., an average can be applied.

In the eighth embodiment, a detection means for detecting attachment of a grid is provided. When the detection means confirms attachment of the grid, each frame image is analyzed, and predictive pixel defect correction and removal of grid stripe components are executed based on the analysis result.

In the ninth embodiment, when the irradiation field of X-ray exposure is stopped down in correspondence with a portion to be photographed of an object, only a partial image corresponding to the irradiation field in each frame image undergoes the processing of the sixth embodiment.

The 10th embodiment adopts a method of inhibiting a grid stripe removal process for an image in a portion where no grid stripes are present, since no grid stripes are present in some image portions depending on the condition of an object.

More specifically, by replacing information of a portion where no grid stripe components are present by zero ("0") data, that portion does not undergo the grid stripe removal process.

In the sixth to 10th embodiments, for example, since the extracted grid stripe components are present as image information, and that image is held, even when grid stripe components are removed from each frame image, the source frame image, i.e., a frame image before grid stripes are removed, may be recovered using the held image information of the grid stripe components.

Grid Stripe Component Removal Process in Sixth to 10th Embodiments

Note that the sixth to 10th embodiments will sometimes be referred to as "this embodiment" together in the following description. Also, a frame image of interest in an X-ray moving image will also be referred to as an "objective image" hereinafter.

For example, components that contain most of the grid stripe components are separated based on the frequency indicated by the grid stripe components, the separated components are processed to obtain feature information that grid stripes may represent, and the processed information is considered as grid stripe components, which are removed from the objective image signal.

The grid stripe components have considerably intense components according to spatial spectrum expression, and can be present around the Nyquist frequency (spatial frequency ½ the sampling frequency) upon sampling if the spatial frequency of grid stripes are appropriately selected. As a result, a state wherein grid stripe components do not overlap major components of a normal image signal can be easily obtained, as shown in FIGS. 42A to 42D.

Only when the objective image signal contains steep variation components, it becomes difficult to separate grid stripe components and the objective image signal, as described previously using FIGS. 43A to 43D.

In some cases, grid stripes themselves may not be present. That is, when an object including a portion that nearly perfectly intercepts X-rays undergoes X-ray radiography or when intense X-rays beyond the dynamic range of a sensor reach a partial region of the sensor, grid stripe components of that region are removed by saturation.

Normally, upon capturing an X-ray image, the X-ray dose outside an object region (through portion) becomes several hundred times that inside the object region since importance is attached to the X-ray dose that is transmitted through the object. In general, it is nonsense to broaden the dynamic range of a sensor or an amplifier for the sensor in consideration of the region outside the object, which has no information. In most cases, the region outside the object exhibits nonlinearity due to saturation, and no grid stripe components are present or the contrast lowers.

Hence, in this embodiment, the present invention can adaptively cope with both a case wherein data for one line includes a steep variation that makes separation of the grid stripe components and the objective image signal difficult, and a case wherein grid stripes themselves are not present, and can remove grid stripe components without generating any artifacts.

Note that the grid stripe component removal process in this embodiment can be explained by applying the grid component removal process for the objective image described in the first to fifth embodiments, and respective explanations and equations associated with that process to each frame image, and a detailed description thereof will be omitted.

Sixth Embodiment

Figure 20:
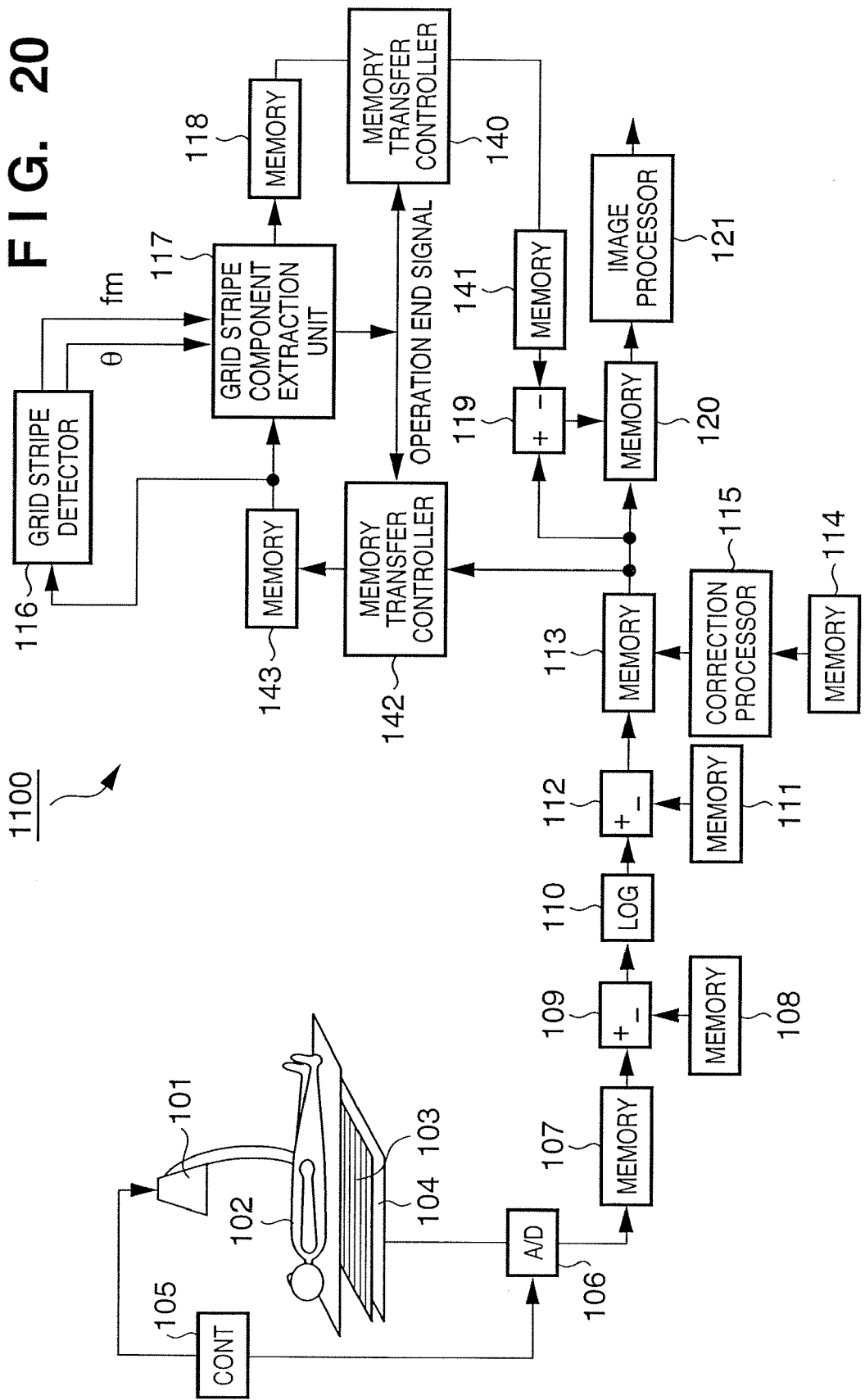
FIG. 20 is a block diagram showing the arrangement of an X-ray image capture apparatus to which the present invention is applied in the sixth embodiment.

The present invention is applied to, e.g., an X-ray image capture apparatus 1100 shown in FIG. 20.

The arrangement of the X-ray image capture apparatus 1100 of this embodiment is different from the X-ray image capture apparatus 100 shown in FIG. 6 in the following respects.

Note that the same reference numerals in the X-ray image capture apparatus 1100 in FIG. 20 denote the same parts as in the X-ray image capture apparatus 100 in FIG. 6, and a detailed description thereof will be omitted. Also, a description of the contents that can be explained by replacing an objective image by a frame image will be omitted.

The X-ray image capture apparatus 1100 of this embodiment is used to capture an X-ray moving image for medical use (for image diagnosis or the like), and comprises a memory 107 for temporarily storing digital data output from an A/D converter 106 as frame image data, an arithmetic device 109 for executing an arithmetic process of the frame image data in the memory 107 using data in a memory 108, a conversion table (to be also referred to as an "LUT" (lookup table) hereinafter) 110 of the frame image data that has undergone the arithmetic process in the arithmetic device 109, as shown in FIG. 20.

Also, the apparatus 1100 comprises an arithmetic device 112 for executing an arithmetic process of the converted frame image data output from the LUT 110 using gain pattern data in a memory 111, and a memory 113 for temporarily storing the frame image data that has undergone the arithmetic process in the arithmetic device 112.

The apparatus 1100 further comprises a correction processor 115 for executing a correction process of the objective image data stored in the memory 113 using information in a memory 114, a memory transfer controller 142 for controlling read of the frame image data in the memory 113 that has undergone the correction process, a memory 143 for storing the frame image data read out from the memory 113 under the control of the memory transfer controller 142, a grid stripe detector 116 for detecting information associated with grid stripes from the frame image data in the memory 143, and a grid stripe component extraction unit 117 for extracting grid stripe components from the frame image data in the memory 143 on the basis of the information obtained by the grid stripe detector 116.

The apparatus 100 further comprises a memory transfer controller 140 for controlling readout of the grid stripe components in a memory 118, a memory 141 for storing the grid stripe components read out from the memory 118 under the control of the memory transfer controller 140, an arithmetic device 119 for subtracting the grid stripe components in the memory 141 from the frame image data in the memory 113, a memory 120 for temporarily storing the arithmetic result of the arithmetic device 119 (the frame image data after the grid stripe components are removed), and an image processor 121 for executing an image process of the objective image data in the memory 120 and outputting the processed image data.

Digital data output from the A/D converter 106 is temporarily stored in the memory 107 as frame image data.

Therefore, the memory 107 stores digital image data (frame image data) as a set of a plurality of pixel data corresponding to a plurality of pixels which form an X-ray sensor 104.

The memory 108 pre-stores digital data which is acquired by photographing while quitting X-ray radiation. This digital data is used to remove offset-like fixed pattern noise unique to the X-ray sensor 104 from the frame image data stored in the memory 107. Therefore, the X-ray image capture apparatus 1100 captures an image while controlling an X-ray generator 101 not to generate X-rays, and stores the captured digital data in the memory 108 as image data.

The arithmetic device 109 executes a process for subtracting pixel data at a given position among a plurality of pixel data which form the image data (image data of fixed pattern noise obtained by photographing without X-ray radiation) stored in the memory 108 from a corresponding one of a plurality of pixel data which form the frame image data (which is obtained by X-rays transmitted through an object 102) stored in the memory 107.

The LUT 110 converts the frame image data that has been processed by the arithmetic device 109 into values proportional to its logarithmic values, and outputs the converted data.

The memory 111 stores gain pattern data used to correct gain variations of pixels which form the X-ray sensor 104 for the frame image data that has been converted by the LUT 110. For this purpose, the X-ray image capture apparatus 1100 makes X-ray radiography without any object 102, removes fixed pattern noise from the image data obtained by that photographing using the digital data stored in the memory 108, and stores data obtained by converting that data into values proportional to logarithmic values by the LUT 110 in the memory 111 as gain pattern data.

The arithmetic device 112 subtracts the gain pattern data in the memory 111 from the frame image data output from the LUT 110 (this process corresponds to division if data to be processed is not logarithmically converted), and outputs the difference data.

The frame image data that has undergone the subtraction process by the arithmetic device 112 is temporarily stored in the memory 113.

The correction processor 115 corrects defective pixel data in a plurality of pixel data which form the frame image data stored in the memory 113 using the defective pixel position information stored in the memory 114, and stores the corrected pixel data at corresponding locations of the memory 113 again.

The memory transfer controller 142 controls readout of the frame image data in the memory 113 (image data that has undergone the correction process of the correction processor 115) on the basis of an operation end signal supplied from the grid stripe component extraction unit 117 (to be described later).

The memory 143 stores the frame image data read out from the memory 113 under the control of the memory transfer controller 142.

The grid stripe detector 116 analyzes grid stripes for the frame image data in the memory 143 (image data that has undergone the correction process by the correction processor 115), and detects and outputs the spatial frequency fm and the angle θ of grid stripes.

The grid stripe component extraction unit 117 reads out the frame image data in the memory 143 (image data that has undergone the correction process by the correction processor 115), and extracts grid stripe components from the readout image data on the basis of the spatial frequency fm and angle θ of grid stripes obtained by the grid stripe detector 116. After that, the unit 117 outputs an operation end signal indicating the end of the extraction process to the memory transfer controllers 142 and 140.

The grid stripe components extracted by the grid stripe component extraction unit 117 are temporarily stored in the memory 118.

The memory transfer controller 140 controls readout of the grid stripe components in the memory 118 on the basis of the operation end signal supplied from the grid stripe component extraction unit 117.

The memory 141 stores the grid stripe components read out from the memory 118 under the control of the memory transfer controller 140.

The arithmetic device 119 subtracts the grid stripe components stored in the memory 141 from the frame image data in the memory 113 (image data that has undergone the correction process by the correction processor 115).

The frame image data after the grid stripe components are subtracted by the arithmetic device 119 is temporarily stored in the memory 120.

The image processor 121 executes an image process of the frame image data in the memory 120 to allow easy observation by the observer.

Note that the image process includes, for example, the following processes:
a removal process of random noise from a frame image;
a process for converting tone or emphasizing details to obtain density values that the observer is easy to see upon displaying a frame image; and
a process for reducing the information size of a frame image by cutting out a portion unnecessary for the observer from a frame image, or compressing frame image information.

The frame image data that has been processed by the image processor 121 then undergoes a display process on a display unit, a storage process in a storage unit or storage medium, an analysis process, or the like by arbitrary means (not shown) in an external apparatus or the X-ray image capture apparatus 1100.

<Arrangement and Operation as Characteristic Feature of X-ray Image Capture Apparatus 1100>

Figure 21:
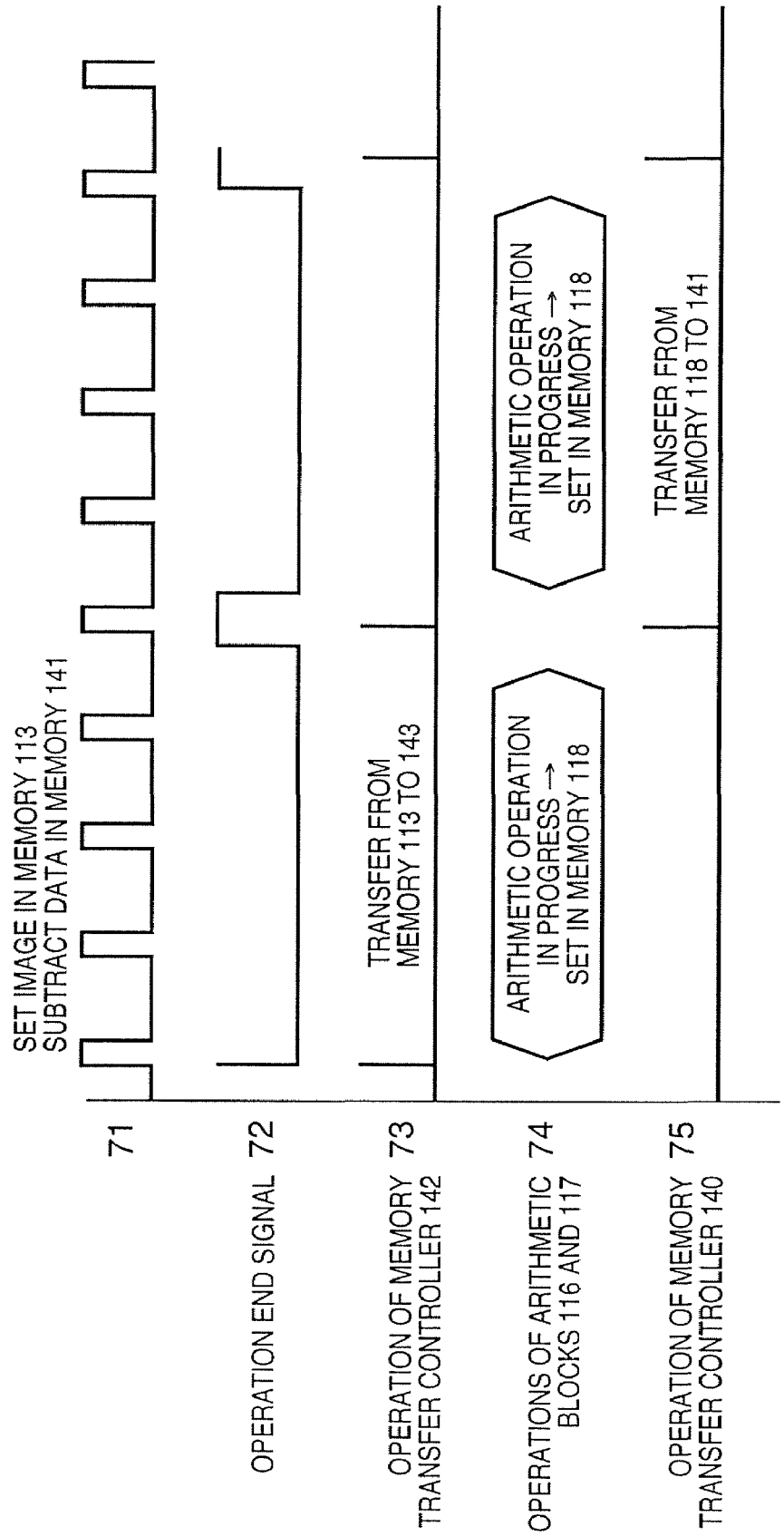
FIG. 21 is a timing chart for explaining the operation timing of the X-ray image capture apparatus.

71 to 75 in FIG. 21 are illustrated in consideration of the data read timings of the memory transfer controllers 140 and 142 and the processing timings of the readout data in the X-ray image capture apparatus 1100.

71 in FIG. 21 indicates the storage timings of frame image data, which are captured in turn by the X-ray sensor 104, in the memory 113. The frame image data which are stored in turn in the memory 113 undergo the removal process of grid stripe components in the memory 141 by the arithmetic device 119.

72 in FIG. 21 indicates an operation end signal output from the grid stripe component extraction unit 117. As indicated by 72 in FIG. 21, the operation end signal indicates the end of extraction of grid stripe components (the end of arithmetic operations) when it is at high level.

73 in FIG. 21 indicates the operation timings of the memory transfer controller 142 based on the operation end signal output from the grid stripe component extraction unit 117. As indicated by 73 in FIG. 21, if it is determined based on the operation end signal from the grid stripe component extraction unit 117 that the grid stripe component extraction end timing has been reached (if the operation end signal is at high level), the memory transfer controller 142 reads out frame image data in the memory 113 to the memory 143.

74 in FIG. 21 indicates the operation timings of the grid stripe detector 116 and grid stripe component extraction unit 117. As indicated by 74 in FIG. 21, when frame image data is transferred to the memory 143, the grid stripe detector 116 and grid stripe component extraction unit 117 operate, and grid stripe components obtained as a result of the operation are stored in the memory 118. At the end timing of this operation, the grid stripe component extraction unit 117 outputs the high-level operation end signal, as indicated by 72 in FIG. 21.

75 in FIG. 21 indicates the operation timing of the memory transfer controller 140 on the basis of the operation end signal output from the grid stripe component extraction unit 117. As indicated by 75 in FIG. 21, if it is determined based on the operation end signal from the grid stripe component extraction unit 117 that the grid stripe component extraction end timing has been reached (if the operation end signal is at high level), the memory transfer controller 140 reads out grid stripe components in the memory 118 to the memory 141. In this way, the grid stripe components in the memory 141 are updated.

That is, in this embodiment, as indicated by 71 to 75 in FIG. 21, the grid stripe component extraction process is executed not for all frame images which form the X-ray moving image, but the next grid stripe component extraction process is executed at the end timing of grid stripe component extraction process for one frame image, and frame images between these frames undergo a grid stripe component removal process using the previously extracted identical grid stripe components (those stored in the memory 141). Such operation is effective since successive frame images have nearly the same positions of the X-ray generator 110, its X-ray energy, the position of the object 102, and the like, and stripe components formed by the grid 103 are nearly the same.

In this embodiment, the frame image which is to undergo the next extraction process is stored in the memory 143 at the end timing of the grid stripe component extraction process for one frame image. However, the present invention is not limited to such specific timing. For example, another arbitrary timing control mechanism may be used to periodically store a frame image in the memory 143, and that frame image may undergo the grid stripe component extraction process.

In this embodiment, the object to be processed is an X-ray moving image. For example, a still image may be used as the object to be processed, and previously extracted grid stripe components may be used in the grid stripe component removal process for the currently captured still image. In this case as well, the load on extraction of grid stripe components can be reduced.

<Another Detailed Arrangement and Operation of X-ray Image Capture Apparatus 1100>

The following building components which additionally require detailed descriptions in the aforementioned X-ray image capture apparatus 1100 will be described in detail below.

(1) Image data of grid stripe components stored in memory 118

(2) Correction process of defective pixels by correction processor 115

(3) Detection & extraction processes of grid stripe components by grid stripe detector 116 and grid stripe component extraction unit 117

(1) Image Data of Grid Stripe Components Stored in Memory 118

The image data of grid stripe components stored in the memory 118 is to be subtracted from the frame image data on which grid stripe components are superposed. If the data stored in the memory 118 is separately stored in correspondence with the objective image data after subtraction like in this embodiment, the source frame image data on which grid stripe components are superposed can be recovered from the frame image data from which grid stripes have been removed. In this way, even when the frame image data is damaged by some troubles in a grid removal process, the source frame image data can be recovered by the recovery process.

(2) Correction Process of Defective Pixels by Correction Processor 115

The correction processor 115 executes a process to be described below by, e.g., software using a microprocessor.

Note that the examples of pixel defect distributions in the X-ray sensor 104 are the same as those in the first to fifth embodiments, and a detailed description thereof will be omitted.

(3) Detection & Extraction Processes of Grid Stripe Components by Grid Stripe Detector 116 and Grid Stripe Component Extraction Unit 117

The grid stripe detector 116 reads out some of the frame image data stored in the memory 113, checks the spectrum of grid stripes contained in the frame image data based on the readout data, and detects the spatial frequency fm and angle θ of the grid stripes. The subsequent grid stripe component extraction unit 117 uses the information of the spatial frequency fm and angle θ (to be also referred to as "angle η" hereinafter) of the grid stripes in a grid stripe component extraction process.

Note that the detection process of the spatial frequency fm and angle θ of grid stripes and the flow chart associated with that process have contents that can be explained by replacing the objective image described in the first to fifth embodiments by a frame image, and a detailed description thereof will be omitted.

Seventh Embodiment

Figure 22:
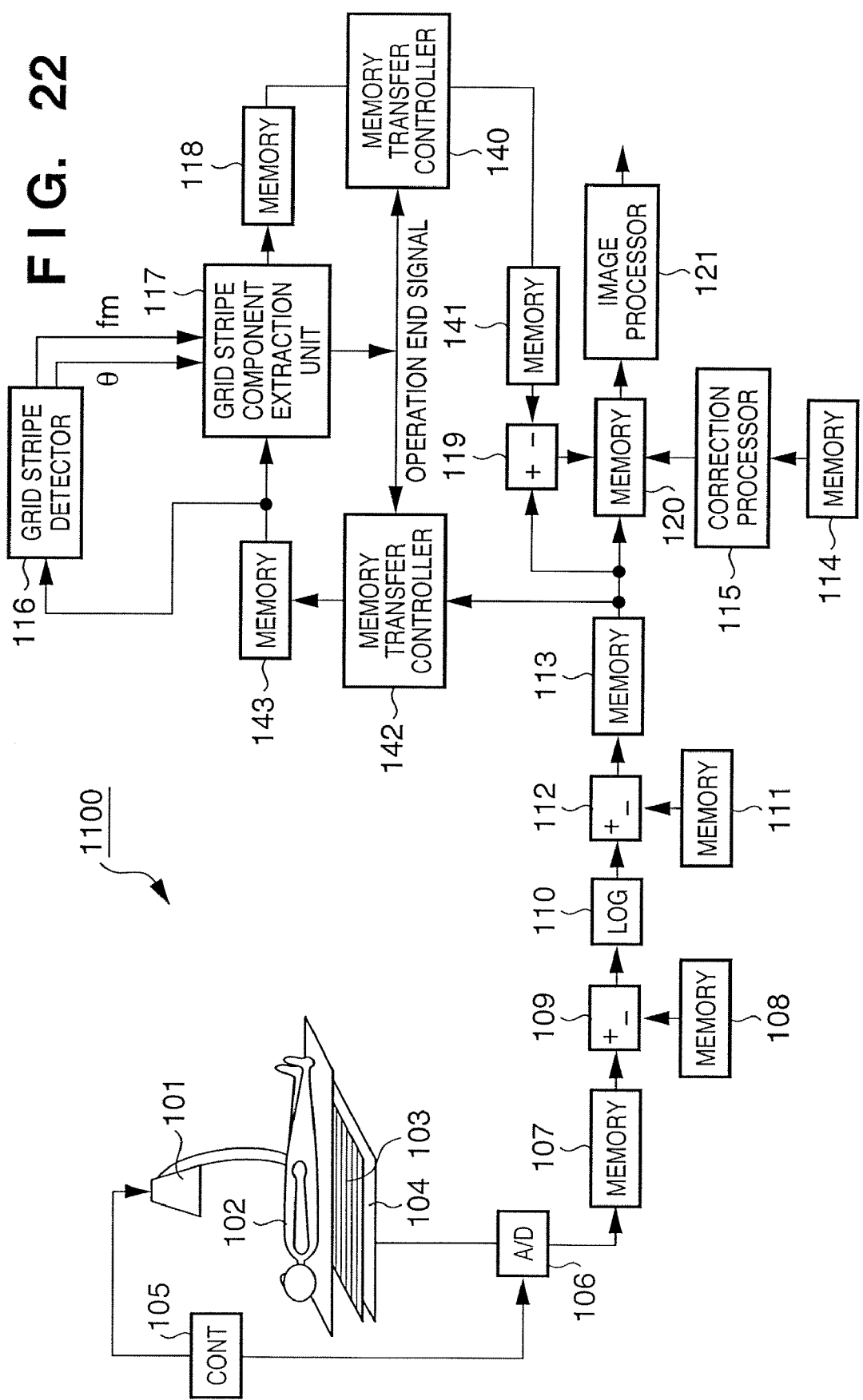
FIG. 22 is a block diagram showing the arrangement of an X-ray image capture apparatus to which the present invention is applied in the seventh embodiment.

The present invention is applied to, e.g., an X-ray image capture apparatus 1400 shown in FIG. 22.

The arrangement of the X-ray image capture apparatus 1400 of this embodiment is different from the X-ray image capture apparatus 1100 shown in FIG. 20 in the following respects.

Note that the same reference numerals in the X-ray image capture apparatus 1400 in FIG. 22 denote the same parts as in the X-ray image capture apparatus 1100 in FIG. 20, and a detailed description thereof will be omitted.

In the X-ray image capture apparatus 1100 in FIG. 20, the correction processor 115 executes the defective pixel correction process using data in the memory 114 for the frame image data in the memory 113. By contrast, in the X-ray image capture apparatus 1400 of this embodiment, as shown in FIG. 22, the correction processor 115 executes the defective pixel correction process using data in the memory 114 for the frame image data in the memory 120, i.e., for the frame image data after the grid stripe components have been removed.

Therefore, according to the X-ray image capture apparatus 1400 of this embodiment, since the need for pixel defect correction that takes grid stripes into account is obviated, conventional, simple defective pixel correction, which corrects defective pixels using the average value of surrounding non-defective pixel values, can be applied.

Eighth Embodiment

Figure 23:
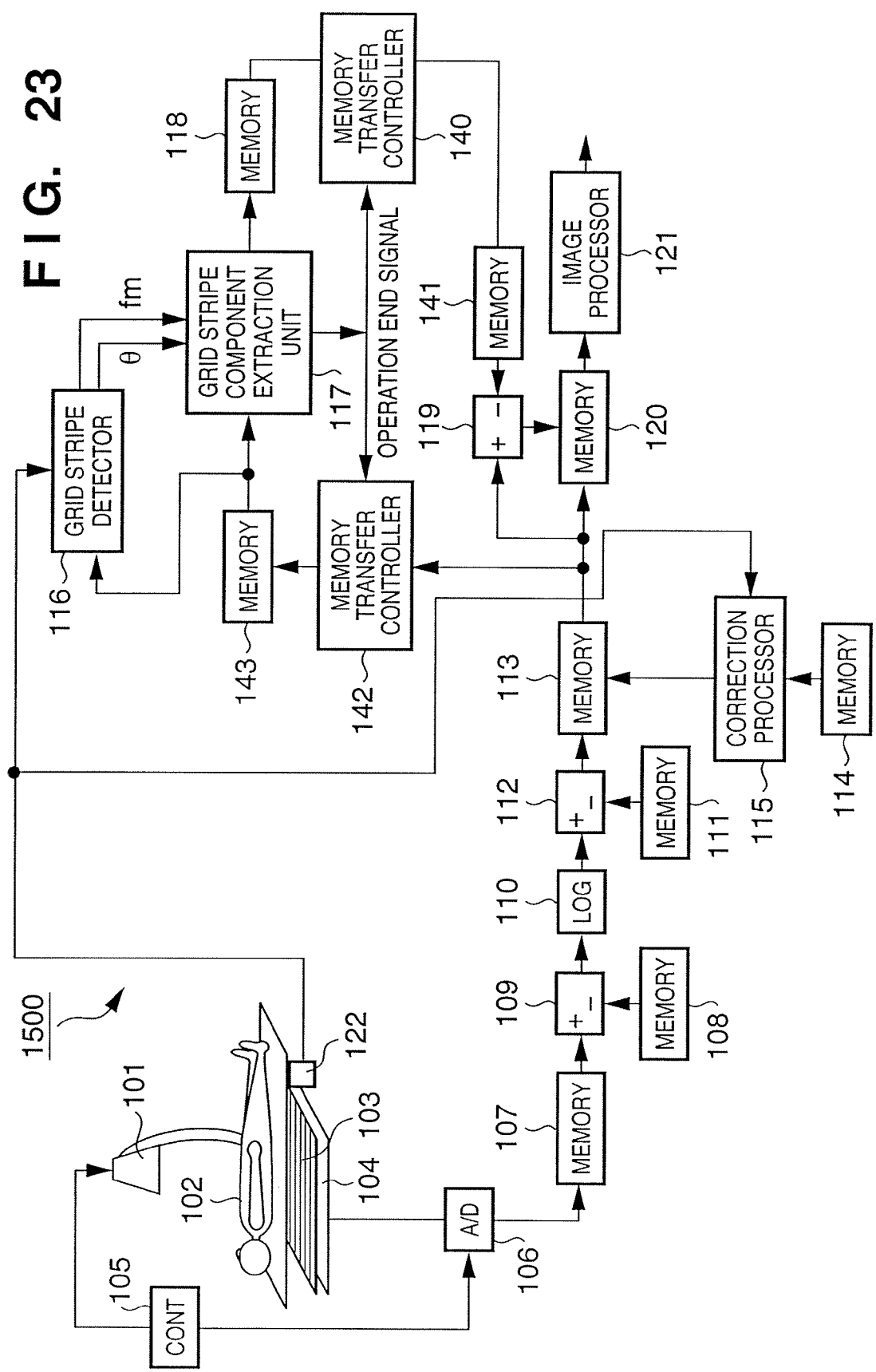
FIG. 23 is a block diagram showing the arrangement of an X-ray image capture apparatus to which the present invention is applied in the eighth embodiment.

The present invention is applied to, e.g., an X-ray image capture apparatus 1500 shown in FIG. 23.

The arrangement of the X-ray image capture apparatus 1500 of this embodiment is different from the X-ray image capture apparatus 1100 shown in FIG. 20 in the following respects.

Note that the same reference numerals in the X-ray image capture apparatus 1500 in FIG. 23 denote the same parts as in the X-ray image capture apparatus 1100 in FIG. 20, and a detailed description thereof will be omitted.

The X-ray image capture apparatus 1500 of this embodiment has a detector (switch) 122 for detecting attachment of the grid 103 in addition to the arrangement of the X-ray image capture apparatus 1100 in FIG. 20, as shown in FIG. 23.

The detector 122 supplies the detection result (grid attachment signal) of attachment of the grid 103 to the correction processor 115 and grid stripe detector 116.

When it is detected based on the grid attachment signal from the detector 122 that the grid 103 is attached, the correction processor 115 executes a defective pixel correction process that considers grid stripes, as has been explained in the first embodiment. Otherwise, the correction processor 115 corrects defective pixels using, e.g., the average value of surrounding non-defective pixel values.

Likewise, when it is detected based on the grid attachment signal from the detector 122 that the grid 103 is attached, the grid stripe detector 116 executes a grid stripe detection process (analysis process), as has been explained in the first embodiment. However, when it is detected based on the grid attachment signal that the grid 103 is not attached, the grid stripe detector 116 skips the grid stripe detection process, immediately determines the absence of grid stripes, and executes a corresponding process.

As described above, since the X-ray image capture apparatus 1500 of this embodiment has the detector 122 and detects grid stripes based on the detection result of the detector 122, the time required for the process for detecting grid stripes can be greatly shortened.

Ninth Embodiment

Figure 24:
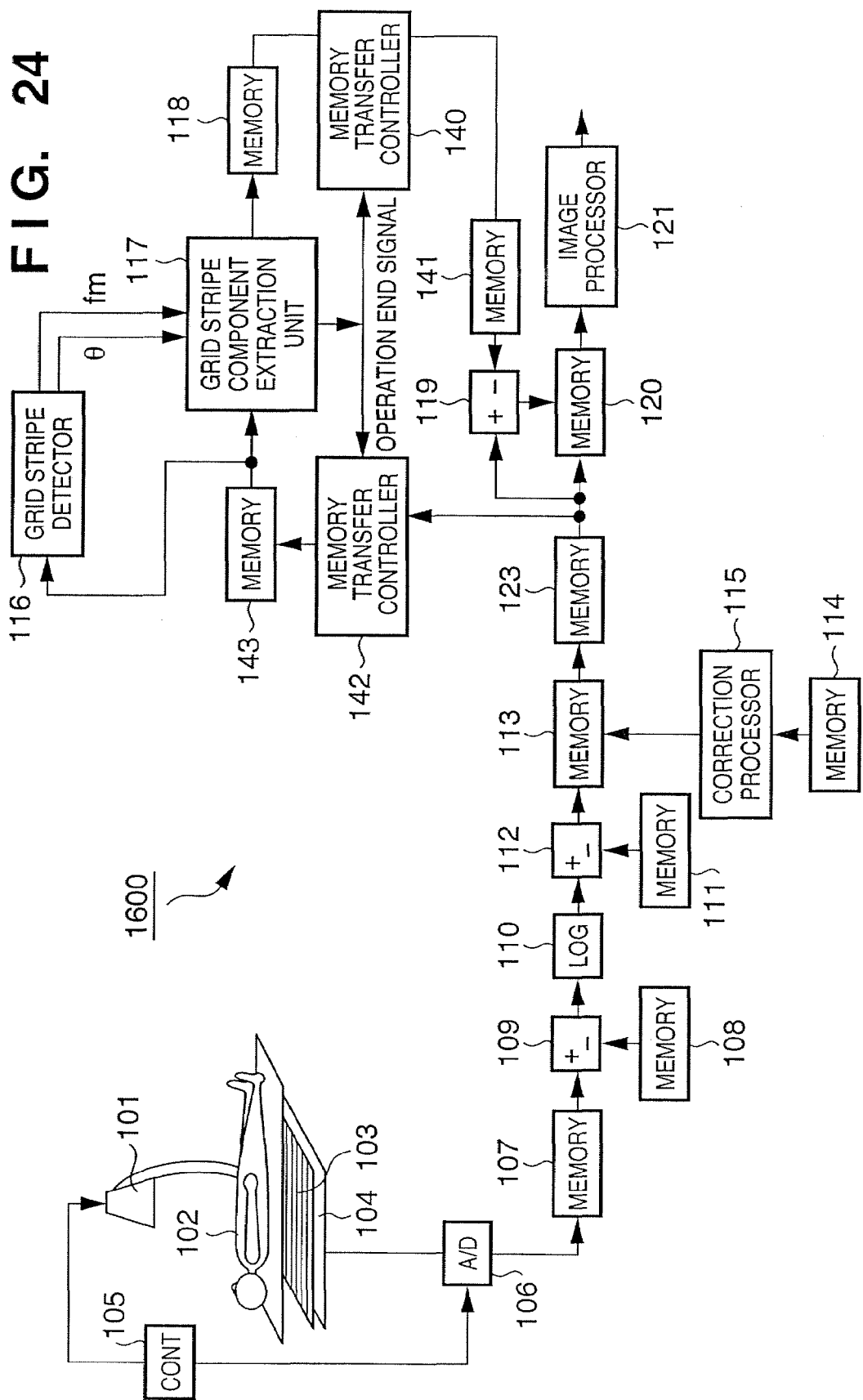
FIG. 24 is a block diagram showing the arrangement of an X-ray image capture apparatus to which the present invention is applied in the eighth embodiment.

The present invention is applied to, e.g., an X-ray image capture apparatus 1600 shown in FIG. 24.

The arrangement of the X-ray image capture apparatus 1600 of this embodiment is different from the X-ray image capture apparatus 1100 shown in FIG. 20 in the following respects.

Note that the same reference numerals in the X-ray image capture apparatus 1600 in FIG. 24 denote the same parts as in the X-ray image capture apparatus 1100 in FIG. 20, and a detailed description thereof will be omitted.

The X-ray image capture apparatus 1600 of this embodiment further comprises a memory 123 for storing X-ray irradiated region data in addition to the arrangement of the X-ray image capture apparatus 1100 in FIG. 20, as shown in FIG. 24.

The memory 123 stores image data (irradiated region data) obtained by extracting only a region irradiated with X-rays from the frame image data stored in the memory 113, and the irradiated region data in the memory 123 undergo detection and extraction of grid stripe components.

More specifically, in X-ray radiography, it is a common practice to provide an irradiation field stop to the exit of an X-ray generation bulb of the X-ray generator 101 so as to avoid a portion other than a target portion of the object 102 (human body in this case) from being exposed. With this field stop, only the required portion of the object 102 can be irradiated with X-rays.

When the irradiation field stop function is used, not all image signals obtained from the X-ray sensor 104 are effective but only a partial image corresponding to an X-ray irradiation field defined by the irradiation field stop is effective in an image obtained by X-ray radiography.

Hence, in this embodiment, a computer means (CPU or the like; not shown) detects an effective partial image region (irradiated region) corresponding to the X-ray irradiation field from the frame image data in the memory 113 on the basis of the X-ray intensity distribution and stop shape, or other information, and stores only the data of that irradiated region (irradiated region data) in the memory 123.

As described above, since this embodiment processes only the irradiated region data in the memory 123, i.e., not all objective image data but only data of the required portion with the reduced information size, the processing time can be shortened.

In this embodiment, the irradiated region is extracted from the frame image after defective pixel correction. For example, after the irradiated region is extracted, defective pixel correction may be executed for that irradiated region.

10th Embodiment

In the X-ray image capture apparatus 1100 in FIG. 20 of the sixth embodiment, the grid stripe component extraction process of the grid stripe component extraction unit 117 is executed according to the flow chart shown in FIGS. 14A and 14B, as in the first embodiment.

In this embodiment, the grid stripe component extraction process of the grid stripe component extraction unit 117 can be executed according to the flow chart shown in, e.g., FIGS. 18A and 18B, as in the fifth embodiment. In this case, the image to be processed is not an objective image described in the fifth embodiment but a frame image.

11th Embodiment

In the above embodiment, when the grid is moved in a direction perpendicular to stripes, the moving distance or speed of the grid must be adjusted in correspondence with the X-ray exposure time. That is, when the exposure time is very long, the grid approaches or reaches the limit of the moving distance, and the movement of the grid is slowed down or stopped at that time. On the other hand, when the exposure time is very short, if the grid moving speed is low, a moving distance large enough to remove the grid stripe pattern cannot be obtained. In either case, grid stripes remain superposed on an image.

In the following 11th to 15th embodiments, a radiation image processing apparatus, image processing system, radiation image processing method, storage medium, and program, which can obtain a high-quality radiation moving image from which image components caused by a grid have been removed from a radiation image captured by radiography using the moving grid will be explained.

Figure 25:
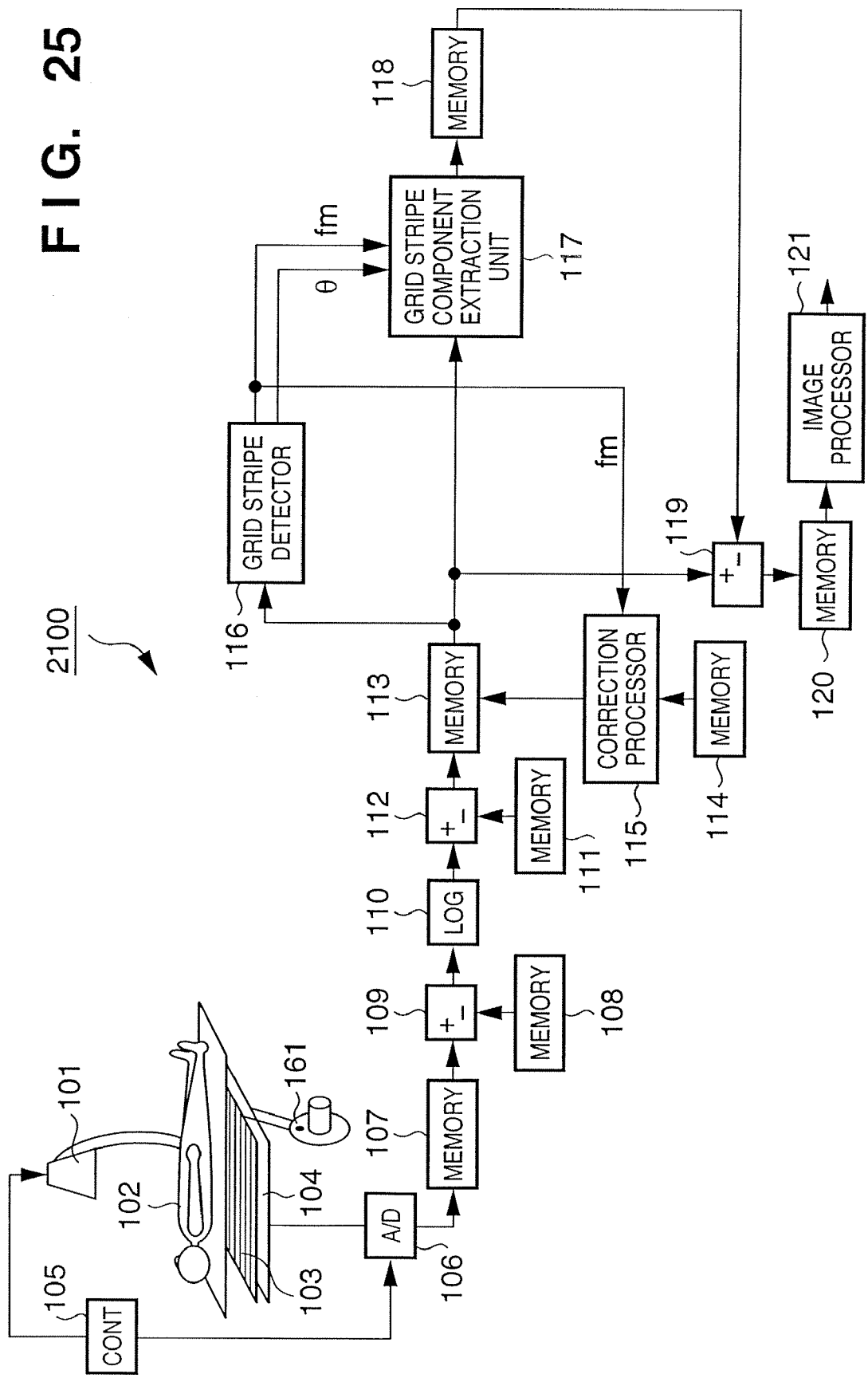
FIG. 25 is a block diagram showing the arrangement of an X-ray image capture apparatus to which the present invention is applied in the 11th embodiment.

The present invention is applied to, e.g., an X-ray image capture apparatus 2100 shown in FIG. 25.

The arrangement of the X-ray image capture apparatus 2100 of this embodiment is different from the X-ray image capture apparatus 100 shown in FIG. 6 in the following respects.

Note that the X-ray image capture apparatus 2100 in FIG. 25 has the same building components as those of the X-ray image capture apparatus 100 in FIG. 6, except for signal connections among these building components. Also, a detailed description of building components which have the same functions as those in the X-ray image capture apparatus 100 in FIG. 6 will be omitted.

<Overall Arrangement and Operation of X-ray Image Capture Apparatus 2100>

The X-ray image capture apparatus 2100 of this embodiment is used to capture an X-ray image for medical use (for image diagnosis or the like), and comprises a grid 103 which is set to have a structure that allows movement in a direction perpendicular to grid stripes and is used to remove scattered X-rays from an object 102, as shown in FIG. 25.

Reference numeral 161 denotes a motor·encoder·cam mechanism for moving the grid 103, and the cam mechanism has a function of converting the rotation of the motor into rectilinear motion (translation) of the grid 103.

A grid stripe detector 116 analyzes grid stripes for objective image data in a memory 113 (image data after a division process of an arithmetic device 112) to detect and output a spatial frequency fm and angle θ of grid stripes. The grid stripe detector 116 outputs fm=0 if no grid stripes are extracted.

A correction processor 115 corrects defective pixel data in a plurality of pixel data which form the objective image data stored in a memory 113 using defective pixel position information stored in a memory 114, and stores the corrected pixel data at corresponding locations of the memory 113 again. This correction processor 115 receives data fm indicating the presence of remaining grid stripes from the grid stripe analysis block of the grid stripe detector 116, and executes a special process if it determines the presence of grid stripes.

Grid stripe components obtained by a grid stripe component extraction unit 117 are temporarily stored in a memory 118. When the grid 103 operates normally and no significant grid stripe information is detected by the grid stripe detector 116, "0" is stored in the memory 118.

Image data of the grid stripe components stored in the memory 118 is obtained by subtraction from objective image data on which remaining grid stripe components are superposed. Since that image data is separately stored in the memory 118 like in this embodiment, source objective image data on which grid stripe components are superposed can be recovered from the objective image data from which grid stripes have been removed. In this way, even when the objective image data is damaged by some troubles in a grid removal process, the source objective image data can be recovered by the recovery process.

Figure 26:
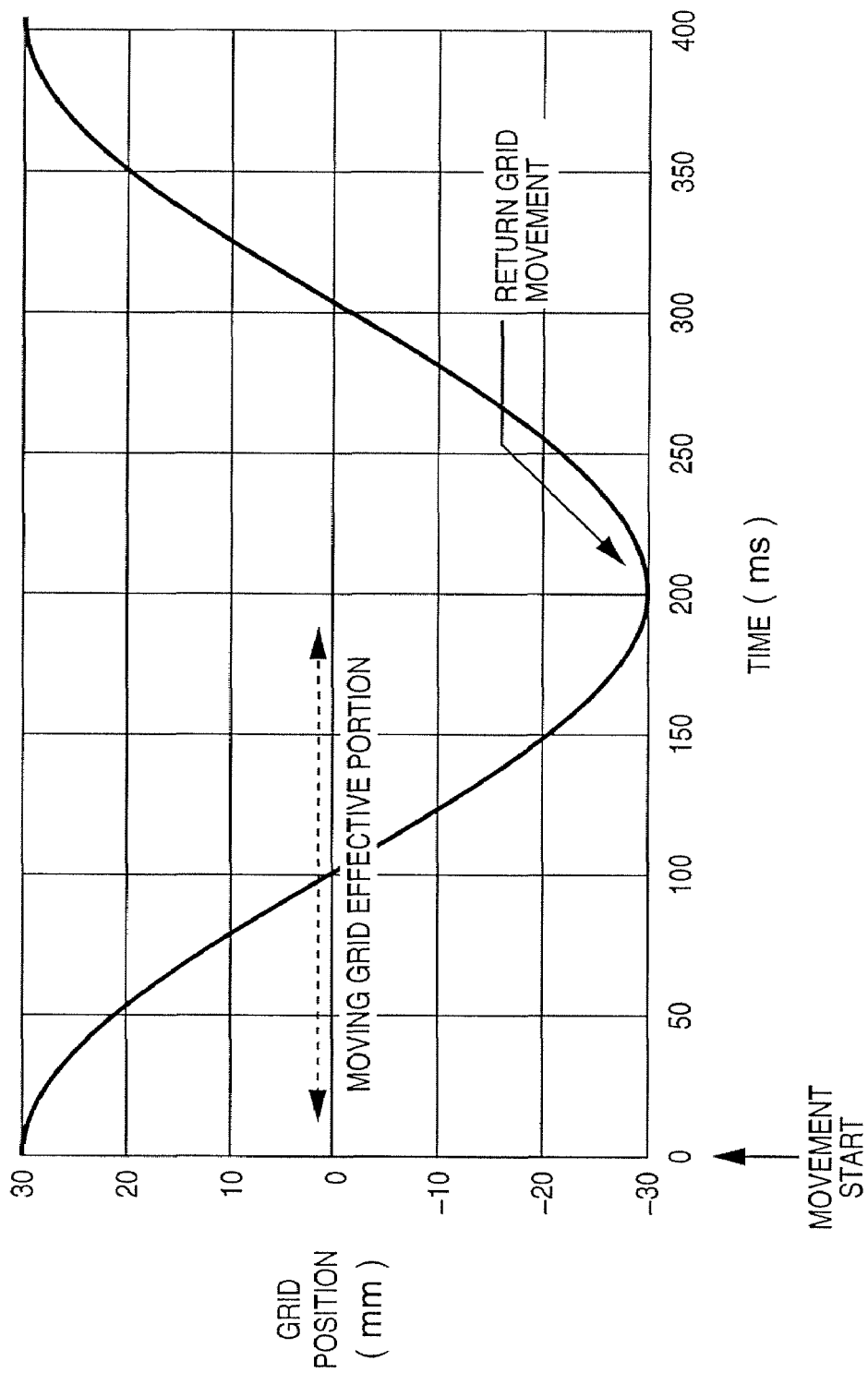
FIG. 26 is a graph showing an example of the relationship between the grid moving distance (position) and time.

In actual photographing, the grid 103 is moved by the motor·encoder·cam mechanism 161. FIG. 26 shows an example of the relationship between the moving distance (position) of the grid 103 and time. In FIG. 26, the abscissa plots time. Movement starts from a timing "0", and a portion where the time and position have nearly the linear relationship is indicated by "moving grid effective portion". That is, the apparatus of this embodiment monitors the encoder output, and controls a controller 105 to generate X-rays and an A/D converter 106 to acquire image data during a period in which the moving distance of the grid 103 becomes nearly constant, i.e., "moving grid effective portion".

Normally, upon photographing a human body, since the X-ray exposure time is approximately prescribed in correspondence with a portion to be photographed, the motor·encoder·cam mechanism 161 is controlled to have a low driving speed if the exposure time is long or a high driving speed if the exposure time is short, thereby preventing grid stripes from being always printed on an image.

In practice, due to an operator's setup error of a portion to be photographed, the moving distance of the grid 103 often becomes too short or long with respect to the X-ray exposure time. If the moving distance of the grid 103 is too short, grid stripes are not averaged. If the moving distance of the grid 103 is too long, the motor·encoder·cam mechanism 161 rotates many times, and the grid moving speed becomes gradually low. After the grid stops at a given timing, it is reversed. In this case, when the speed becomes low or when the grid stops, grid stripes are superposed on an image without being averaged.

In such case, in the present invention, the grid stripe detector 116 detects grid stripe information, and a grid stripe removal process is executed only when grid stripes are detected.

<Detailed Arrangement and Operation of X-ray Image Capture Apparatus 100>

The following building components which require detailed descriptions in the aforementioned X-ray image capture apparatus 2100 will be described in detail below.

(1) Correction process of defective pixels by correction processor 115

(2) Detection & extraction processes of grid stripe components by grid stripe detector 116 and grid stripe component extraction unit 117

(1) Correction Process of Defective Pixels by Correction Processor 115

The correction processor 115 executes a process to be described below by, e.g., software using a microprocessor.

The correction processor 115 corrects defective pixels based on defective pixel position information obtained from the memory 114. Normally, when the grid 103 operates normally, "fm=0" is output from the grid stripe detector 116, and defective pixel correction is implemented based on the average value of surrounding non-defective pixel values.

However, when grid stripes remain and fm≠0, defect correction using the average cannot be made, and predictive correction is required, as has been explained previously. This predictive correction will be explained below.

Note that the examples of pixel defect distributions in an X-ray sensor 104 are the same as those in the first to fifth embodiments, and a detailed description thereof will be omitted.

(2) Detection & Extraction Processes of Grid Stripe Components by Grid Stripe Detector 116 and Grid Stripe Component Extraction Unit 117

Note that the detection process of the spatial frequency fm and angle θ of grid stripes and the flow chart associated with that process have the same contents as those described in the first to fifth embodiments, and a detailed description thereof will be omitted.

12th Embodiment

Figure 27:
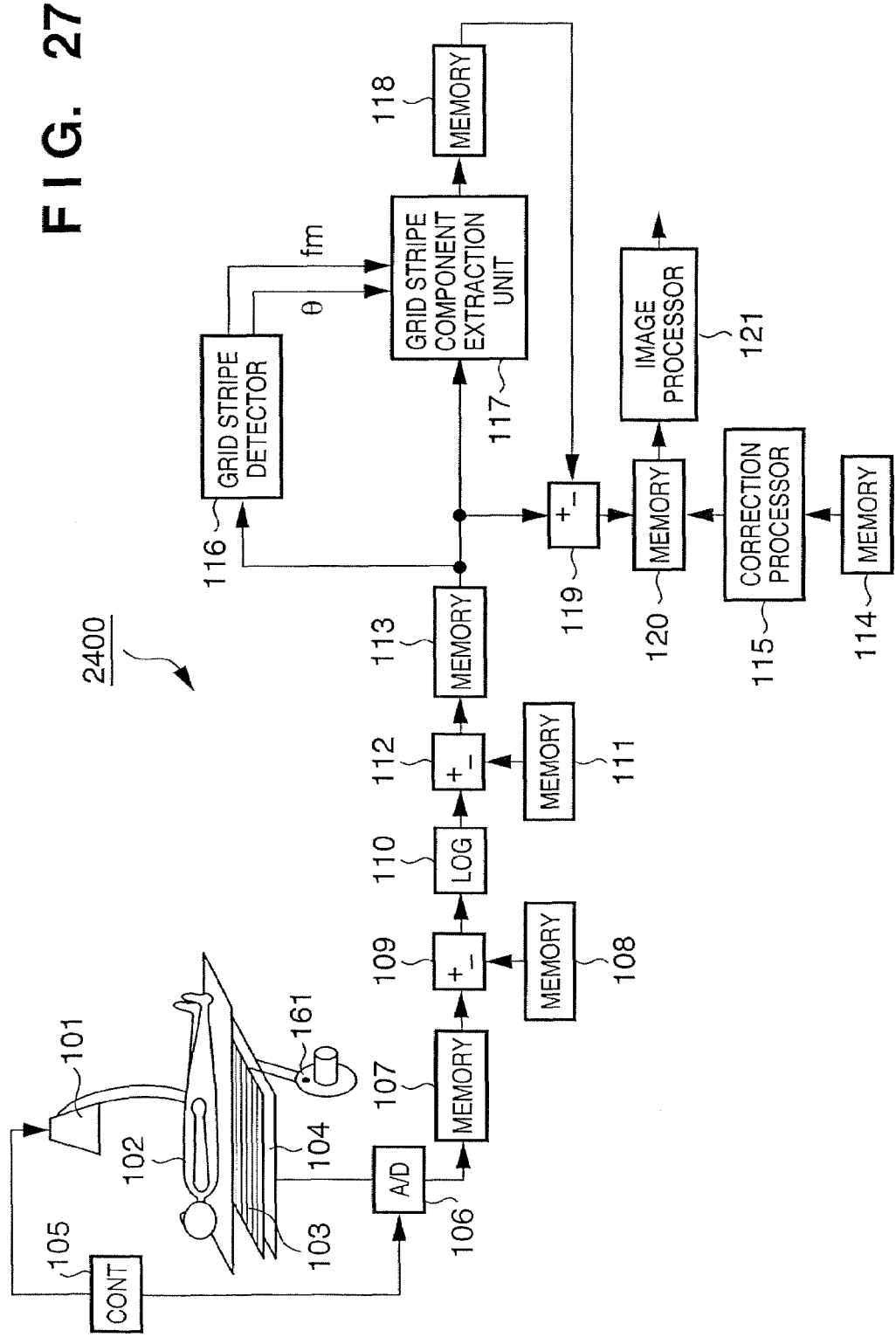
FIG. 27 is a block diagram showing the arrangement of an X-ray image capture apparatus to which the present invention is applied in the 12th embodiment.

The present invention is applied to, e.g., an X-ray image capture apparatus 2400 shown in FIG. 27.

The arrangement of the X-ray image capture apparatus 2400 of this embodiment is different from the X-ray image capture apparatus 2100 shown in FIG. 25 in the following respects.

Note that the same reference numerals in the X-ray image capture apparatus 2400 in FIG. 27 denote the same parts as in the X-ray image capture apparatus 2100 in FIG. 25, and a detailed description thereof will be omitted.

In the X-ray image capture apparatus 2100 in FIG. 25, the correction processor 115 executes the defective pixel correction process using data in the memory 114 for the objective image data in the memory 113. By contrast, in the X-ray image capture apparatus 2400 of this embodiment, as shown in FIG. 27, the correction processor 115 executes the defective pixel correction process using data in the memory 114 for objective image data in a memory 120, i.e., for the objective image data after the grid stripe components have been removed.

Therefore, according to the X-ray image capture apparatus 2400 of this embodiment, since the need for pixel defect correction that takes grid stripes into account is obviated, conventional, simple defective pixel correction, which corrects defective pixels using the average value of surrounding non-defective pixel values, can be applied.

13th Embodiment

Figure 28:
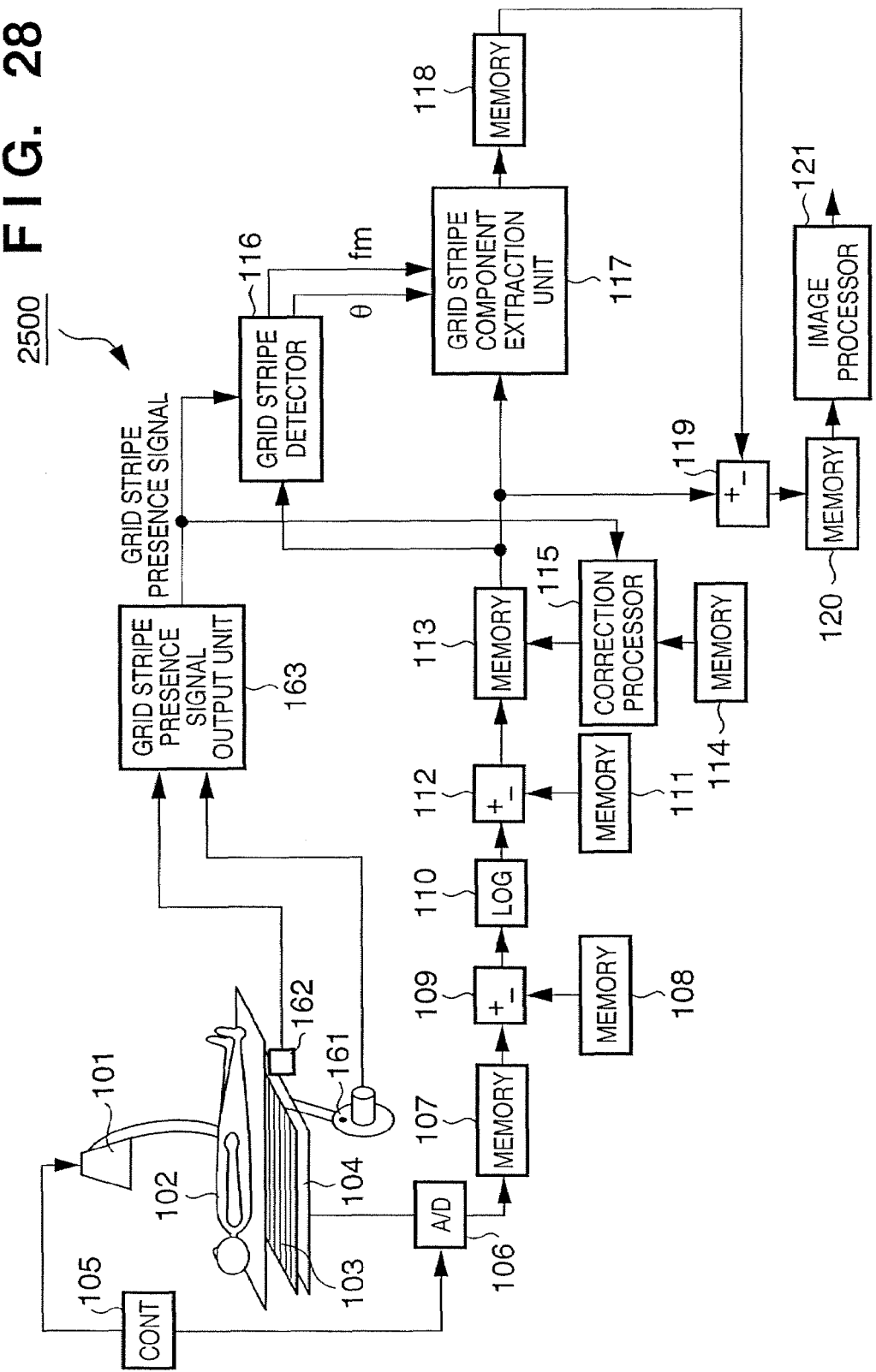
FIG. 28 is a block diagram showing the arrangement of an X-ray image capture apparatus to which the present invention is applied in the 13th embodiment.

The present invention is applied to, e.g., an X-ray image capture apparatus 2500 shown in FIG. 28.

The following arrangement of the X-ray image capture apparatus 2500 of this embodiment is different from the X-ray image capture apparatus 2100 shown in FIG. 25.

Note that the same reference numerals in the X-ray image capture apparatus 2500 in FIG. 28 denote the same parts as in the X-ray image capture apparatus 2100 in FIG. 25, and a detailed description thereof will be omitted.

The X-ray image capture apparatus 2500 of this embodiment comprises a grid stripe presence signal output mechanism or unit 163, which monitors the output from a monitor mechanism 162 that, in turn, monitors X-ray exposure and the encoder output from a motor·encoder·cam mechanism 161, and outputs a signal indicating if grid stripes are present on the basis of the relationship between the X-ray exposure time and the moving distance of the grid 103, which is estimated from the encoder output, to the grid stripe detector 116 and correction processor 115, in addition to the arrangement of the X-ray image capture apparatus 2100 shown in FIG. 25, as shown in FIG. 28.

Furthermore, the apparatus also comprises a mechanism (not shown) for making X-ray exposure until a predetermined integral value is obtained by an independently arranged device called a phototimer for monitoring the integral value of the X-ray dose that has been transmitted through an object.

With such phototimer function, the X-ray exposure time can be automatically adjusted in correspondence with the X-ray dose that has been transmitted through an object without pre-setting a portion to be photographed.

However, in this case, since the X-ray exposure time is unpredictable, the moving speed of the grid 103 cannot be set in advance. In such case, the grid 103 is moved at an average moving speed.

In this embodiment, the X-ray exposure time and moving distance of the grid 103 can be measured by the monitor mechanism 162 and motor·encoder·cam mechanism 161. In another method, since the moving speed of the grid 103 is constant, the moving distance of the grid 103 can be measured by monitoring only the X-ray exposure time.

The grid stripe presence signal output unit 163 outputs a grid stripe presence signal indicating the presence of grid stripes when the moving distance of the grid 103 is too short or long with respect to the X-ray exposure time.

Upon receiving the grid stripe presence signal from the grid stripe presence signal output unit 163, the correction processor 115 executes a defective pixel correction process that considers grid stripes, as has been explained in the 11th embodiment. Otherwise, the correction processor 115 corrects defective pixels using, e.g., the average value of surrounding non-defective pixel values.

The grid stripe detector 116 analyzes grid stripes only when it receives the grid stripe presence signal from the grid stripe presence signal output unit 163. When the grid stripe detector 116 does not receive any grid stripe presence signal, it does not analyze grid stripes, and immediately determines the absence of grid stripes.

As described above, since the X-ray image capture apparatus 2500 of this embodiment has the grid stripe presence signal output unit 163 and detects grid stripes based on the grid stripe presence signal output from the grid stripe presence signal output unit 163, the time required for the process for detecting grid stripes can be greatly shortened.

14th Embodiment

Figure 29:
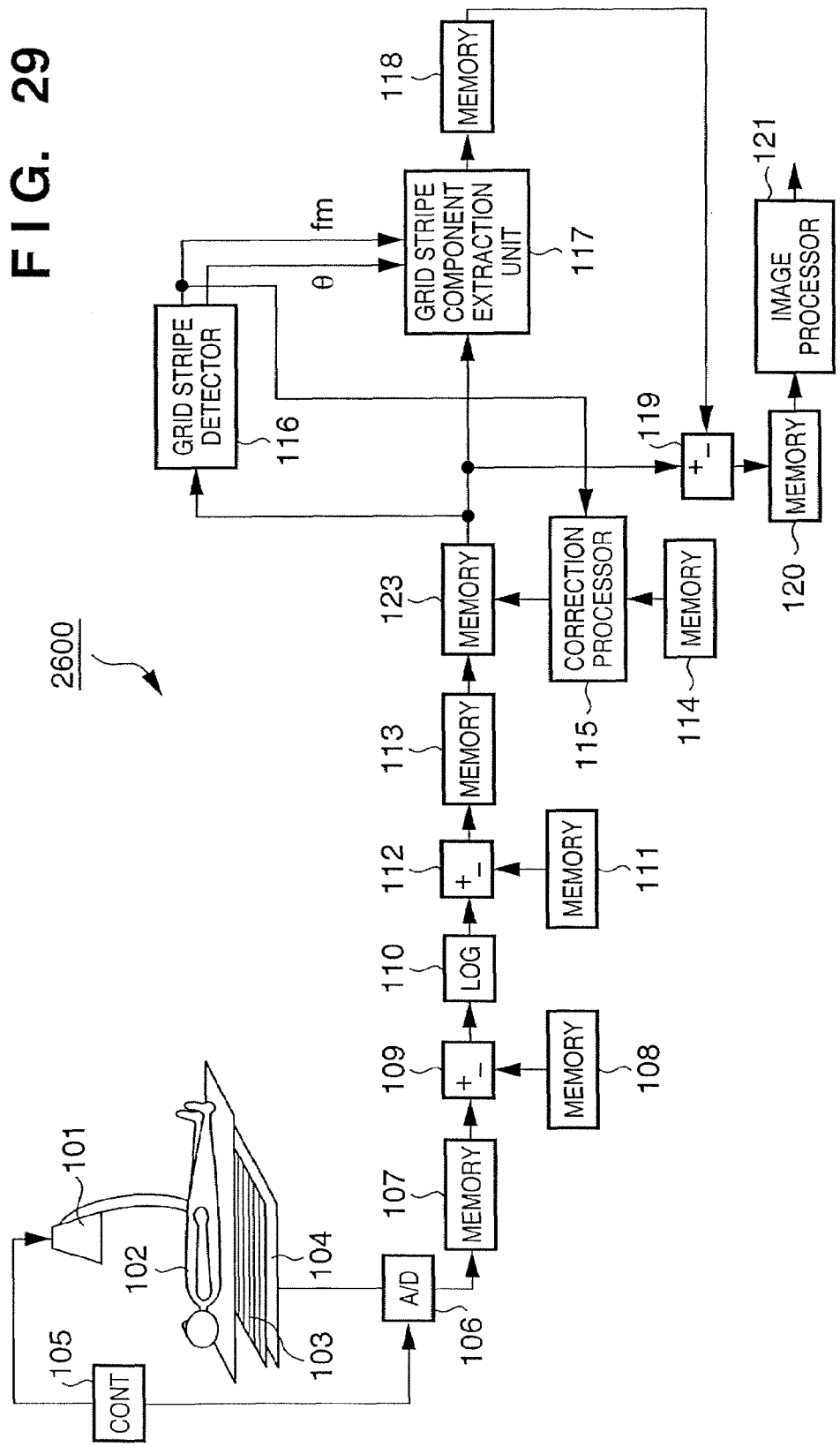
FIG. 29 is a block diagram showing the arrangement of an X-ray image capture apparatus to which the present invention is applied in the 14th embodiment.

The present invention is applied to, e.g., an X-ray image capture apparatus 2600 shown in FIG. 29.

The arrangement of the X-ray image capture apparatus 2600 of this embodiment is different from the X-ray image capture apparatus 2100 shown in FIG. 25 in the following respects.

Note that the same reference numerals in the X-ray image capture apparatus 2600 in FIG. 29 denote the same parts as in the X-ray image capture apparatus 2100 in FIG. 25, and a detailed description thereof will be omitted.

The X-ray image capture apparatus 2600 of this embodiment further comprises a memory 123 for storing X-ray irradiated region data in addition to the arrangement of the X-ray image capture apparatus 2100 in FIG. 25, as shown in FIG. 29.

The memory 123 stores image data (irradiated region data) obtained by extracting only a region irradiated with X-rays from the objective image data stored in the memory 113, and the irradiated region data in the memory 123 undergo detection and extraction of grid stripe components.

More specifically, in X-ray radiography, it is a common practice to provide an irradiation field stop to the exit of an X-ray generation bulb of an X-ray generator 101 so as to avoid a portion other than a target portion of the object 102 (human body in this case) from being exposed. With this field stop, only the required portion of the object 102 can be irradiated with X-rays.

When the irradiation field stop function is used, not all image signals obtained from the X-ray sensor 104 are effective but only a partial image corresponding to an X-ray irradiation field defined by the irradiation field stop is effective in an image obtained by X-ray radiography.

Hence, in this embodiment, a computer means (CPU or the like; not shown) detects an effective partial image region (irradiated region) corresponding to the X-ray irradiation field from the objective image data in the memory 113 on the basis of the X-ray intensity distribution and stop shape, or other information, and stores only the data of that irradiated region (irradiated region data) in the memory 123.

As described above, since this embodiment processes only the irradiated region data in the memory 123, i.e., not all objective image data but only data of the required portion with the reduced information size, the processing time can be shortened. Also, since the correction process of the correction processor 115 is executed for only this effective partial image region, the time required for correction can be shortened.

In this embodiment, the irradiated region is extracted from the objective image after defective pixel correction. For example, the irradiated region may be extracted from the objective image after defective pixel correction.

15th Embodiment

In the X-ray image capture apparatus 2100 in FIG. 25 of the 11th embodiment, the grid stripe component extraction process of the grid stripe component extraction unit 117 is executed according to the flow chart shown in FIGS. 14A and 14B, as in the first embodiment.

In this embodiment, the grid stripe component extraction process of the grid stripe component extraction unit 117 can be executed according to the flow chart shown in, e.g., FIGS. 18A and 18B, as in the fifth embodiment.

16th Embodiment

When an image sensor such as a flat X-ray sensor or the like is used in the X-ray image capture apparatus as in the above embodiments, since a plurality of pixels that form the image sensor suffer sensitivity variations, image data acquired by that image sensor is corrected based on the sensitivity variations. For example, a flat-panel X-ray sensor is manufactured by the semiconductor manufacturing technique, and is made up of a plurality of pixels arranged in a two-dimensional matrix. The plurality of pixels suffer sensitivity variations due to the influence of the manufacturing precision in the semiconductor manufacturing process or the like and, hence, the aforementioned image correction is required. Such image correction is normally done by generating a reference image (also referred to as a correction image) based on an image obtained by photographing without any object, and dividing the image obtained by photographing an object by the reference image for respective pixels.

When the aforementioned image correction is made using the reference image which is generated based on radiation image information obtained via the grid without any object, the following problems are posed.

First, since the position of a grid image in an image acquired by the image sensor changes due to a change in positional relationship between an X-ray source and the image sensor, a stable reference image cannot be obtained.

Second, the contrast of a grid image in a radiation image obtained by photographing via an object and the grid changes due to the influence of the object, and that grid image is different from a grid image in the reference image, a stable reference image cannot be obtained, either.

Figure 30:
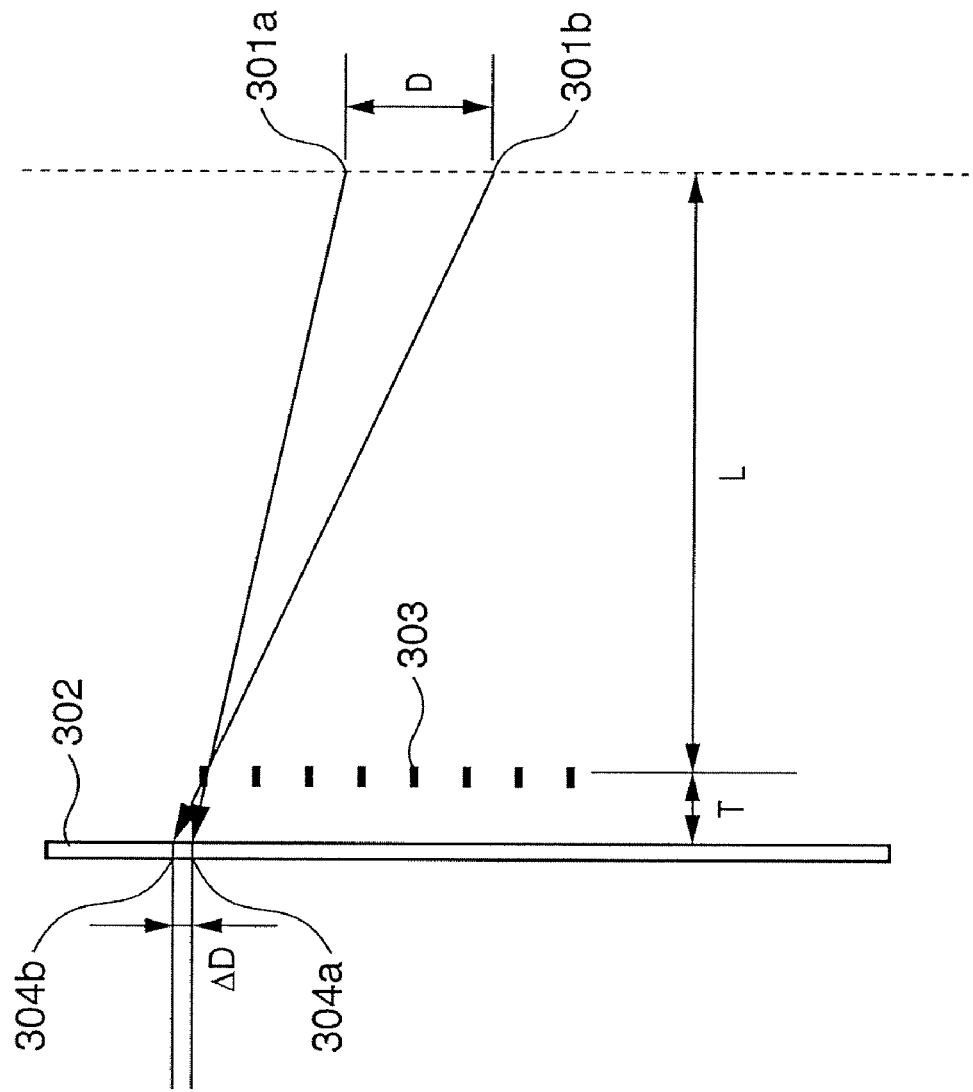
FIG. 30 is a view for explaining a change in phase of a grid image caused by a change in position of an X-ray source.

A change in position of a grid image will be explained below using FIG. 30. Assume that an X-ray source is present at a position 301a in FIG. 30, a grid made up of a plurality of lead foils is present at a position 303, and an image sensor is located at a position 302. As shown in FIG. 30, the shadow of a given grid foil is formed at a position 304a. Assume that the X-ray source has moved to a position 301b separated from the position 301a by distance D in FIG. 30. At this time, the shadow position of the former grid foil has moved to a position 304b. As a practical problem, a distance (gap) T between the grid and image sensor does not become zero, and is around 5 mm to meet a requirement upon mechanical attachment. Let L be the distance between the X-ray source and grid. Then, a moving distance $\Delta D$ of the shadow of the grid foil upon movement of the X-ray source from the position 301a to the position 301b is given by $\Delta D = DT/L$.

For example, if the distance L=1800 mm, T=5 mm, and D=50 mm, $\Delta D \approx 0.14$ mm. As the distance between neighboring pixels of an image sensor used for human body image diagnosis is normally 0.1 to 0.2 mm, the shadow of the grid foil moves a distance for one pixel on the image sensor if the position of the X-ray source moves 5 cm. In an ordinary medical scene, the position of the X-ray source may move about 5 cm between photographing for obtaining a reference image and that for obtaining an object image. The grid has a stripe pattern in one direction (normally, vertical direction) (has a structure in which lead foils are arranged in a stripe pattern when viewed from an X-ray incoming direction), but it may be inclined entirely (the direction of stripes of the grid is not stable with respect to the arrangement direction of pixels of the image sensor) due to the influence of attachment precision.

A change in contrast of a grid image due to an object is a phenomenon that the contrast of the grid image lowers under the influences of X-ray absorption, a change in X-ray quality, generation of scattered rays, or the like by the object. With this phenomenon, a grid image with a contrast different from that of the grid image in the reference image is superposed on the object image.

In such case, even when the division process between the object image on which the grid image is superposed and the reference image that includes the grid image is made, the grid image may be emphasized in place of being erased or reduced, or a complicated two-dimensional pattern may be added as a combination of the grid images in the object image and reference image.

A technique for removing a periodic grid image present on an object image by an arbitrary scheme such as spatial filtering or the like is known. However, when the reference image includes the grid image, and a complicated pattern is formed (superposed) on the corrected image in an attempt to remove the grid image upon dividing the object image by the reference image, as described above, it becomes very difficult to remove that pattern from the corrected image by spatial filtering or the like.

In case of photographing without the intervention of an object, since no scattered rays are present, the reference image can be obtained by photographing without any grid (a reference image should be obtained by photographing without any grid). However, in practice, it is troublesome and not preferable to photograph by detaching the grid every time a reference image is obtained.

In the 16th and 17th embodiments, a radiation image processing apparatus, an image processing system, and a radiation image processing method, which generate correction data, suitably used to correct radiation image data of an object on the basis of sensitivity variations of a plurality of pixels which form an image sensor (solid-state image sensing element) on the basis of image data obtained by radiography via a scattered ray removal grid without any object, and make the correction using that correction image data, a program for making a computer implement or execute the functions of the apparatus or system or the processing steps of the method, and a storage medium that records the program, will be described.

Figure 31:
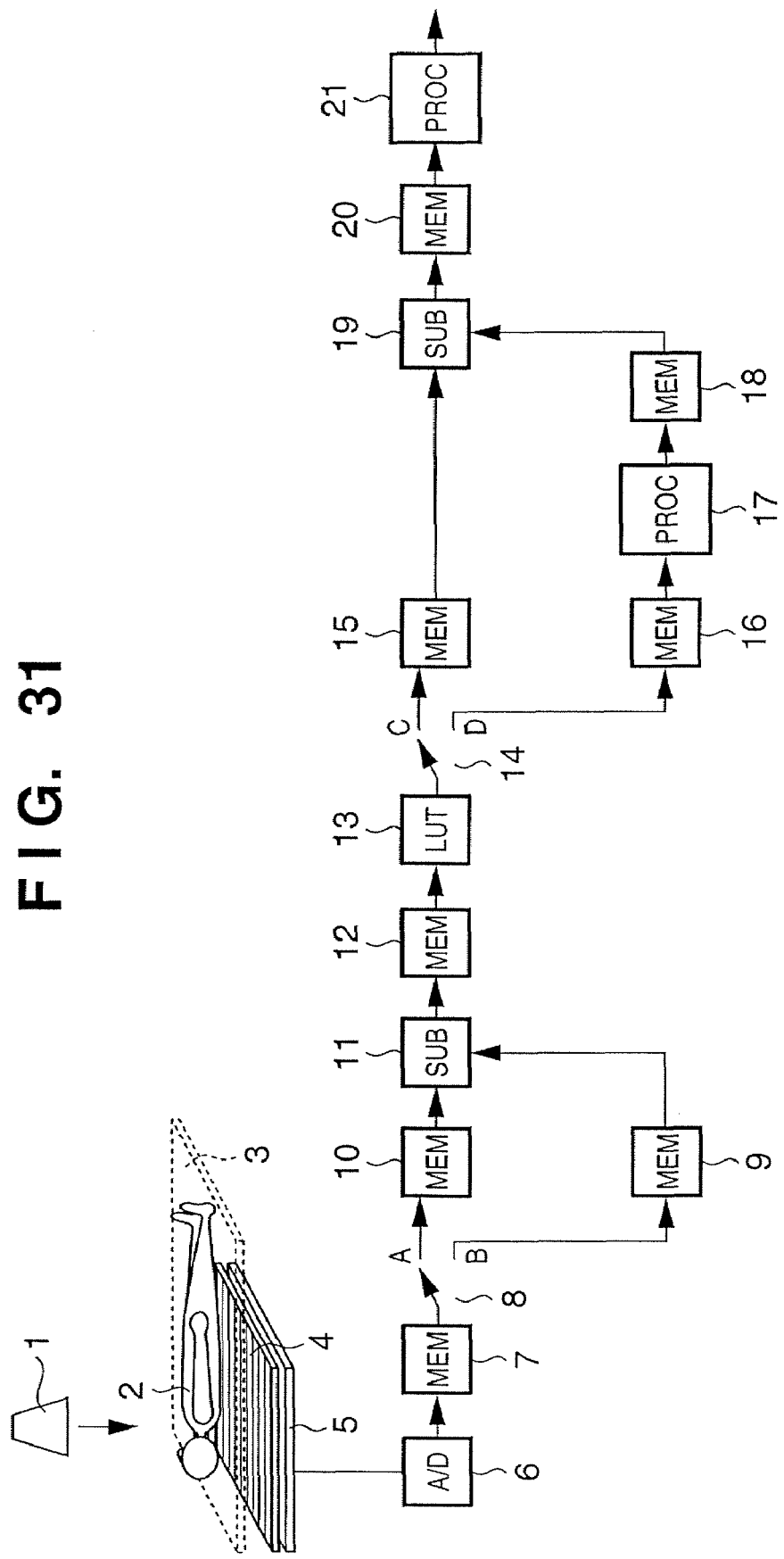
FIG. 31 is a block diagram of the 16th embodiment.

FIG. 31 is a block diagram showing an X-ray image photographing apparatus (radio image processing apparatus) according to the 16th embodiment.

Referring to FIG. 31, reference numeral 1 denotes an X-ray generator which is controlled by a controller (not shown), and receives high voltages to generate X-rays in a direction indicated by the arrow. Reference numeral 2 denotes an object represented by a human body; and 3, a bed that supports the object 2.

Reference numeral 4 denotes a scattered ray removal grid which is arranged mainly for the purpose of removing scattered rays emanating from the object, and selectively transmitting direct rays. Reference numeral 5 denotes an X-ray image sensor (flat-panel sensor) used to convert the intensity distribution of X-rays that have been transmitted through the object into an electrical signal. The X-ray image sensor 5 comprises a large-scale solid-state image sensing element made up of a plurality of pixels arranged in a two-dimensional matrix. This X-ray image sensor will be referred to as a flat-panel sensor hereinafter.

An X-ray image is spatially sampled on a two-dimensional plane by the flat-panel sensor 5. Normally, upon photographing a human body internal structure (human body portion), this sampling pitch is set at about 100 to 200 µm. The flat-panel sensor 5 is controlled by a controller (not shown) to sequentially scan and convert charges generated for respective pixels in correspondence with the incoming X-ray dose into electrical quantities (voltages or currents), and outputs X-ray image data as an electrical signal.

Reference numeral 6 denotes an A/D converter for converting analog quantities output from the flat-panel sensor 5 into digital values. Reference numeral 7 denotes a memory (storage unit) for temporarily storing the A/D-converted digital values as image information. Reference numeral 8 denotes a switch unit for reading out the contents of the memory 7, and selectively storing the readout image information in one of two memories (storage units) 9 and 10. The memory 9 stores an image signal output from the flat-panel sensor 5 upon photographing without X-ray exposure as an offset fixed pattern image, and the memory 10 stores an image of the object 2 obtained by radiating X-rays.

Practical photographing is done in such a manner that an X-ray dose measuring device (normally called a phototimer; not shown) for monitoring the X-ray dose that has been transmitted through the object is used in X-ray exposure control, and X-ray exposure is terminated at the instance when the integral value of the radiated X-ray dose has reached a predetermined value. The controller of this embodiment scans the flat-panel sensor 5 immediately after X-ray exposure has been terminated, stores object image information in the memory 7, sets the switch unit 8 at the A side, and stores image information of the memory 7 in the memory 10.

Immediately after that process, the controller drives the flat-panel sensor 5 without X-ray exposure to accumulate charges for the same period of time as the photographing time (X-ray exposure time) determined using the aforementioned phototimer. The controller then stores image data output by scanning the flat-panel sensor 5 in the memory 7 as offset fixed pattern data. The offset fixed pattern data is stored in the memory 9 by setting the switch unit 8 at the B side.

Reference numeral 11 denotes a differential arithmetic device for making a differential arithmetic operation between two images stored in the memories 9 and 10. The device 11 sequentially subtracts pixel values in the memory 9 from those in the memory 10 at corresponding positions in practice. Reference numeral 12 denotes a memory (storage unit) for storing the arithmetic result of the differential arithmetic device 11.

Reference numeral 13 denotes a lookup table (LUT) used to convert image data stored in the memory 12 into its logarithmic values. Reference numeral 14 denotes a switch unit for selectively storing data output from the LUT 13 in one of two memories (storage units) 15 and 16. Image data of the object stored in the memory 12 is logarithmically converted by the LUT 13, and is then stored in the memory 15 by setting the switch unit 14 at the C side.

The memory 16 stores an image obtained when the X-ray image photographing apparatus makes an operation called calibration photographing. In calibration photographing, image data is captured by the same operation as described above, and is stored in the memory 16 by setting the switch unit 14 at the D side. In this case, photographing is done via the grid 4 without any object 2 unlike in normal object photographing.

Normally, this calibration photographing is made once per day, e.g., at the beginning of daily job, and this operation acquires reference image data (also referred to as correction image data) used to correct an image based on sensitivity variations (also referred to as gain variations) of a plurality of pixels which form the flat-panel sensor 5.

Reference numeral 17 denotes a grid image removal unit for selectively removing only stripe image components caused by the grid 4 from the image data which is obtained by photographing via the grid 4 without any object 2 and is stored in the memory 16. Reference numeral 18 denotes a memory (storage unit) for storing the processing result of the grid image removal unit 17, i.e., reference image data (correction image data) corresponding to sensitivity variation (gain variation) data of the plurality of pixels which form the flat-panel sensor 5.

Reference numeral 19 denotes a subtractor for subtracting the reference image data stored in the memory 18 from the object image data stored in the memory 15 (this process corresponds to division between images in practice since each image data is obtained via the logarithmic conversion LUT 13). Reference numeral 20 denotes a memory (storage unit) for storing image data after image correction has been done based on the sensitivity variations (gain variations) of the plurality of pixels which form the flat-panel sensor 5.

Figure 32:
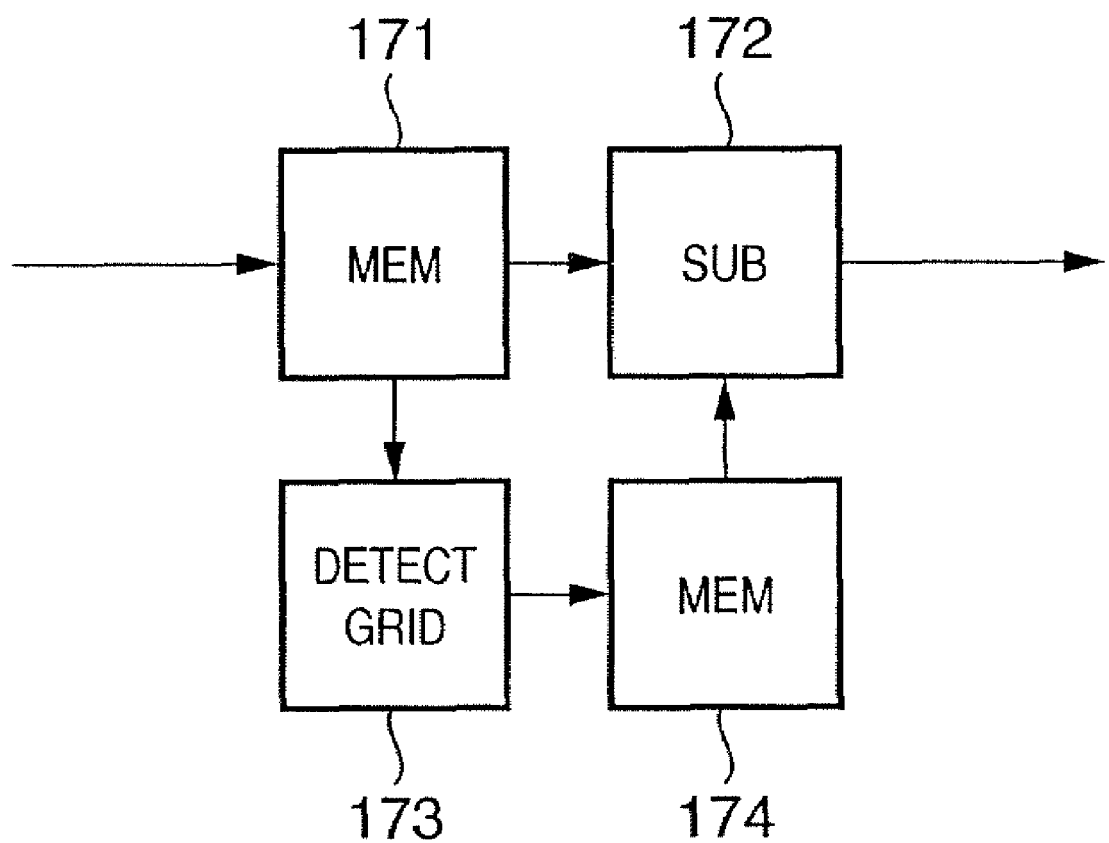
FIG. 32 is a block diagram showing the arrangement of a grid image removal unit in the 16th embodiment.

FIG. 32 shows the arrangement of the grid image removal unit 17. Reference numeral 171 denotes a memory (storage unit) for temporarily storing image data stored in the memory 16; 173, a grid component extraction unit for extracting only stripe image components caused by the grid 4 on the basis of the feature of the stripe image components caused by the grid 4; 174, a memory (storage unit) for storing stripe image component data which is extracted by the grid component extraction unit 173 and caused by the grid; and 172, a subtractor for obtaining the aforementioned reference image data (correction image data) by subtracting image data stored in the memory 174 from that stored in the memory 171.

As will be explained in detail later, the grid component extraction unit 173 basically executes a process exploiting a nature that grid stripes (image components caused by the grid) originally have a constant spatial frequency and are steady across the entire image. That is, the unit 173 extracts grid stripe components from an objective image by spatial filtering, finds an unsteady portion from the grid stripe components, and converts that unsteady portion into steady data, thereby generating original grid stripe components.

Since no image components caused by the grid upon calibration photographing are superposed on the reference image data stored in the memory 18 in FIG. 31, only image components caused by the grid upon object photographing are superposed on the object image data stored in the memory 20. Therefore, reference numeral 21 in FIG. 31 denotes a grid image removal unit which is the same as the grid image removal unit 17, and can remove grid stripe components (image components caused by the grid) superposed upon object photographing by the same operation as in the grid image removal unit 17.

Image data processed by the grid image removal unit 21 may undergo another process, e.g., an image process to obtain data suitable for image diagnosis such as a tone process, dynamic range change process, spatial frequency process, or the like. After that, the image data is transferred to an external device represented by a display device, print device, filing device, or the like.

In this embodiment and another embodiment to be described below, grid stripe components cannot often be removed perfectly, e.g., some grid stripe components may remain. However, even in such case, if the grid stripe components are sufficiently reduced, the effect of each embodiment can be obtained, and the object of the embodiment can be achieved.

17th Embodiment

Figure 33:
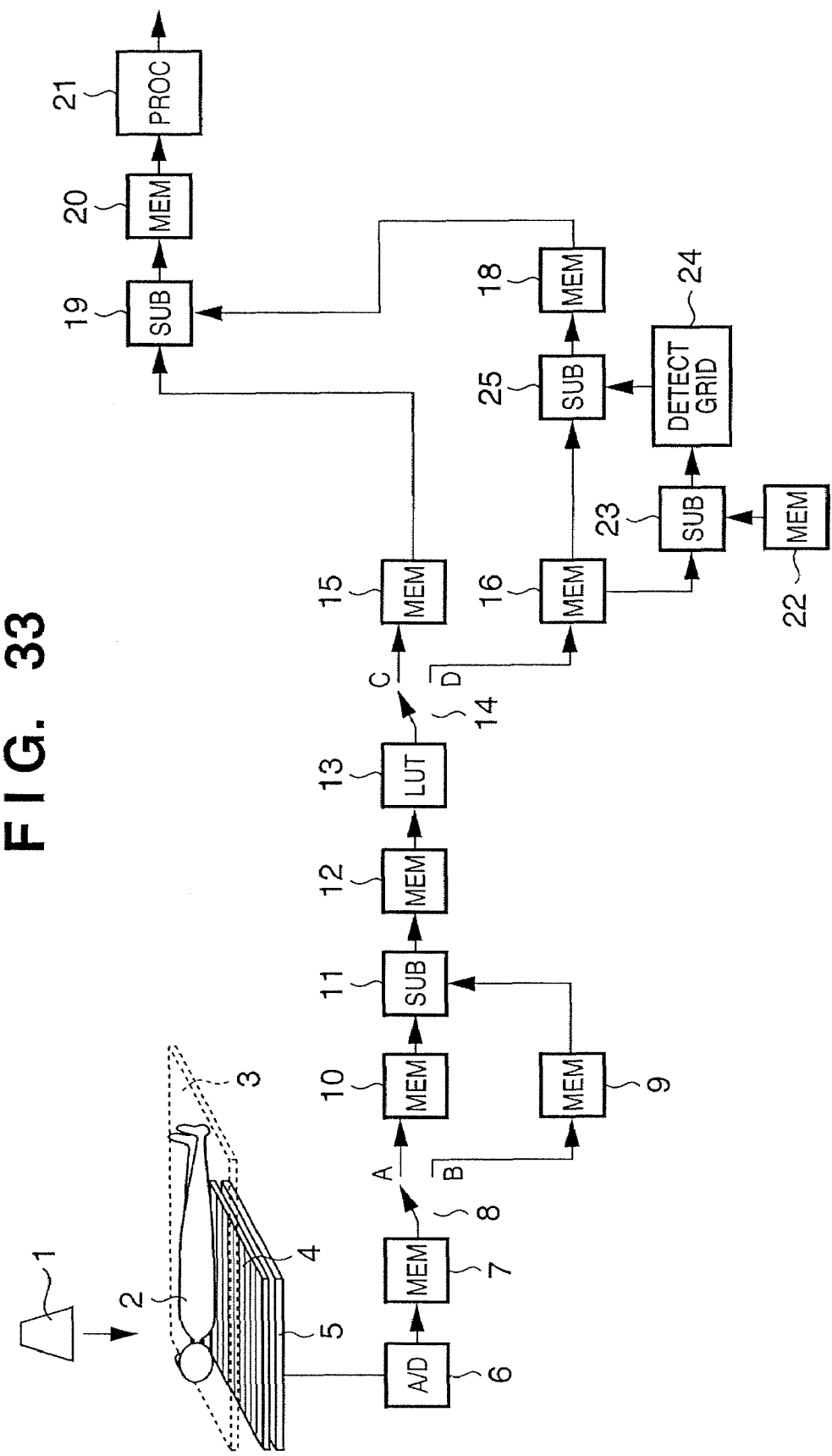
FIG. 33 is a block diagram of the 17th embodiment.

FIG. 33 is a block diagram showing an X-ray image photographing apparatus (radiation image processing apparatus) according to the 17th embodiment. The same reference numerals in FIG. 33 denote the same parts as in the X-ray image photographing apparatus shown in FIG. 31, and a description thereof will be omitted.

A characteristic feature of the 17th embodiment lies in that a memory (storage unit) 22 and differential arithmetic device 23 are used. The memory 22 holds sensitivity variation data (gain variation data) of the flat-panel sensor 5 obtained by photographing X-rays radiated without the intervention of the object 2 and grid 4 in the manufacture or upon installation of this X-ray image photographing apparatus.

Note that this sensitivity variation data has undergone logarithmic conversion, and can be acquired using the same building components 1, 3, and 5 to 16 as those in the X-ray image photographing apparatus shown in FIG. 31. The acquired data can be stored in the memory 22. The differential arithmetic device 23 subtracts the sensitivity variation data stored in the memory 22 from the image data which is obtained by photographing via the grid 4 without any object, and is stored in the memory 16 (this subtraction process corresponds to division between images in practice, since these image data have undergone logarithmic conversion).

With this subtraction process, only grid stripe components are extracted, and are stored in the memory 18. Since the image data stored in the memory 16 is image data obtained by detecting the intensity distribution of X-rays modulated by the grid 4 by the flat-panel sensor 5, i.e., image data on which the sensitivity variation data of the flat-panel sensor 5 and grid stripe component data are superposed, only grid stripe components are extracted by subtracting the sensitivity variation data stored in the memory 22 from the image data stored in the memory 16 (this process corresponds to division in practice).

Note that the sensitivity variation data stored in the memory 22 must be substantially equal to components of the sensitivity variation data of the flat-panel sensor 5 in the image data stored in the memory 16. Therefore, image data to be stored in the memories 22 and 16 must be acquired under substantially equal photographing conditions.

However, in practice, since a photographing environment, X-ray irradiation distribution, or the like upon capturing image data to be stored in the memory 22 in the manufacture or installation of this X-ray image photographing apparatus is different from that upon calibration photographing, it often becomes difficult to extract only grid stripe components by the aforementioned process.

In such case, by adding a grid component extraction unit 24 which is the same as the grid component extraction unit 173 and extracts only grid stripe components from image data obtained by the differential arithmetic device 23, grid stripe components can be accurately extracted. Reference numeral 25 denotes a differential arithmetic device for subtracting image data obtained by the differential arithmetic device 23 or grid component extraction unit 24 from the image data stored in the memory 16. The differential arithmetic device 25 can obtain image data consisting of only sensitivity variation data (gain variation data) of the plurality of pixels of the flat-panel sensor 5, and that image data is stored in the memory 18 as reference image data (correction image data).

The gist of the 17th embodiment is to improve the extraction precision of grid stripe components. The image data stored in the memory 16 corresponds to the sum of the grid stripe components and sensitivity variation components of the plurality of pixels of the flat-panel sensor 5. The sensitivity variations of the plurality of pixels of the flat-panel sensor 5 are not steady, and their spatial changes are very steep or random. For this reason, it is not easy to separate the sensitivity variation components and grid stripe components. Therefore, like in this embodiment, the extraction precision of grid stripe components can be improved by removing or reducing unsteady image components caused by the sensitivity variations using image data resulting from only the sensitivity variations (gain variations) of the flat-panel sensor 5 which was acquired and stored at an appropriate timing, e.g., in the manufacture or upon installation of the X-ray image photographing apparatus.

In the 17th embodiment, the grid component extraction unit 24 may be omitted if grid stripe components can be accurately extracted by only the process of the differential arithmetic device 23.

An example of the detailed arrangement of the grid image removal unit 21 in the 16th and 17th embodiments can use that in the first to fifth embodiments described earlier.

Note that the grid image removal unit 17 in the 16th embodiment (also the grid component extraction unit 173 in the 16th embodiment and the grid component extraction unit 24 in the 17th embodiment) performs the same operation as that of the grid image removal unit 21 in the 16th and 17th embodiments, as described above, and processes an X-ray image (calibration photographing image) obtained via the grid without any object in place of an X-ray image which is obtained via the object and grid. Therefore, since the grid image removal unit 17 can have the same arrangement as the grid image removal unit 21, it can be arranged in the same manner as in the arrangement example in the first to fifth embodiments.

According to the radiation image processing apparatuses of the 16th and 17th embodiments described above, since only image components resulting from the grid are removed from image data obtained by radiography via the grid without any object, correction image data suitable to correct object image data based on sensitivity variations (gain variations) of a plurality of pixels which form an image sensor (solid-state image sensing element) can be obtained.

Since only image components resulting from the grid can be removed from calibration image data obtained by radiography via the grid without any object, calibration photographing can be made without detaching the grid, resulting in high convenience.

Also, image components resulting from the grid can be more accurately extracted (removed) from calibration image data using correction image data which is acquired in advance and is used to correct an image based on sensitivity (gain) variations of the plurality of pixels of the image sensor.

Sensitivity or gain variations (sensitivity or gain image) of the plurality of pixels which form the image sensor have less association among pixels; they have steep variation components. Therefore, the spatial frequency components of the sensitivity variations are distributed over a broad spatial frequency region unlike image components of a normal image. For this reason, image components resulting from the grid and those of the sensitivity variations are superposed in both the frequency and space domains, and their separation may often become difficult in practice. Even in such case, if sensitivity variation image data which does not contain image components resulting from the grid (e.g., image data obtained by radiography without the intervention of the object and grid) is acquired and recorded in, e.g., a factory, steep variation components caused by sensitivity variations in calibration image data can be removed or reduced by making sensitivity (gain) correction of the calibration image data using the sensitivity variation image data acquired in advance upon acquiring the calibration image data that contains image components caused by the grid. Hence, the extraction precision of only image components resulting from the grid can be improved.

Furthermore, correction image data from which image components resulting from the grid are removed is generated, and image data obtained by photographing via the object and grid is corrected using that correction image data, thereby removing the image components resulting from the grid from the corrected image data. Hence, a radiation image processing apparatus which can appropriately remove image components resulting from the grid from radiation image data obtained by radiography via the grid which is not moved but is fixed in position during photographing can be provided.

18th Embodiment

The aforementioned conventional grid stripe removing methods (Patent Nos. 2507659 and 2754068, Japanese Patent Laid-Open No. 8-088765, and U.S. Pat. No. 5,050,198) are achieved under the condition that grid stripe information are steadily present over the entire image.

However, when an article (metal or the like) that perfectly or nearly perfectly intercepts radiation is present in an object, or when radiation is too intense, and a partial region where the output from an image-receiving sensor is saturated (e.g., a region outside the object, where radiation directly hits (so-called through region) is formed, a partial region of the obtained image may not often contain any grid stripe information. In such information, the entire image cannot be processed using a single algorithm.

For example, as disclosed in U.S. Pat. No. 5,050,198, when division is made for the entire image using grid image information which is acquired in advance, since that division process is applied to a portion where no grid stripes are present, grid stripes are unwantedly generated in that portion.

To solve this problem, in the 18th and 19th embodiments, a radiation image processing apparatus, image processing system, radiation image processing method, storage medium, and program, which can obtain a high-quality radiation image, from which grid stripe components are removed, from a radiation image obtained by radiography using a grid will be explained.

Figure 34:
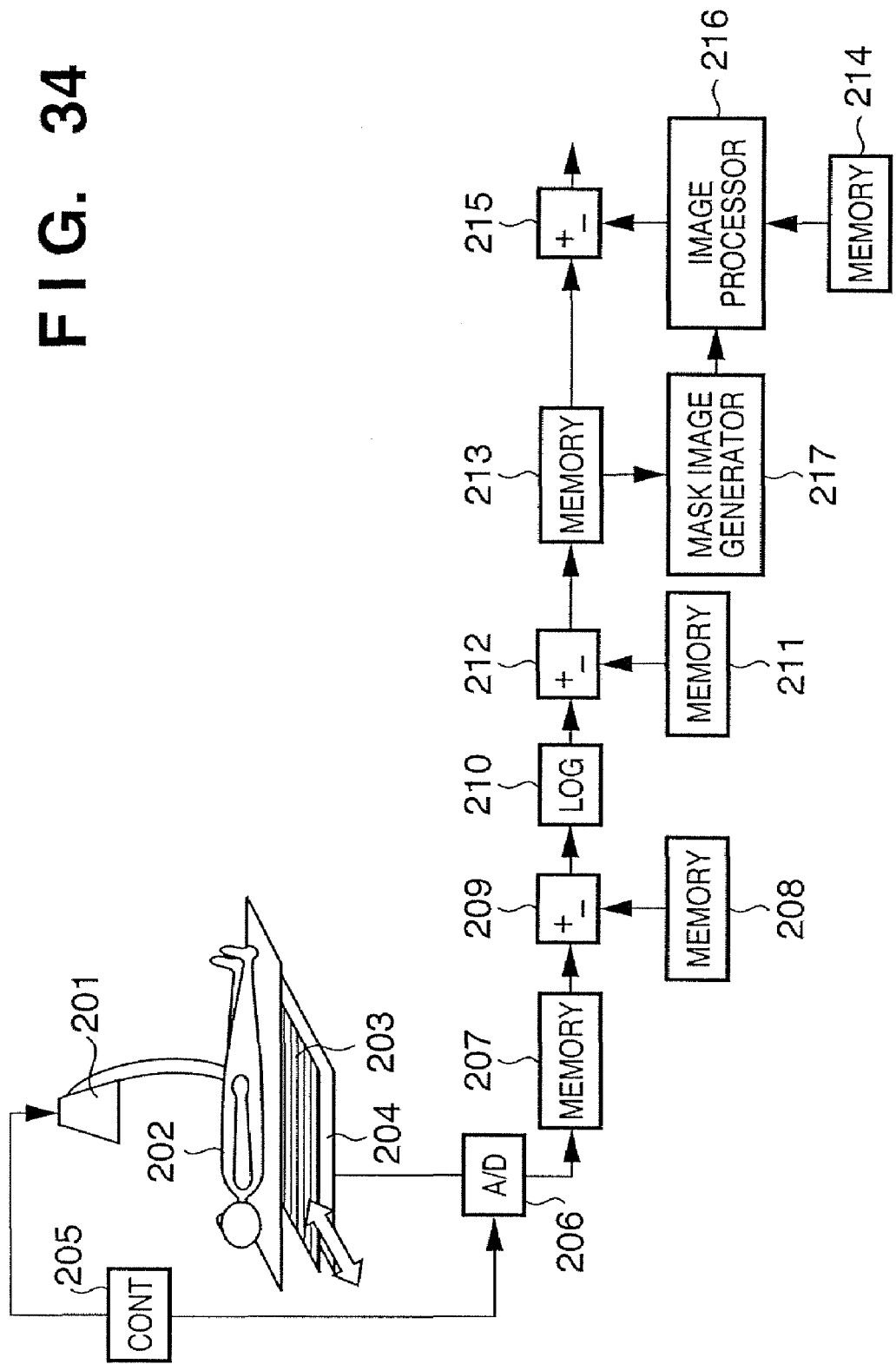
FIG. 34 is a block diagram functionally showing the arrangement of an X-ray image processing apparatus according to the 18th embodiment.

FIG. 34 is a block diagram of an X-ray image capture apparatus according to the 18th embodiment of the present invention.

Referring to FIG. 34, reference numeral 201 denotes an X-ray generator for generating X-rays. Reference numeral 202 denotes an object which imitates a human body in consideration of medical use in this embodiment. Reference numeral 203 denotes a grid which is used to remove scattered X-rays coming from the object 202, and has a detachable structure. Reference numeral 204 denotes a flat X-ray sensor for detecting the distribution of the X-ray dose that has been transmitted through the object 202. In this sensor, a plurality of detectors for detecting X-ray intensities are arranged in a matrix on the detection surface.

Examples of this flat X-ray sensor 204 include a sensor which temporarily converts the X-ray intensity into fluorescence, and detects the fluorescence by a plurality of light intensity detectors arranged in a matrix, a sensor which forms a charge distribution by attracting free electrons liberated when a specific object is irradiated with X-rays, and converts the charge distribution into electrical signals by a plurality of charge detectors (capacitors) arranged in a matrix, and the like. Reference numeral 205 denotes a controller for the X-ray generator. The controller 205 controls the X-ray generator to start X-ray radiation in response to a generation trigger which is input by an operator at a console (not shown).

Reference numeral 206 denotes an analog/digital (A/D) converter for converting an electrical signal output from the X-ray sensor 204 into a digital value. The A/D converter 206 converts electrical signals read from the X-ray sensor into digital values in turn in synchronism with X-ray radiation or driving of the X-ray sensor 204. The number of A/D converters 206 is not limited to one. For example, a plurality of A/D converters 206 may operate parallelly to increase the conversion speed.

Reference numeral 207 denotes a memory for temporarily storing the digital values A/D-converted by the A/D converter 206. This memory 207 stores image data as a set of a plurality of digital values. Reference numeral 208 also denotes a memory. The memory 208 records, as image data, digital values captured by the X-ray sensor 204 without X-ray radiation using this apparatus, so as to remove offset-like fixed pattern noise unique to the X-ray sensor 204 from a radiation image.

Reference numeral 209 denotes an arithmetic unit for sequentially subtracting fixed pattern noise image data from image data which is captured via the object 202 and is recorded in the memory 207 for respective positions. Reference numeral 210 denotes a lookup table (LUT) for converting the output from the arithmetic unit 209 into a value proportional to a logarithm.

Reference numeral 211 denotes a memory. The memory 211 stores a gain pattern which is obtained by removing fixed pattern noise stored in the memory 208 from image information captured by the X-ray sensor 204 upon radiating X-rays while the object 202 and grid 203 are detached in this apparatus, and which is converted into values proportional to logarithmic values by the LUT 210, so as to correct gain variations unique to the X-ray sensor 204 for respective detectors (pixels).

Reference numeral 212 denotes an arithmetic unit which subtracts the gain pattern stored in the memory 211 from the image information logarithmically converted by the LUT 210, and executes division in practice. This quotient is temporarily stored in a memory 213. Reference numeral 214 denotes a memory that stores image data obtained by X-ray radiography while attaching the grid 203 alone without placing any object 202. This image information consists of only grid stripe information, that has undergone corrections of the fixed pattern noise and gain pattern in the arithmetic units 209 and 212 in advance.

Reference numeral 215 denotes an arithmetic unit which outputs image information from which grid stripe information is removed by subtracting the grid stripe information from the image information stored in the memory 213. Reference numeral 217 denotes a mask image generator for generating a mask image in correspondence with the signal levels of the image information stored in the memory 213. Reference numeral 216 denotes an image processor which masks the grid stripe information stored in the memory 214 using the mask image generated by the mask image generator 217.

The arithmetic unit 215 subtracts the grid stripe information output from the image processor 216 from the image information stored in the memory 213. Since this grid stripe information has undergone the mask process, the subtraction process of the arithmetic unit 215 is done for image information except for a portion where no grid stripes are present. Hence, no new grid stripes never appear in a portion where no grid stripes are present by the removal process of the grid stripe information from that portion.

Figure 35:
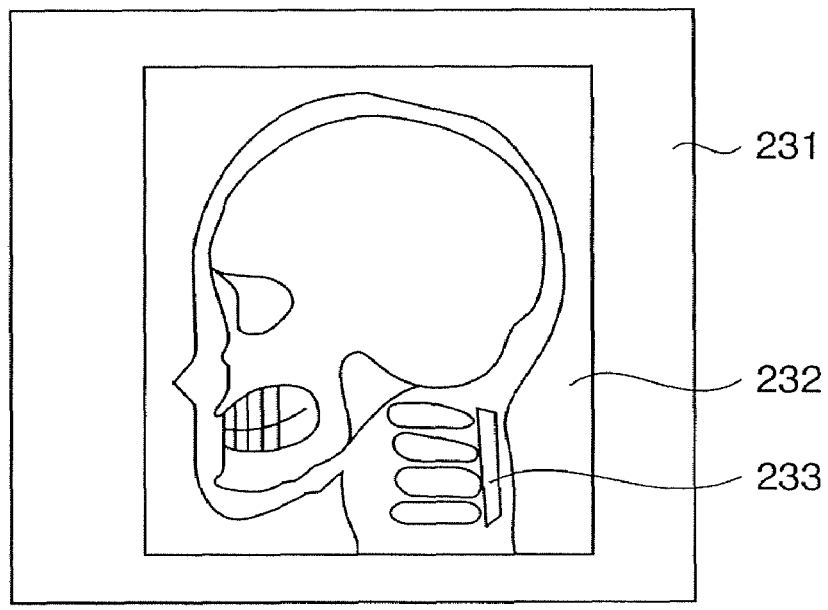
FIG. 35 illustrates an example of a medical radiation image.

FIG. 35 illustrates an example of a medical image. Note that this image is photographed using the grid. A region 231 is not exposed since X-rays are collimated, a region 232 is a so-called "through" region where X-rays have reached without going through the object 202, and a region 233 corresponds to a metal object surgically implanted in this human body.

At this time, since no X-rays reach the X-ray sensor 4 in the regions 231 and 233, the signal level corresponding to these regions is very low. On the other hand, the output from the X-ray sensor 204 is nearly saturated in the region 232. Therefore, image information of each of the regions 231 to 233 does not contain any grid image information. As has been described above, if grid stripe information is simply removed from the image information as well as the regions 231 to 233, grid stripe information undesirably appears in these regions containing no grid stripe information.

Figure 36:
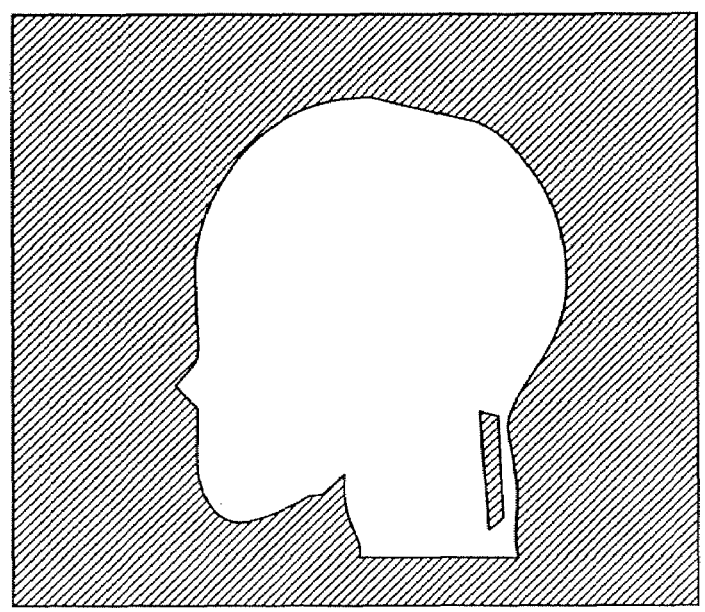
FIG. 36 illustrates an example of a mask image generated from the medical radiation image shown in FIG. 35.

FIG. 36 shows an example of a mask image generated by the mask image generator 217 on the basis of the image information shown in FIG. 35. In this mask image, a region where the signal level of the image information in FIG. 35 has a value equal to or larger than a predetermined value, and a region where the signal level has a value equal to or lower than another predetermined value are set to be black (0). Mask image generation of the mask image generator 217 preferably uses a method of separating regions by simple signal level comparison, and then removing small regions by a combination of erosion and dilation as normal binary image processes.

The image processor 216 masks the grid stripe information stored in the memory 214 using the mask image generated in this way. Therefore, the arithmetic unit 215 does not remove any grid stripe information from image information portions corresponding to black (0) regions in FIG. 36, and no new grid stripe information is never generated in these regions.

The image processed in this way undergoes an image process for medical diagnosis (not shown), and is then output to an external device. This embodiment has been explained using the block diagram that shows the flow of signal information. However, in practice, a method of executing the above processing using programming means on a computer (not shown) is also preferably used, and such method can be implemented easily.

19th Embodiment

Figure 37:
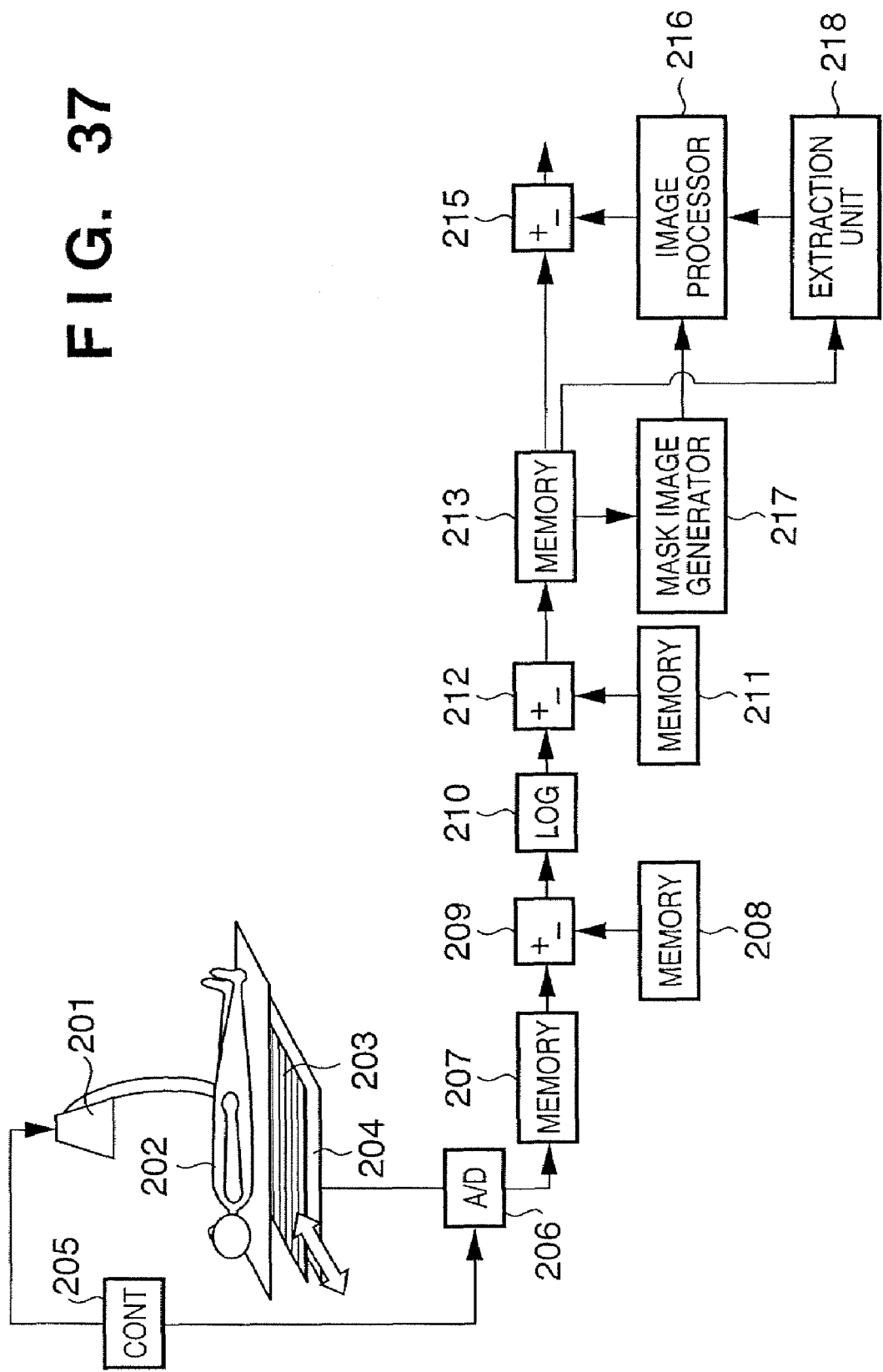
FIG. 37 is a block diagram functionally showing the arrangement of an X-ray image processing apparatus according to the 19th embodiment.

In this embodiment, grid stripe information is extracted from image information to be processed in every process in place of acquiring grid stripe information in advance unlike in the 18th embodiment. FIG. 37 is a block diagram showing the arrangement of this embodiment. A detailed description of the same building components as in FIG. 34 will be omitted. Reference numeral 218 denotes an extraction unit for extracting a grid stripe information image from image information stored in the memory 213 by filtering. This filtering can be implemented by normal spatial bandpass filtering.

Other arrangements are the same as those in the 18th embodiment. That is, as in the 18th embodiment, the mask image generator 217 generates a mask image in correspondence with the signal levels of image information, and the image processor 216 masks the grid stripe information using that mask image. The arithmetic unit 215 subtracts the grid stripe information which has undergone the mask process from the image information.

The image processed in this way undergoes an image process for medical diagnosis (not shown), and is then output to an external device. This embodiment has been explained using the block diagram that shows the flow of signal information. However, in practice, a method of executing the above processing using programming means on a computer (not shown) is also preferably used, and such method can be implemented easily.

Note that the first to 19th embodiments have explained hardware implementation. However, the above embodiments can also be implemented by controlling the entire apparatus using software.

The objects of the present invention are also achieved by supplying a storage medium, which stores a program code of software that can implement the functions of the host and terminal of the first to 19th embodiments to a system or apparatus, and reading out and executing the program code stored in the storage medium by a computer (or a CPU or MPU) of the system or apparatus.

In this case, the program code itself read out from the storage medium implements the functions of the first to 19th embodiments, and the program code and the storage medium which stores that program code constitute the present invention.

As the storage medium for supplying the program code, for example, a ROM, flexible disk, hard disk, optical disk, magneto-optical disk, CD-ROM, CD-R, magnetic tape, nonvolatile memory card, ROM, and the like may be used.

The functions of the first to 19th embodiments may be implemented not only by executing the readout program code by the computer but also by some or all of actual processing operations executed by an OS or the like running on the computer on the basis of an instruction of the program code.

Furthermore, the functions of the first to 19th embodiments may be implemented by some or all of actual processing operations executed by a CPU or the like arranged in a function extension board or a function extension unit, which is inserted in or connected to the computer, after the program code read out from the storage medium is written in a memory of the extension board or unit.

Figure 38:
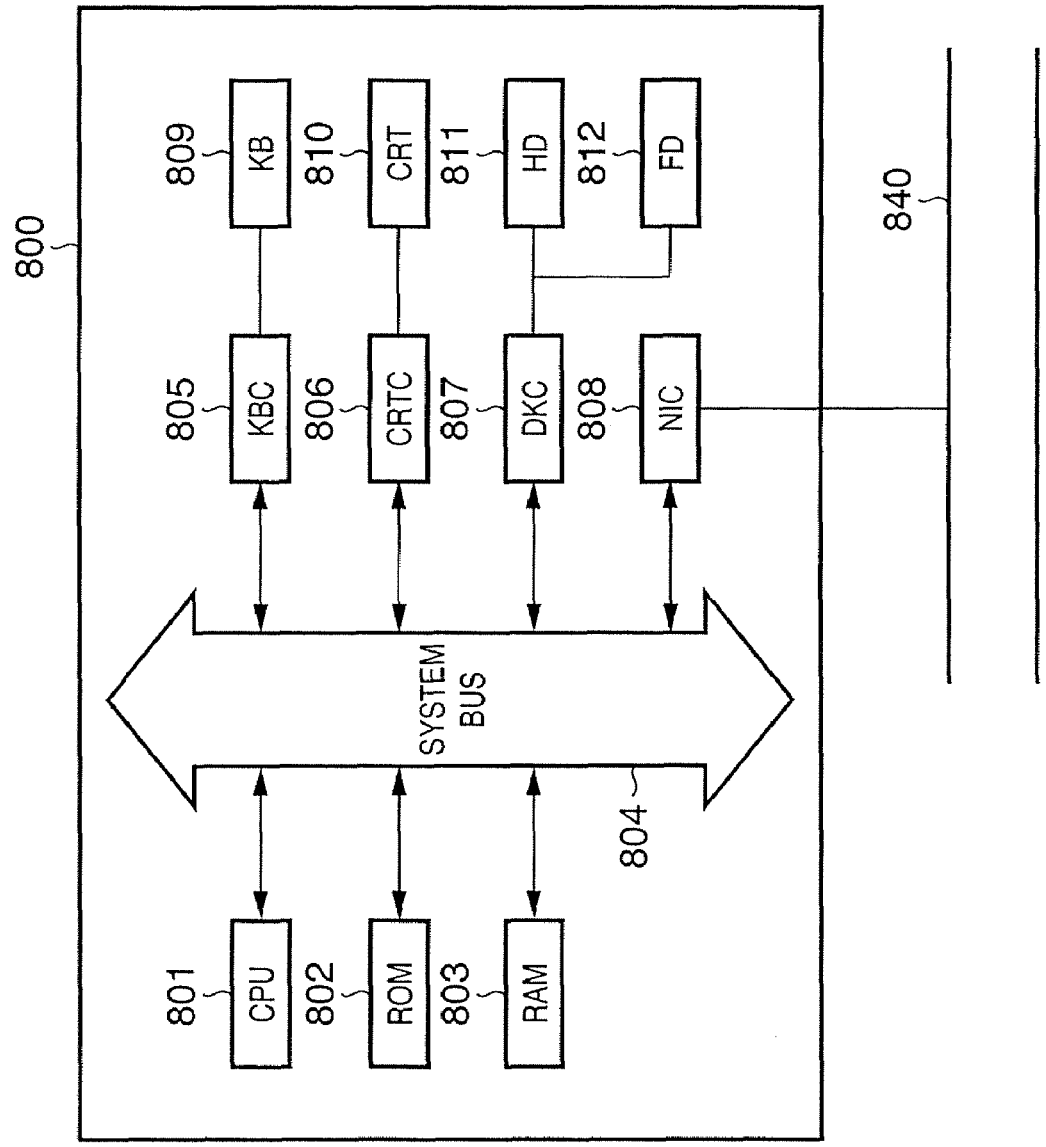
FIG. 38 is a block diagram showing an example of the arrangement that reads out, from a computer-readable storage medium that records a program for making a computer implement the functions of each embodiment, the program and executes the readout program.
Figure 39:
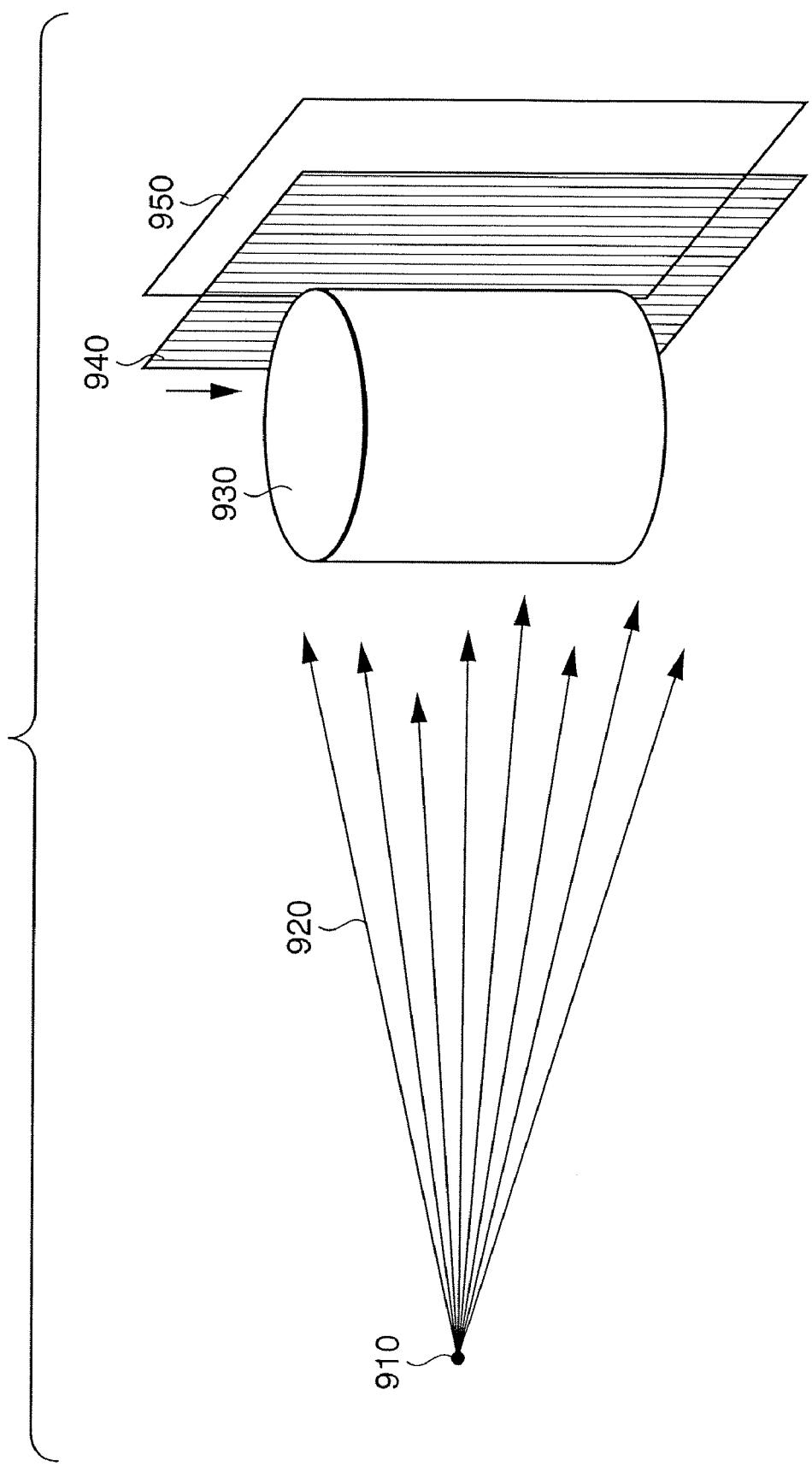
FIG. 39 is a view for explaining radiography using a grid.
Figure 40B:
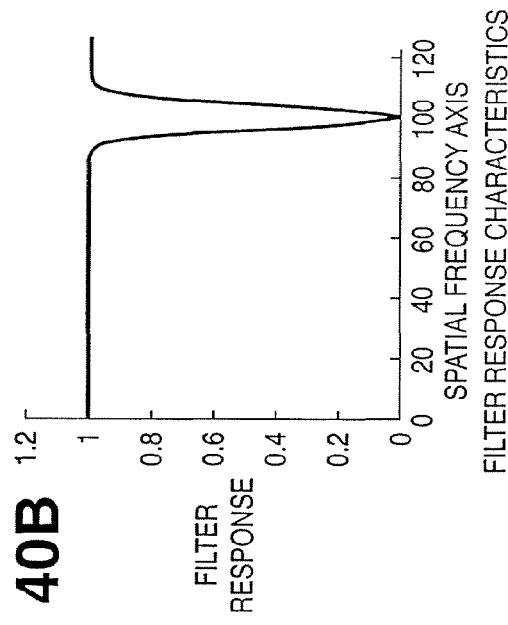
FIGS. 40A to 40D are graphs for explaining an example of the effect of filtering for an image obtained by radiography.
Figure 40D:
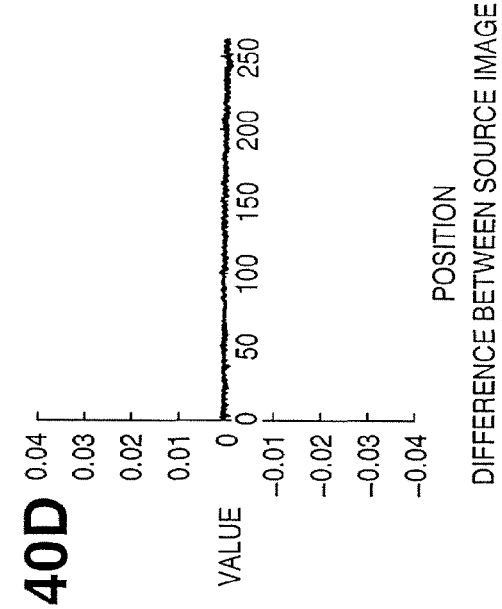
Figure 40A:
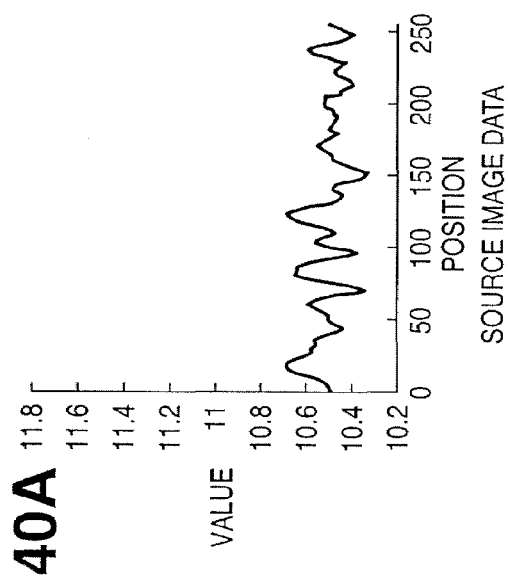
Figure 40C:
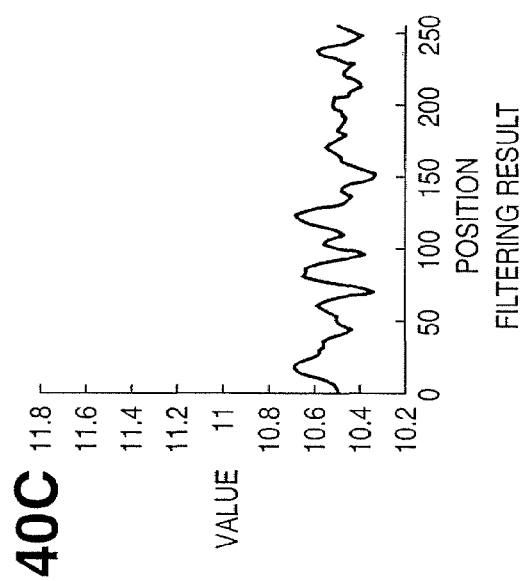
Figure 41A:
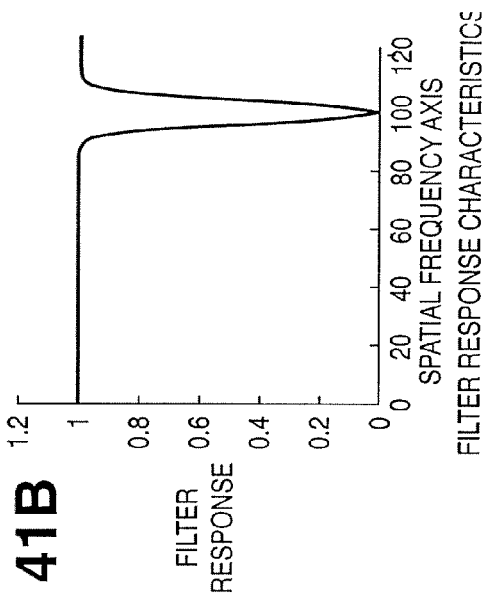
FIGS. 41A to 41D are graphs for explaining another example of the effect of filtering for an image obtained by radiography.
Figure 41B:
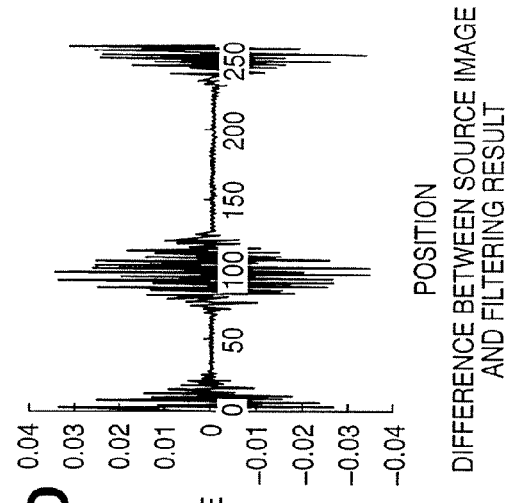
Figure 41C:
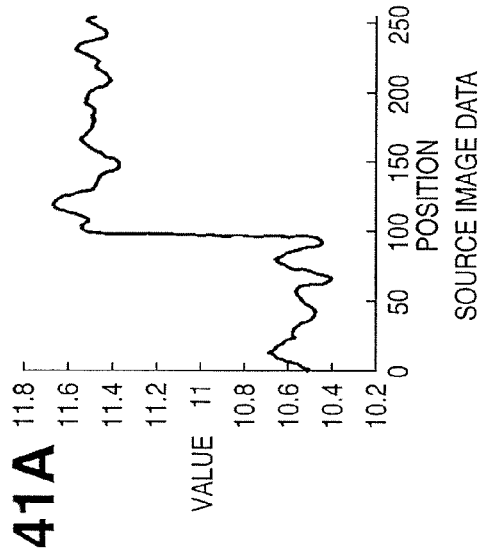
Figure 41D:
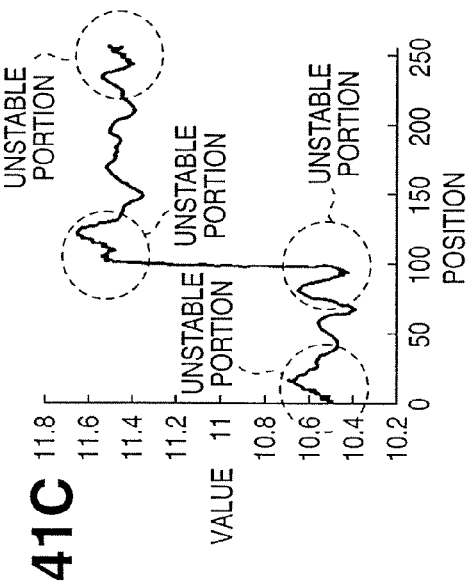

FIG. 38 shows an example of the arrangement of a computer function 800.

As shown in FIG. 38, the computer function 800 comprises a CPU 801, a ROM 802, a RAM 803, a keyboard controller (KBC) 805 for a keyboard (KB) 809, a CRT controller (CRTC) 806 for a CRT display (CRT) 810 serving as a display unit, a disk controller (DKC) 807 for a hard disk (HD) 811 and flexible disk (FD) 812, and a network interface controller (NIC) 808 used to establish connection to a network 840, which are connected via a system bus 804 to allow intercommunications.

The CPU 801 systematically controls the respective building components connected to the system bus 804 by executing software stored in the ROM 802 or HD 811 or that supplied from the FD 812.

That is, the CPU 801 reads out a processing program according to a predetermined processing sequence from the ROM 802, HD 811, or FD 812, and executes it, thereby making control for implementing the operations in the first to 19th embodiments.

The RAM 803 serves as a main memory or work area of the CPU 801.

The KBC 805 controls instruction inputs from the KB 809, a pointing device (not shown), and the like. The CRTC 806 controls display on the CRT 810.

The DKC 807 controls access to the HD 811 and FD 812, which store a boot program, various applications, edit files, user files, network management program, predetermined processing programs in the first to 19th embodiments, and the like.

The NIC 808 controls two-way data exchange with another apparatus or system on the network 840.

As described above, the present invention can provide a radiation image processing apparatus, image processing system, radiation image processing method, storage medium, and program, which can obtain a high-quality radiation image, from which image components resulting from a grid, from a radiation image obtained by radiography using the grid.

In a case where the present invention is applied to the aforesaid storage medium, the storage medium stores program codes corresponding to the flowcharts described in the embodiments.

The present invention is not limited to the above embodiments and various changes and modifications can be made within the spirit and scope of the present invention. Therefore to apprise the public of the scope of the present invention, the following claims are made.

What is claimed is:

1. An apparatus for processing a radiation image of an object obtained by radiography using a grid which is used to remove scattered radiation from the object, to remove image components due to the grid, comprising:

generation means for generating the image components due to the grid on the basis of data of the radiation image, comprising analysis means for analyzing the radiation image to obtain a spatial frequency and optionally an angle of a periodic pattern that the image components form, extraction means for extracting predetermined components containing the image components from the radiation image on the basis of an analysis result from said analysis means, and processing means for processing the predetermined components obtained by said extraction means to obtain the image components; and removing means for removing the image components obtained by said processing means from the radiation image, wherein said processing means executes a process for estimating and processing an unsteady portion of the predetermined components from steady portions before and after the unsteady portion as the process of the predetermined components, and wherein said processing means estimates an amplitude and phase of a sine wave corresponding to the image components on the basis of the steady portions of the predetermined components before and after the unsteady portion, and the spatial frequency, and mends the unsteady portion on the basis of the estimation result.

2. The apparatus according to claim 1, wherein said generation means generates the image components on the basis of a feature that the image components superposed on the radiation image are steady.

3. The apparatus according to claim 1, wherein said extraction means executes filtering for extracting components having the spatial frequency obtained by said analysis means from the radiation image.

4. The apparatus according to claim 1, wherein said processing means detects the unsteady portion on the basis of envelope information of the predetermined components.

5. The apparatus according to claim 1, wherein said processing means obtains the image components by executing another filtering of the mended predetermined components.

6. The apparatus according to claim 1, wherein said processing means obtains the image components by substituting an unsteady portion that satisfies a predetermined condition in the unsteady portion by a predetermined value.

7. The apparatus according to claim 1, wherein said generation means executes the generation process of the image components for a predetermined line selected from the radiation image.

8. The apparatus according to claim 7, wherein said generation means executes the generation process for a resulted line data obtained by averaging a plurality of lines selected from the radiation image.

9. The apparatus according to claim 7, wherein said generation means executes the generation process of the image components for the predetermined line which is representative of a plurality of lines of the radiation image.

10. The apparatus according to claim 1, further comprising:

image extraction means for extracting a partial image corresponding to a radiation irradiation field from the radiation image, and wherein said generation means generates the image components of the partial image obtained by said image extraction means.

11. The apparatus according to claim 1, further comprising:

detection means for detecting if the grid is used for radiography, and wherein said generation means executes the process on the basis of a detection result of said detection means.

12. The apparatus according to claim 1, further comprising:

image storage means for storing a radiation image obtained by removing the image components generated by said generation means from the radiation image.

13. The apparatus according to claim 1, further comprising:

image sensing means for capturing the radiation image by a solid-state image sensing element having an image-receiving surface with a size within which a spatial distribution of radiation, at the image-receiving surface, corresponding to the object to be captured falls.

14. The apparatus according to claim 1, further comprising:
image component storage means for storing the image components generated by said generation means.

15. A system for processing a radiation image of an object obtained by radiography using a grid which is used to remove scattered radiation from the object, to remove image components due to the grid, said system being built by connecting a plurality of apparatuses intercommunicatably, comprising:
generation means for generating the image components due to the grid on the basis of data of the radiation image, comprising
analysis means for analyzing the radiation image to obtain a spatial frequency and optionally an angle of a periodic pattern that the image components form,
extraction means for extracting predetermined components containing the image components from the radiation image on the basis of an analysis result from said analysis means, and
processing means for processing the predetermined components obtained by said extraction means to obtain the image components; and
removing means for removing the image components obtained by said processing means from the radiation image,
wherein said processing means executes a process for estimating and processing an unsteady portion of the predetermined components from steady portions before and after the unsteady portion as the process of the predetermined components, and
wherein said processing means estimates an amplitude and phase of a sine wave corresponding to the image components on the basis of the steady portions of the predetermined components before and after the unsteady portion, and the spatial frequency, and mends the unsteady portion on the basis of the estimation result.

16. A method of processing a radiation image of an object obtained by radiography using a grid which is used to remove scattered radiation from the object, to remove image components due to the grid, comprising:
a generation step of generating the image components due to the grid on the basis of data of the radiation image, comprising
an analysis step of analyzing the radiation image to obtain a spatial frequency and optionally an angle of a periodic pattern that the image components form,
an extraction step of extracting predetermined components containing the image components from the radiation image on the basis of an analysis result from said analysis step, and
a processing step of processing the predetermined components obtained in said extraction step to obtain the image components; and
a removing step of removing the image components obtained in said processing step from the radiation image,
wherein said processing step includes executing a process for estimating and processing an unsteady portion of the predetermined components from steady portions before and after the unsteady portion as the process of the predetermined components,
wherein said processing step includes estimating an amplitude and phase of a sine wave corresponding to the image components on the basis of the steady portions of the predetermined components before and after the unsteady portion, and the spatial frequency, and mending the unsteady portion on the basis of the estimation result, and
wherein said steps are performed using a processor and a memory.

17. A computer-readable storage medium storing, in executable form, a program for making a computer execute a method of processing a radiation image of an object obtained by radiography using a grid which is used to remove scattered radiation from the object, to remove image components due to the grid, said method comprising:
a generation step of generating the image components due to the grid on the basis of data of the radiation image, comprising
an analysis step of analyzing the radiation image to obtain a spatial frequency and optionally an angle of a periodic pattern that the image components form,
an extraction step of extracting predetermined components containing the image components from the radiation image on the basis of an analysis result from said analysis step, and
a processing step of processing the predetermined components obtained in said extraction step to obtain the image components; and
a removing step of removing the image components obtained in said processing step from the radiation image,
wherein said processing step includes executing a process for estimating and processing an unsteady portion of the predetermined components from steady portions before and after the unsteady portion as the process of the predetermined components, and
wherein said processing step includes estimating an amplitude and phase of a sine wave corresponding to the image components on the basis of the steady portions of the predetermined components before and after the unsteady portion, and the spatial frequency, and mending the unsteady portion on the basis of the estimation result.

18. An apparatus for processing a radiation image of an object obtained by radiography using a grid which is used to remove scattered radiation from the object, to remove image components due to the grid, comprising:
analysis means for analyzing the radiation image to obtain a spatial frequency of grid stripes generated on the radiation image due to the grid;
first extraction means for executing frequency band limitation processing on the radiation image on the basis of the spatial frequency to extract the processed radiation image as first grid stripes components;
calculation means for calculating an amplitude value of the first grid stripes components;
second extraction means for substituting a value of the first grid stripes components corresponding to an image portion where the amplitude value is out of a predetermined range with a value estimated from a value of the first grid stripes components corresponding to an image portion where the amplitude value is within the predetermined range to extract the substituted image as second grid stripes components; and
removing means for removing the second grid stripes components from the radiation image.

19. A system for processing a radiation image of an object obtained by radiography using a grid which is used to remove scattered radiation from the object, to remove image components due to the grid, said system being built by connecting a plurality of apparatuses intercommunicatably, comprising:

- analysis means for analyzing the radiation image to obtain a spatial frequency of grid stripes generated on the radiation image due to the grid;
- first extraction means for executing frequency band limitation processing on the radiation image on the basis of the spatial frequency to extract the processed radiation image as first grid stripes components;
- calculation means for calculating an amplitude value of the first grid stripes components;
- second extraction means for substituting a value of the first grid stripes components corresponding to an image portion where the amplitude value is out of a predetermined range with a value estimated from a value of the first grid stripes components corresponding to an image portion where the amplitude value is within the predetermined range to extract the substituted image as second grid stripes components; and
- removing means for removing the second grid stripes components from the radiation image.

20. A method of processing a radiation image of an object obtained by radiography using a grid which is used to remove scattered radiation from the object, to remove image components due to the grid, comprising:

- an analysis step of analyzing the radiation image to obtain a spatial frequency of grid stripes generated on the radiation image due to the grid;
- a first extraction step of executing frequency band limitation processing on the radiation image on the basis of the spatial frequency to extract the processed radiation image as first grid stripes components;
- a calculation step of calculating an amplitude value of the first grid stripes components;
- a second extraction step of substituting a value of the first grid stripes components corresponding to an image portion where the amplitude value is out of a predetermined range with a value estimated from a value of the first grid stripes components corresponding to an image portion where the amplitude value is within the predetermined range to extract the substituted image as second grid stripes components; and
- a removing step of removing the second grid stripes components from the radiation image,
- wherein said steps are performed using a processor and a memory.

21. A computer-readable storage medium storing a program for making a computer execute a method of processing a radiation image of an object obtained by radiography using a grid which is used to remove scattered radiation from the object, to remove image components due to the grid, said method comprising:

- an analysis step of analyzing the radiation image to obtain a spatial frequency of grid stripes generated on the radiation image due to the grid;
- a first extraction step of executing frequency band limitation processing on the radiation image on the basis of the spatial frequency to extract the processed radiation image as first grid stripes components;
- a calculation step of calculating an amplitude value of the first grid stripes components;
- a second extraction step of substituting a value of the first grid stripes components corresponding to an image portion where the amplitude value is out of a predetermined range with a value estimated from a value of the first grid stripes components corresponding to an image portion where the amplitude value is within the predetermined range to extract the substituted image as second grid stripes components; and
- a removing step of removing the second grid stripes components from the radiation image.

* * * * *